United States Patent
Yannone et al.

(10) Patent No.: US 12,392,783 B2
(45) Date of Patent: Aug. 19, 2025

(54) METHODS FOR RAPIDLY DIGESTING BIOPOLYMERS WITH ULTRASTABLE ENZYMES FOR MASS SPECTROMETRY-BASED ANALYSES

(71) Applicant: CINDER BIOLOGICAL, INC., Berkeley, CA (US)

(72) Inventors: Steven M. Yannone, Berkeley, CA (US); Jill O. Fuss, Berkeley, CA (US); Adam Barnebey, Berkeley, CA (US)

(73) Assignee: CINDER BIOLOGICAL, INC., Berkeley, CA (US)

( * ) Notice: Subject to any disclaimer, the term of this patent is extended or adjusted under 35 U.S.C. 154(b) by 621 days.

(21) Appl. No.: 16/758,806

(22) PCT Filed: Oct. 24, 2018

(86) PCT No.: PCT/US2018/057397
§ 371 (c)(1),
(2) Date: Apr. 23, 2020

(87) PCT Pub. No.: WO2019/084196
PCT Pub. Date: May 2, 2019

(65) Prior Publication Data
US 2021/0063408 A1    Mar. 4, 2021

Related U.S. Application Data

(60) Provisional application No. 62/576,374, filed on Oct. 24, 2017.

(51) Int. Cl.
*C12N 9/52*      (2006.01)
*G01N 33/68*      (2006.01)

(52) U.S. Cl.
CPC ........... *G01N 33/6842* (2013.01); *C12N 9/52* (2013.01); *G01N 33/6848* (2013.01)

(58) Field of Classification Search
CPC ........... G01N 33/6842; G01N 33/6848; G01N 33/6818; C12N 9/52; C12N 9/2437
See application file for complete search history.

(56) References Cited

FOREIGN PATENT DOCUMENTS

| WO | WO 2004-097427 | 11/2004 | | |
|---|---|---|---|---|
| WO | WO-2004097427 A1 | * 11/2004 | ......... | G01N 33/6818 |
| WO | WO2007091231 | * 8/2007 | ............... | C12N 9/24 |
| WO | WO 2014-081973 | 5/2014 | | |

OTHER PUBLICATIONS

Chen et al, Designing Protease Sensors for Real-Time Imaging of Trypsin Activation in Pancreatic Cancer Cells. Biochemistry 2009, 48, 3519-3526.*
Tang et al, Chapter 66. Thermopsin. Handbook of Proteolytic Enzymes 2nd Edn, 2004 p. 225-227.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
McCabe et al., Journal of Proteomics 289:104992, pp. 1-13, 2023.*
Yannone et al., bioRxiv doi.org/ 10.1101/ 2024.06.01.596979, Jun. 2, 2024.*
International Search Report and Written Opinion for International Patent Application No. PCT/US2018/057397, dated Feb. 5, 2019, 12 pages.
Park et al., "A Thermophilic Ionic Liquid Tolerant Cellulase Cocktail for the Production of Cellulosic Biofuels", PLos One 7(5): e7010. https://doi.org/10.1371/journal.pone.0037010, Published May 23, 2012.

* cited by examiner

*Primary Examiner* — Delia M Ramirez
(74) *Attorney, Agent, or Firm* — SQUIRE PATTON BOGGS (US) LLP

(57) ABSTRACT

The present disclosure relates to a composition containing an ultrastable enzyme, methods of using the same for preparing a biological sample for analysis by mass spectrometry, and kits comprising the same. The composition includes an ultrastable enzyme isolated from a hyperthermophilic and/or acidophilic organism and optionally, an acid and an additive. The composition can be used at temperatures ranging from about 50° C. to 110° C., preferably at temperatures ranging from about 70° C. to 100° C. In addition, the composition can be used at pH values ranging from 0.5 to 7, preferably at pH values ranging from 2 to 5.

19 Claims, 10 Drawing Sheets
Specification includes a Sequence Listing.

Summary

| Catalog# | Class | Optimal pH | pH Range | Optimal Temp. | Temp. Range | Half-life (at optima) |
|---|---|---|---|---|---|---|
| CB-23726 | Protease | 3.0 | *1.8-4.2 | 70 °C | *40-100 °C | 144h (6 days) |

| Catalog# | Class | Optimal pH | pH Range | Optimal Temp. | Temp. Range | Half-life (at optima) |
|---|---|---|---|---|---|---|
| CB-14057 | Protease | 3.0 | *1.5-4.0 | 70 °C | *38-100 °C | >200h (10 days) |

| Catalog# | Class | Optimal pH | pH Range | Optimal Temp. | Temp. Range | Half-life (at optima) |
|---|---|---|---|---|---|---|
| CB-13153 | Protease | 2.5 | *1.5-4.5 | 80 °C | *50-105 °C | 29 hrs |

FIG. 1 (Cont.)

| Enzyme | P1' (begin) | P1 (end) | Putative cut sites | Putative classification |
|---|---|---|---|---|
| CB23726 | F, L, Q | A,K,L | F or L | Pepsin-like |
| CB14057 | E, Q, L | Q,K,A | E or Q | Novel |
| CB13153 | Q, L | L,Q,K,Y | Q or L | Novel |
| Trypsin* | K | Not P | K* | - |
| Pepsin | F, L | - | F or L | - |

* Exceptions known

FIG. 5

METHODS FOR RAPIDLY DIGESTING BIOPOLYMERS WITH ULTRASTABLE ENZYMES FOR MASS SPECTROMETRY-BASED ANALYSES

CROSS-REFERENCE TO RELATED APPLICATIONS

This application is a national stage of international application no. PCT/US2018/057397, filed Oct. 24, 2018, which claims the benefit of U.S. provisional application No. 62/576,374 filed Oct. 24, 2017, the contents of each of which are hereby incorporated by reference in their entirety.

FIELD OF THE INVENTION

The present disclosure generally relates to compositions comprising a thermally and/or acid stable enzyme and optionally, an acid, detergent, alkylating agent, and/or other chemical, and methods of using the same, for preparation of samples for proteomic, glycomic, glycoproteomic, or other chemical, biochemical, or immunochemical analyses.

REFERENCE TO SEQUENCE LISTING

This application includes an electronically submitted sequence listing in .txt format. The .txt file contains a sequence listing entitled "15797.00017_ST25.txt" created on May 27, 2025, and is 159,472 bytes in size. The sequence listing contained in this .txt file is part of the specification and is hereby incorporated by reference herein in its entirety.

BACKGROUND

Proteins are essential cellular machinery, performing and enabling tasks within biological systems. The variety of proteins is extensive, and the role they occupy in biology is deep and complex. Each step of cellular generation, from replication of genetic material to cell senescence and death, relies on the correct function of several distinct proteins. The precision of cellular machinery can be disrupted, however, resulting in disease. Because much of the machinery essential to cell health and survival remains unknown, studying proteins is of great interest and importance.

Proteomics involves the large-scale study of proteins and their ability to regulate cellular functions, including analyzing their presence, modification status, and quantities in biological samples. The field of proteomics encompasses many techniques, such as immunoassays and two-dimensional differential gel electrophoresis (2-D DIGE). Another group of methodologies that are growing in popularity for protein discovery and analyses are mass spectrometry-based approaches. However, in circumstances where biological samples are mass-limited, obtaining sufficient quantities of proteins to generate high-quality mass spectrometric data can pose a challenge. The quality and interpretation of proteomic analyses depend largely on the amount and nature of the proteins to be analyzed. The modification status and inherent nature of the proteins under study pose limitations to these types of analyses. Thus, sample preparation approaches that are time-consuming, or worse, fail to digest the target proteins or incur massive sample losses, are intolerable. There is a thus a need for techniques to prepare limited quantities of biological sample for analysis by mass spectrometry that are rapid, overcome existing limitations, and preserve protein quantities in the sample without large sample loss.

Current mass spectrometry-based analyses face technical limitations that are primarily due to limitations of the enzymes used for biomolecule digestion. Target biopolymer digestion times, digestion completeness, and enzyme compatibility with chemical reagents are all limiting factors in the state-of-the-art procedures and limit throughput and quality of biomolecule analyses. Accordingly, disclosed herein are ultrastable enzymes that address these issues and offer novel capabilities to modern proteomic, lipomic, glycomic, and glycoproteomic approaches.

SUMMARY

Provided herein are methods of preparing a biological sample, wherein the method includes: (a) providing the biological sample containing at least one biopolymer; (b) contacting the sample with a composition containing an ultrastable enzyme to form a reaction mixture; and (c) incubating the reaction mixture for at least one second, resulting in the digestion or modification of the at least one biopolymer present in the biological sample. In some embodiments, the biological sample can be prepared for mass spectrometry-based proteomic analysis, glycomic analysis, glycoproteomic analysis, lipomic analysis, amino acid analysis, enzymatic analysis, or immunochemical analysis.

In some embodiments, the biological sample is one selected from the group consisting of: a tissue, a cell pellet, a cell lysate, a cell culture solution, a biological fluid, a plant tissue, a plant fluid, a food product, an environmental sample, a gel sample and the like.

In some embodiments, the composition containing the ultrastable enzyme further includes one or more agents selected from the group of: a detergent, an acid, an oxidizer, a surfactant, an additive for biopolymer digestion, a reactive and/or chaotropic chemical component, and mixtures thereof.

In some embodiments, the composition containing the ultrastable enzyme further includes an acid. In some embodiments, the acid is selected from the group consisting of: nitric acid, phosphoric acid, hydrofluoric acid, sulfuric acid, hydrochloric acid, acetic acid, paracetic acid, citric acid, glycolic acid, formic acid, and mixtures or combinations thereof.

In some embodiments, the composition containing the ultrastable enzyme further includes a surfactant or detergent. In some embodiments, the surfactant or detergent is selected from the group consisting of: CHAPS, Big CHAP, CHAPSO, NP-40, sodium dodecyl sulfate (SDS), polysorbate 20 (Tween 20), polysorbate 80 (Tween 80), Triton® X-100, octyl glucoside, octyl thioglucoside, deoxycholate, and mixtures or combinations thereof.

In some embodiments, the composition containing the ultrastable enzyme further includes an additive for biopolymer digestion or biopolymer modification. In some embodiments, the additive is selected from the group consisting of: iodoacetamide (IAA), dithiothreitol (DTT), RapiGest SF, PPS Silent® Surfactant, Invitrosol™, ProteaseMAX™, and mixtures or combinations thereof.

In some embodiments, the ultrastable enzyme is isolated from an organism of the Archaea domain. In some embodiments, the ultrastable enzyme is isolated from an organism of the Sulfolobales order.

In some embodiments, the ultrastable enzyme is is selected from the group consisting of: a protease, a lipase, a cellulase, a hemicellulase, a glycoside hydrolase, an endoprotease, a carboxyesterase, an amylase, an alpha-amylase, an endoglucanase, an endopullulanase, a PNGase, a trehalase, a pullulanase, a peptidase, a signal peptidase, a xylanase, a cellobiohydrolase (CBH), a β-glucosidase, a peroxidase, a phospholipase, an esterase, a cutinase, a pectinase, a pectate lyase, a mannanase, a keratinase, a reductase, an oxidase, a phenoloxidase, a lipoxygenase, a ligninase, a tannase, a pentosanase, a malanase, a Q-glucanase, an arabinosidase, a hyaluronidase, a chondroitinase, a lactase, a xyloglucanase, a xanthanase, an acyltransferase, a galactanase, a xanthan lyase, a xylanase, an arabinase, a glycohydrolase, a glycosyltransferase, a glycosidase, and combinations thereof.

In any of the foregoing embodiments, the reaction mixture in step (c) can be incubated at a temperature of at least 50° C. In some embodiments, the reaction mixture in step (c) is incubated at at a temperature of from about 50° C. to about 150° C. In some embodiments, the reaction mixture in step (c) is incubated at a temperature of from about 60° C. to about 125° C. In some embodiments, the reaction mixture in step (c) is incubated at a temperature of from about 70° C. to about 100° C. In some embodiments, the reaction mixture in step (c) is incubated at a temperature of from about 75° C. to about 90° C. In some embodiments, the reaction mixture in step (c) is incubated at a temperature of from about 75° C. to about 85° C. In some embodiments, the reaction mixture in step (c) is incubated at a temperature of from about 75° C. to about 80° C.

In any of the foregoing embodiments, the reaction mixture in step (c) can be incubated at a pH of from about 0.5 to about 7.0.

In some embodiments, the reaction mixture in step (c) is incubated at a pH of from about 0.5 to about 4.5. In some embodiments, the reaction mixture in step (c) is incubated at a pH of from about 0.5 to about 3.0. In some embodiments, the reaction mixture in step (c) is incubated at a pH of from about 0.5 to about 1.5.

In some embodiments, the reaction mixture in step (c) is incubated at a pH of from about 4 to about 7. In some embodiments, the reaction mixture in step (c) is incubated at a pH of about 5.5. In some embodiments, the reaction mixture in step (c) is incubated at a pH of about 3.0.

In some embodiments, the reaction mixture in step (c) is incubated for less than 8 hours, less than 4 hours, less than 2 hours, less than 1 hour, less than 45 minutes, less than 30 minutes, less than 15 minutes, less than 10 minutes, less than 5 minutes, less than 1 minute, less than 30 seconds, or less than 10 seconds.

In some embodiments, the reaction mixture in step (c) is incubated for a duration of time ranging from about 5 minutes to about 300 minutes. In some embodiments, the reaction mixture in step (c) is incubated for a duration of time ranging from about 10 minutes to about 150 minutes. In some embodiments, the reaction mixture in step (c) is incubated for a duration of time ranging from about 20 minutes to about 90 minutes. In some embodiments, the reaction mixture in step (c) is incubated for a duration of time ranging from about 30 minutes to about 75 minutes. In some embodiments, the reaction mixture in step (c) is incubated for a duration of time ranging from about 40 minutes to about 60 minutes.

In some embodiments, the reaction mixture in step (c) is incubated for a duration of time ranging from about 1 second to about 120 minutes, or from about 30 seconds to about 100 minutes, or from about 1 minute to about 90 minutes, or from about 10 minutes to about 75 minutes, or from about 30 minutes to about 60 minutes. In some embodiments, the composition is incubated with target material for a duration of time of less than about 45 minutes, or less than about 30 minutes, or less than about 20 minutes, or less than about 10 minutes. In some embodiments, the composition is incubated with target material for a duration of time of less than about 5 minutes.

In any of the foregoing embodiments, the method can produce at least about 5% digestion of the biopolymer in the sample. In some embodiments, the method results in at least about 30% digestion of the biopolymer in the sample. In some embodiments, the method results in at least about 35% of digestion of the biopolymer in the sample. In some embodiments, the method results in at least about 40% digestion of the biopolymer in the sample. In some embodiments, the method results in at least about 45%, 50%, 55%, 60%, 65%, 70%, 75%, 80%, 85%, 90%, or 95% digestion of the biopolymer in the sample. In some embodiments, the percentage of digestion is measured on a (w/w) basis. In some embodiments, the percentage of digestion is measured on a mass/mass basis.

In any of the foregoing embodiments, the method can further include a step (c)(i) involving addition of an aqueous solution or water to the reaction mixture, wherein the addition of an aqueous solution or water to the reaction mixture reduces the enzymatic activity of the composition. In some embodiments, the addition of an aqueous solution or water to the reaction mixture results in changing the pH of the reaction mixture to a pH value ranging from about 4.5 to about 7.0. In some embodiments, the addition of an aqueous solution or water to the reaction mixture results in changing the temperature of the reaction mixture to a temperature ranging from about 30° C. to about 37° C.

In some embodiments, the method further includes a step (c)(ii) involving adjustment of the temperature of the reaction mixture to a temperature ranging from about 30° C. to about 37° C.

In some embodiments, the method further includes a step (d) of treating the reaction mixture to remove one of more contaminants.

In some embodiments, treating the reaction mixture in step (d) includes removing one or more contaminants from the reaction mixture by filtration or ultra-filtration.

In some embodiments, treating the reaction mixture in step (d) includes removing one or more contaminants from the reaction mixture by selective precipitation. In some embodiments, the selective precipitation is carried out by acetone precipitation, trichloroacetic acid (TCA) precipitation, chloroform-methanol precipitation, and/or ethyl acetate precipitation. In some embodiments, the selective precipitation is carried out in deoxycholate.

In some embodiments, treating the reaction mixture in step (d) includes removing one or more contaminants from the reaction mixture by chromatography. In some embodiments, the chromatography is high-performance liquid chromatography (HPLC) or ultra-performance liquid chromatography (UPLC).

In some embodiments, a combination of separation procedures can be used in step (d) to remove one or more contaminants from the reaction mixture, wherein the separation procedures involve one or more of filtration, ultrafiltration, selective precipitation, and chromatography.

In some embodiments, the method further includes a step (e) of drying the reaction mixture.

In any of the foregoing embodiments, the method can further include storing the prepared sample for a duration of time ranging from about 30 days to about 10 years. In some embodiments, the prepared sample is stored at room temperature. In some embodiments, the prepared sample is stored at 4° C. In some embodiments, the prepared sample is stored at −20° C. In some embodiments, the prepared sample is stored at −80° C.

In some embodiments, the prepared sample is stored in a dried form. In some embodiments, the prepared sample is stored in dried form on a centrifugal membrane.

In some embodiments, the prepared sample is stored in an aqueous form. In some embodiments, the prepared sample is stored in aqueous form in multiwell plates.

In some embodiments, the prepared sample is stored in dried form in PCR tubes. In some embodiments, the prepared sample is stored in aqueous form in PCR tubes.

In some embodiments, the method of any of the foregoing embodiments is part of a one-step sample preparation protocol. In some embodiments, the method is a stand-alone protocol in a multi-step sample preparation process.

Also provided herein are compositions comprising enzymes that increase the efficiency, chemical ranges, substrate complexity, surfactant spectra, and speed of proteolytic digestions for mass spectrometry and other analytical applications. The operating thermal ranges of the enzymes can range from 40° C. to 110° C. at pH of 0-7. The enzymes can function in the presence of detergents or surfactants, acids, iodoacetamide (IAA), and/or dithiothreitol (DTT) among other additives.

In some embodiments, the enzyme(s) included in the composition are isolated from an organism of the Archaeal domain. In some embodiments, the enzyme is isolated from an organism of the Sulfolobales order.

In some embodiments, the enzyme included in the composition is selected from the group consisting of: a protease, a lipase, a cellulase, a hemicellulase, a glycoside hydrolase, an endoprotease, a carboxyesterase, an amylase, an alpha-amylase, an endoglucanase, an endopullulanase, a PNGase, a trehalase, a pullulanase, a peptidase, a signal peptidase, a xylanase, a cellobiohydrolase (CBH), a β-glucosidase, a peroxidase, a phospholipase, an esterase, a cutinase, a pectinase, a pectate lyase, a mannanase, a keratinase, a reductase, an oxidase, a phenoloxidase, a lipoxygenase, a ligninase, a tannase, a pentosanase, a malanase, a Q-glucanase, an arabinosidase, a hyaluronidase, a chondroitinase, a laccase, a xyloglucanase, a xanthanase, an acyltransferase, a galactanase, a xanthan lyase, a xylanase, an arabinase, a glycosyltransferase, a glycosidase, an endoglycosidase, an exo-glycosidase, and combinations thereof.

In some embodiments, the composition further includes chemical additive as disclosed herein.

In some embodiments, the composition is effective for digesting biopolymers in a biological sample at a temperature of from about 50° C. to about 110° C. In some embodiments, the composition is effective for digesting biopolymers in a biological sample at a temperature of from about 60° C. to about 100° C. In some embodiments, the composition is effective for digesting biopolymers in a biological sample at a temperature of from about 70° C. to about 90° C., or from about 70° C. to about 85° C., or from about 75° C. to about 85° C., or from about 75° C. to about 80° C.

In some embodiments, the composition is effective for digesting biopolymers in a biological sample at a pH of from about 0.5 to about 7. In some embodiments, the composition is effective for digesting biopolymers in a biological sample at a pH of from about 0.5 to about 4.5, or from about 0.5 to about 3.0, or from about 0.5 to about 1.5. In some embodiments, the composition is effective for digesting biopolymers in a biological sample at a pH of from about 4 to about 7. In some embodiments, the composition is effective for digesting biopolymers in a biological sample at a pH of about 5.5. In some embodiments, the composition is effective for digesting biopolymers in a biological sample at a pH of about 3.0.

Embodiments are also directed to a kit for digestion of a biopolymer in a biological sample, wherein the kit includes: an enzyme or enzyme mixture, an acid, optionally one or more additives, and instructions for their use, wherein the enzyme or enzyme mixture is an ultrastable, hyperthermophilic, and/or acidophilic enzyme or enzyme mixture as disclosed herein. In some embodiments, the enzyme or enzyme mixture is provided as a lyophilized product. In some embodiments, the enzyme or enzyme mixture is provided as a suspension. In some embodiments, the enzyme or enzyme mixture is provided as a solution. In some embodiments, the enzyme or enzyme mixture is immobilized on a surface.

In some embodiments directed to the kit, the enzyme or enzyme mixture, the acid and the optional additive(s) are provided in separate, individual containers. In some embodiments, the enzyme (or enzyme mixture) and the acid are provided in the same container, and the optional additive(s) are provided in a separate container. In some embodiments, the acid and optional additive(s) are provided in the same container, and the enzyme (or enzyme mixture) is provided in a separate container.

In some embodiments directed to the kit, the enzyme or enzyme mixture is provided in one container, and an optionally provided diluent is provided in a second, separate container. In some embodiments, instructions for preparing the enzyme or enzyme mixture in the optionally provided diluent are provided.

These and other embodiments along with many of its features are described in more detail in conjunction with the text below and attached figures.

BRIEF DESCRIPTION OF THE FIGURES

FIG. 5 includes a table summarizing the results of the peptide mapping and cleavage specificity of exemplified proteases described herein. CB14057 (SEQ ID NO. 26), and CB23726 (SEQ ID NO: 35) are described.

DETAILED DESCRIPTION OF THE EMBODIMENTS

Figure 1:
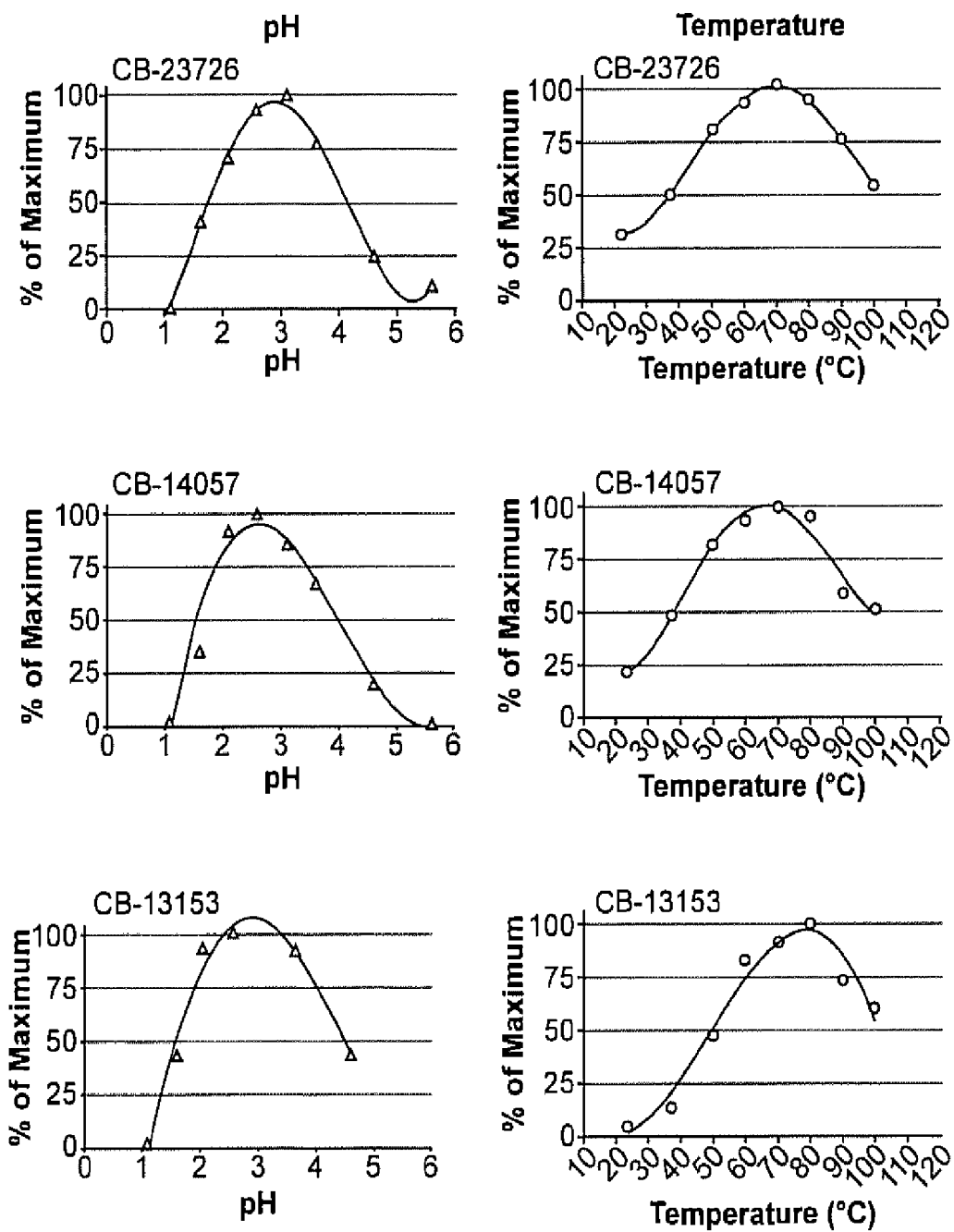
FIG. 1 is a graph illustrating enzymatic activity of three exemplary purified and characterized ultrastable protease enzymes over a range of pH and temperature values.

The methods and compositions disclosed herein generally relate to methods for exploiting the atypical characteristics of enzymes that function optimally at high temperatures and in acidic conditions. In addition, the enzymes disclosed herein retain stability and activity in a broad set of additives (e.g. detergents, surfactants, acids, and redox compounds) that render them suitable for quickly digesting biological samples in the presence of the additives for molecular analyses, including analysis by mass spectrometry (MS).

Provided herein are methods for rapidly and efficiently preparing biological samples for protein analysis. The methods comprise proteolytic cleavage of biological samples using the enzymes disclosed herein to digest target proteins under conditions that promote elevated thermal and pH denaturing of target proteins, removal of post-translational modifications, and degradation of interfering molecules and structures. In some embodiments, the methods disclosed herein provide sufficient digestion to be achieved more rapidly and/or with lower enzyme doses while tolerating varied chemical reaction conditions and surfactants, leading to improved digestion and access to primary amino acid sequences in a target substrate (e.g., a three-dimensional protein with post-translational modification). Non-standard reaction conditions and additives for digestion reactions are provided during sample preparation based on the novel properties of ultrastable hyperthermophilic and/or acidophilic proteases and other enzyme classes.

Previously, a suite of enzymes that function optimally extreme temperatures and highly acidic conditions was described (WO 2014/081973, incorporated herein by reference in its entirety). Disclosed herein are compositions comprising acid- and heat-stable enzymes and methods of using the same for degrading proteins and other biopolymers under extreme heat and acidic conditions in combination with detergents, surfactants and/or other chemical additives. The efficacy of combined thermal/acid/enzyme treatments for degrading proteins and other biopolymers into fragments suitable for proteomic analysis, including mass spectrometry, is demonstrated. Also provided herein are applications for degrading proteins and other biopolymers from single-celled organisms, tissues and biological fluids, using ultrastable enzymes in combination with heat and/or acid and/or detergents and surfactants as well as other chemical additives.

1. Definitions

Unless defined otherwise, all technical and scientific terms used herein have the same meaning as is commonly understood by one of ordinary skill in the art. In the event that there is a plurality of definitions for a term herein, those in this section prevail unless stated otherwise.

As used herein, the singular forms "a," "an," and "the" include the plural reference unless the context clearly indicates otherwise. Thus, for example, reference to an "an enzyme" is a reference to one or more enzymes, etc.

As used herein, the term "isolated" refers to an enzyme that is substantially or essentially free of components that normally accompany or interact with the enzyme as found in its naturally occurring environment or in its production environment, or both. Isolated enzyme preparations have less than about 30%, less than about 25%, less than about 20%, less than about 15%, less than about 10%, less than about 5%, less than about 4%, less than about 3%, less than about 2% or less than about 1% of contaminating protein by weight, e.g. dry weight. In some embodiments, an isolated enzyme preparation exhibits target enzyme activity of greater than 85%, 90%, 95%, 96%, 97%, 98%, 99%, or 99.5% of detectable total enzyme activity.

As used herein, the term "optimal," in reference to enzymatic activity, refers to the ability of the enzyme to act upon an enzyme substrate (e.g., a biomolecule) and carry out its catalytic activity, wherein the catalytic activity is the maximum activity observed at a particular parameter value relative to the activity observed over a range of parameter values the includes the particular parameter value. Parameters for assessing optimal enzymatic activity include, but are not limited to, pH, temperature, and the presence of components that can inhibit the activity of an enzyme.

The term "stable" in reference to an enzyme relates to the enzyme's ability to retain its function and/or activity over time. The term "stable" is used herein as a relative term to compare the enzyme's ability to retain its function and/or activity over time in two or more different states or conditions. For example, a hyperthermophilic and/or acidophilic enzyme is referred to as being stable under high temperature and/or low pH conditions in comparison to a condition when the enzyme is not in those conditions. In some embodiments, an enzyme is stable if it retains at least about 50%, 55%, 60%, 65%, 75%, 80%, 85%, 90%, 95%, 98%, 99%, or any amount included between any two of these values, of its function and/or activity over time.

The term "ultrastable" in reference to an enzyme refers to an enzyme or protein that exhibits activity at temperatures greater than about 60° C. and/or at pH values less than about 5.5. Ultrastable enzymes typically exhibit one or more "hyperthermophilic" and/or "acidophilic" traits, as discussed below, and/or tolerance for detergents, solvents, oxidizers, and other typically enzyme-incompatible chemicals at elevated temperatures and/or acidic pH. For example, in some embodiments, ultrastable enzymes exhibit stability and activity at temperatures ranging from about 60° C. to about 125° C. as described herein. In some embodiments, ultrastable enzymes exhibit activity and stability at pH values ranging from about 0.5 to about 5.5. In some embodiments, an ultrastable enzyme exhibits a half-life ranging from about 1 hour to about 300 hours at temperatures ranging from about 60° C. to about 125° C. and/or at pH values ranging from about 0.5 to about 5.5. In some embodiments, ultrastable enzymes exhibit resistance to chemical and enzymatic degradation, denaturation, and inactivation and exhibit retention of at least about 50% of enzymatic activity in the presence of a chemical and enzymatic degradant, denaturant, or inactivator relative to activity in the absence of the degradant, denaturant, or inactivator. For example, in some embodiments, ultrastable enzymes exhibit resistance to proteolysis and inactivation by mesophilic proteases and exhibit retention of at least about 50% of enzymatic activity in the presence of a mesophilic protease relative to activity in the absence of the mesophilic protease. In some embodiments, ultrastable enzymes exhibit resistance to proteolysis by hyperthermophilic proteases and exhibit retention of at least about 50% of enzymatic activity in the presence of a hyperthermophilic protease relative to activity in the absence of the hyperthermophilic protease.

The term "half-life" of an enzyme typically refers to the time required for the activity of an enzyme to be reduced by one-half.

The term "hyperthermophilic," in reference to an enzyme or protein, refers to an enzyme or protein which is capable of activity at temperatures ranging from about 60° C. to about 125° C. However, in some embodiments, a hyperthermophilic enzyme or protein can operate outside of this temperature range. For example, in some embodiments, a hyperthermophilic enzyme can be active at temperatures as low as 50° C. and as high as 150° C. (i.e. encompassing the "thermophilic" range described herein). Typically, a hyperthermophilic enzyme is active at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, a hyperthermophilic enzyme exhibits at least about 10% of its maximum activity at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, a hyperthermophilic enzyme exhibits at least about 15% of its maximum activity at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, a hyperthermophilic enzyme exhibits at least about 20% of its maximum activity at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, a hyperthermophilic enzyme exhibits at least about 25% of its maximum activity at temperatures of about 60° C., 65° C., 70° C., 75° C., 80° C., 85° C., 90° C., 95° C., 100° C., 105° C., 110° C., 115° C., 120° C., 125° C. or at any temperature included between any two of these values. In some embodiments, a hyperthermophilic enzyme exhibits at least about 30%, 35%, 40%, 45%, 50%, 55%, 60%, 65%, or 75% of its maximum activity, or any percent activity included between any two of these values, at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, "hyperthermophilic" refers to an enzyme or protein which is exhibits activity at temperatures ranging from about 65° C. to about 100° C., or from about 70° C. to about 95° C., or from about 75° C. to about 90° C., or any range included between and including any two of these values. In some embodiments, the hyperthermophilic enzyme or protein exhibits at least about 50% of its maximal activity at temperatures ranging from about 65° C. to about 100° C., or from about 70° C. to about 95° C., or from about 75° C. to about 90° C., or any range included between and including any two of these values. This is in contrast to mesophilic enzymes or components, which in general are capable of growth and/or survival, or exhibit activity, at temperatures ranging from about 20° C. to 40° C.

The term "thermophilic," in reference to an enzyme or protein, refers to an enzyme or protein which is capable of activity at temperatures ranging from about 50° C. to about 150° C. Typically, a thermophilic enzyme is active at temperatures of about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., or at any temperature included between any two of these values. In some embodiments, a thermophilic enzyme exhibits at least about 10% of its maximum activity at temperatures of about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., or at any temperature included between any two of these values. In some embodiments, a thermophilic enzyme exhibits at least about 15% of its maximum activity at temperatures of about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., or at any temperature included between any two of these values. In some embodiments, a thermophilic enzyme exhibits at least about 20% of its maximum activity at temperatures of about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., or at any temperature included between any two of these values. In some embodiments, a thermophilic enzyme exhibits at least about 25% of its maximum activity at temperatures of about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., or at any temperature included between any two of these values. In some embodiments, a thermophilic enzyme exhibits at least about 30%, 35%, 40%, 45%, 50%, 55%, 60%, 65%, or 75% of its maximum activity, or any percent activity included between any two of these values, at temperatures of about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., or at any temperature included between any two of these values. In some embodiments, "thermophilic" refers to an enzyme or protein which is exhibits activity at temperatures ranging from about 50° C. to about 100° C., or from about 55° C. to about 75° C., or from about 60° C. to about 70° C., or any range included between and including any two of these values. In some embodiments, "thermophilic" refers to an enzyme or protein which is exhibits activity at temperatures ranging from about 90° C. to about 150° C., or from about 100° C. to about 145° C., or from about 120° C. to about 140° C., or any range included between and including any two of these values. In some embodiments, the thermophilic enzyme or protein exhibits at least about 50% of its maximal activity at temperatures ranging from about 50° C. to about 100° C., or from about 55° C. to about 75° C., or from about 60° C. to about 70° C., or any range included between and including any two of these values. In some embodiments, the thermophilic enzyme or protein exhibits at least about 50% of its maximal activity at temperatures ranging from about 90° C. to about 150° C., or from about 100° C. to about 145° C., or from about 120° C. to about 140° C., or any range included between and including any two of these values.

The term "acidophilic," in reference to an enzyme or protein, refers to an an enzyme or protein that exhibits activity at pH values ranging from about 0.5 to about 5.5. However, in some embodiments, an acidophilic enzyme or protein can operate outside of this pH range, including, for example, at pH values up to about 7. Typically, an acidophilic enzyme exhibits activity at pH values of about 0.5, 1.0, 1.5, 2.0, 2.5, 3.0, 3.5, 4.0, 4.5, 5.0, 5.5, or at any pH value included between any two of these values. For example, in some embodiments, an acidophilic enzyme exhibits at least about 10% of its maximum activity at pH values of about 0.5, 1.0, 1.5, 2.0, 2.5, 3.0, 3.5, 4.0, 4.5, 5.0, 5.5, or at any pH value included between any two of these values. In some embodiments, an acidophilic enzyme exhibits at least about 15% of its maximum activity at pH values of about 0.5, 1.0, 1.5, 2.0, 2.5, 3.0, 3.5, 4.0, 4.5, 5.0, 5.5, or at any pH value included between any two of these values. In some embodiments, an acidophilic enzyme exhibits at least about 20% of its maximum activity at pH values of about 0.5, 1.0, 1.5, 2.0, 2.5, 3.0, 3.5, 4.0, 4.5, 5.0, 5.5, or at any pH value included between any two of these values. In some embodiments, an acidophilic enzyme exhibits at least about 25% of its maximum activity at pH values of about 0.5, 1.0, 1.5, 2.0, 2.5, 3.0, 3.5, 4.0, 4.5, 5.0, 5.5, or at any pH value included between any two of these values. In some embodiments, an acidophilic enzyme exhibits at least about 30%, 35%, 40%, 45%, 50%, 55%, 60%, 65%, or 75% of its maximum activity, or any percent activity included between any two of these values, at pH values of about 0.5, 1.0, 1.5, 2.0, 2.5, 3.0, 3.5, 4.0, 4.5, 5.0, 5.5, or at any pH value included between any two of these values. In some embodiments, "acidophilic" refers to an enzyme or protein that exhibits optimal activity at pH values ranging from about 0.5 to about 3.5, or from about 0.5 to about 2.5, or from about 0.5 to about 1.5, or from about 2.0 to about 3.0, or any range included between and including any two of these values. In some embodiments, an acidophilic enzyme or protein exhibits at least about 50% of its maximal activity at pH values ranging from about 0.5 to about 3.5, or from about 0.5 to about 2.5, or from about 0.5 to about 1.5, or from about 2.0 to about 3.0, or any range included between and including any two of these values. In some embodiments, an acidophilic enzyme or protein exhibits optimal activity or shows stability at pH values ranging from about 2.0 to about 5.0, or from about 3.0 to about 5.0, or from about 4.0 to about 5.0, or or any range included between and including any two of these values.

As used herein, the terms "degrading" or "digestion," with respect to target substrates or molecules, refers to a procedure that cleaves bonds in the target molecule to produce fragments of the original molecule. In some embodiments, the target molecule is cleaved by about 10%, about 20%, about 30%, about 40%, about 50%, about 60%, about 70%, about 80%, about 90%, about 95%, about 99%, about 100%, or by any amount included between any two of these values, with respect to the total amount of target molecule on a weight or mass basis. In some embodiments, the procedure encompasses removal of post-translational modifications such as sugars, methyl groups, phosphates or other moieties that interfere with analyses as well as cleavage of the target molecule into fragments. The extent to which a target molecule is degraded or digested can be measured by any procedure known to one of ordinary skill in the art.

As used herein, the terms "modifying" or "modification," with respect to target substrates or molecules, refers to any activity that maintains the cleaved bonds in the target molecule to produce fragments of the original molecule. Exemplary modifications include, but are not limited to, reduction of disulfide bonds, methylation, acetylation, and phosphorylation. The extent to which a target molecule is modified can be evaluated by any procedure known to one of ordinary skill in the art.

As used herein, a target substrate or molecule is one that is being prepared for proteomic or other mass spectrometric analysis. The target substrate or molecule can be a biopolymer, including, but not limited to, a protein, a polypeptide, a lipid, a polysaccharide, and the like. In some embodiments, the target substrate or molecule is provided in a sample selected from the group consisting of: a residue of a grain, a dairy product, a fruit, a vegetable, a meat, an animal food, an industrial fermentation product, an algae, a biofuel, a pharmaceutical, a nutritional supplement, a tissue sample, a bodily fluid sample, a cancer biopsy, a single-celled organism, a plant, a plant part, or any combination thereof.

2. Compositions

Embodiments relate to a composition useful for sample preparation and depolymerization of proteins and other biomolecules for mass spectrometry or other analytical analyses. Generally, the compositions comprise a thermally stable and/or an acid stable, and or chemically stable enzyme as disclosed herein. In some embodiments, the compositions also contain an agent useful for denaturing or degrading the biomolecule as disclosed herein. For example, the agent can be an acid, an oxidizer, a detergent, a surfactant, an additive for biopolymer digestion, a reactive and/or chaotropic chemical components, or mixtures thereof.

In some embodiments, the composition has a pH value ranging from about 0.5 to about 7. In some embodiments, the compositions have a pH value ranging from about 0.5 to about 4.5, or from about 0.5 to about 3.0, or from about 0.5 to about 1.5, or any pH range included between and including any two of these values. In some embodiments, the composition has a pH of about 2.0 to 3.0. In some embodiments, the composition has a pH value ranging from about 4 to about 7, or from about 4.5 to about 6.5, or from about 5 to about 6, or any pH range included between and including any two of these values. In some embodiments, the composition has a pH of about 5.5. In some embodiments, the composition has a pH of about 3.0.

Also provided herein are compositions as disclosed herein that can be applied to a sample under pH conditions ranging from about 0.5 to about 7. In some embodiments, the composition can be applied to a sample under pH conditions ranging from about 0.5 to about 4.5, or from about 0.5 to about 3.0, or from about 0.5 to about 1.5, or any pH range included between and including any two of these values. In some embodiments, the composition can be applied to a sample under pH conditions ranging from about 4 to about 7, or from about 4.5 to about 6.5, or from about 5 to about 6, or any pH range included between and including any two of these values. In some embodiments, the composition can be applied to a sample at a pH condition of about 5.5. In some embodiments, the composition can be applied to a sample at a pH condition of about 3.0.

In some embodiments, the compositions disclosed herein can be employed at temperatures ranging from about 60° C. to about 125° C. For example the compositions can be applied to a sample at temperature conditions of about 60° C., 65° C., 70° C., 75° C., 80° C., 85° C., 90° C., 95° C., 100° C., 105° C., 110° C., 115° C., 120° C., 125° C. or any temperature included between any two of these values.

In some embodiments, the compositions disclosed herein are heated to temperatures ranging from about 60° C. to about 125° C. prior to application to a sample. For example the compositions can be heated to a temperature of about 60° C., 65° C., 70° C., 75° C., 80° C., 85° C., 90° C., 95° C., 100° C., 105° C., 110° C., 115° C., 120° C., 125° C., or any temperature included between any two of these values. Once the composition reaches its target temperature within this range, it can be employed as part of a method to degrade, digest, or otherwise prepare biological samples for analysis.

2.1. Enzymes

Any enzyme or mixture of enzymes, from a source that is hyperthermophilic and/or acidophilic, can be provided in the composition, provided that the enzyme or mixture of enzymes is stable in the desired pH range and compatible with the compositions and operating conditions disclosed herein. In some embodiments, the enzyme can be an enzyme isolated and/or produced in a manner described in WO 2014/081973, which is incorporated herein by reference in its entirety. In some embodiments, the enzyme is provided in a solid form, a liquid form, or a lyophilized form.

The enzyme can be provided in an amount that is effective for sample preparation and depolymerization of proteins and other biomolecules for mass spectrometry analyses. In some embodiments, the enzyme is provided in an amount of from about 1 femtogram to 1 milligram of enzyme protein, or from about 1 nanogram to 750 micrograms (μg) of enzyme protein, or from about 1 μg to 500 μg of enzyme protein, or from about 10 μg to 250 μg of enzyme protein, or from about 25 μg to 100 μg of enzyme protein, or any amount included between any two of these values. For example, the amount of enzyme can be about 1 femtogram, 1 nanogram, 1 μg, 10 μg, 25 μg, 50 μg, 100 μg, 250 μg, 500 μg, 1 mg, or any amount included between any two of these values, of enzyme protein per 100 milligrams of sample.

In some embodiments, the enzyme is provided in a concentration that ranges from about 0.0001 wt % to 50 wt %, or from about 0.001 wt % to 40 wt %, or from about 0.01 wt % to 30 wt %, or from about 0.1 wt % to 25 wt %, or from about 0.5 wt % to 20 wt %, or from about 1 wt % to 15 wt %, or from about 2.5 wt % to 10 wt %, or any range included between and including any two of these values. In some embodiments, the enzyme is provided in a concentration of about 0.0001 wt %, 0.001 wt %, 0.01 wt %, 0.1 wt %, 0.25 wt %, 0.5 wt %, 1 wt %, 2 wt %, 2.5 wt %, 3 wt %, 4 wt %, 5 wt %, 10 wt %, 15 wt %, 20 wt %, 25 wt %, 30 wt %, 35 wt %, 40 wt %, 45 wt %, 50 wt %, or any value included between any two of these values.

In some embodiments, the enzyme is provided in an activity range of from about 0.0001 to 100 activity units, or from about 0.001 to 75 activity units, or from about 0.01 to 50 activity units, or from about 0.1 to 25 activity units, or from about 0.5 to 20 activity units, or from about 1 to 15 activity units, or from about 2.5 to 10 activity units, or any range included between and including any two of these values. In some embodiments, the enzyme is provided in an amount of about 0.0001 activity unit, 0.001 activity unit, 0.01 activity unit, 0.1 activity unit, 0.25 activity unit, 0.5 activity unit, 1 activity unit, 2 activity units, 2.5 activity units, 3 activity units, 4 activity units, 5 activity units, 10 activity units, 15 activity units, 20 activity units, 25 activity units, 30 activity units, 35 activity units, 40 activity units, 45 activity units, 50 activity units, 75 activity units, 100 activity units, or amount included between any two of these values.

In some embodiments, the enzyme or enzyme mixture is an acidophilic enzyme or acidophilic enzyme mixture that exhibits activity at pH values ranging from about 0.5 to about 5.5. For example, in some embodiments, the acidophilic enzyme or enzyme mixture exhibits at least about 10% of its maximum activity at pH values of about 0.5, 1.0, 1.5, 2.0, 2.5, 3.0, 3.5, 4.0, 4.5, 5.0, 5.5, or at any pH value included between any two of these values. In some embodiments, the acidophilic enzyme or enzyme mixture exhibits at least about 15% of its maximum activity at pH values of about 0.5, 1.0, 1.5, 2.0, 2.5, 3.0, 3.5, 4.0, 4.5, 5.0, 5.5, or at any pH value included between any two of these values. In some embodiments, the acidophilic enzyme or enzyme mixture exhibits at least about 20% of its maximum activity at pH values of about 0.5, 1.0, 1.5, 2.0, 2.5, 3.0, 3.5, 4.0, 4.5, 5.0, 5.5, or at any pH value included between any two of these values. In some embodiments, the acidophilic enzyme or enzyme mixture exhibits at least about 25% of its maximum activity at pH values of about 0.5, 1.0, 1.5, 2.0, 2.5, 3.0, 3.5, 4.0, 4.5, 5.0, 5.5, or at any pH value included between any two of these values. In some embodiments, the acidophilic enzyme or enzyme mixture exhibits at least about 30%, 35%, 40%, 45%, 50%, 55%, 60%, 65%, or 75% of its maximum activity, or any percent activity included between any two of these values, at pH values of about 0.5, 1.0, 1.5, 2.0, 2.5, 3.0, 3.5, 4.0, 4.5, 5.0, 5.5, or at any pH value included between any two of these values. In some embodiments, the acidophilic enzyme or enzyme mixture exhibits optimal activity at pH values ranging from about 0.5 to about 3.5, or from about 0.5 to about 2.5, or from about 0.5 to about 1.5, or from about 2.0 to about 3.0, or any range included between and including any two of these values. In some embodiments, the acidophilic enzyme or enzyme mixture exhibits at least 50% of its maximal activity at pH values ranging from about 0.5 to about 3.5, or from about 0.5 to about 2.5, or from about 0.5 to about 1.5, or from about 2.0 to about 3.0, or any range included between and including any two of these values. In some embodiments, the acidophilic enzyme or enzyme mixture exhibits optimal activity or shows stability at pH values ranging from about 2.0 to about 5.0, or from about 3.0 to about 5.0, or from about 4.0 to about 5.0, or or any range included between and including any two of these values.

In some embodiments, the enzyme or enzyme mixture is stable in a pH range of from about 0.5 to about 7. In some embodiments, the enzyme or enzyme mixture is active in a pH range of from about 0.5 to about 4.5, or from about 0.5 to about 3.0, or from about 0.5 to about 1.5, or any pH range included between and including any two of these values. In some embodiments, the enzyme or enzyme mixture is active in a pH range of from about 2.0 to 3.0. In some embodiments, the enzyme or enzyme mixture is stable in a pH range of from about 4 to about 7, or from about 4.5 to about 6.5, or from about 5 to about 6, or any pH range included between and including any two of these values. In some embodiments, the enzyme or enzyme mixture is stable at a pH of about 5.5. In some embodiments, the enzyme or enzyme mixture is stable at a pH of about 3.0.

In some embodiments, the enzyme or enzyme mixture demonstrates enzymatic activity in a pH range of from about 0.5 to about 7. In some embodiments, the enzyme or enzyme mixture demonstrates enzymatic activity in a pH range of from about 0.5 to about 4.5, or from about 0.5 to about 3.0, or from about 0.5 to about 1.5, or any pH range included between and including any two of these values. In some embodiments, the enzyme or enzyme mixture demonstrates enzymatic activity in a pH range of from about 2.0 to 3.0. In some embodiments, the enzyme or enzyme mixture demonstrates enzymatic activity in a pH range of from about 4 to about 7, or from about 4.5 to about 6.5, or from about 5 to about 6, or any pH range included between and including any two of these values. In some embodiments, the enzyme or enzyme mixture demonstrates enzymatic activity at a pH of about 5.5. In some embodiments, the enzyme or enzyme mixture demonstrates enzymatic activity at a pH of about 3.0.

In some embodiments, the enzyme or enzyme mixture demonstrates optimal enzymatic activity in a pH range of from about 0.5 to about 7. In some embodiments, the enzyme or enzyme mixture demonstrates optimal enzymatic activity in a pH range of from about 0.5 to about 4.5, or from about 0.5 to about 3.0, or from about 0.5 to about 1.5, or any pH range included between and including any two of these values. In some embodiments, the enzyme or enzyme mixture demonstrates optimal enzymatic activity in a pH range of from about 2.0 to 3.0. In some embodiments, the enzyme or enzyme mixture demonstrates optimal enzymatic activity in a pH range of from about 4 to about 7, or from about 4.5 to about 6.5, or from about 5 to about 6, or any pH range included between and including any two of these values. In some embodiments, the enzyme or enzyme mixture demonstrates optimal enzymatic activity at a pH of about 5.5. In some embodiments, the enzyme or enzyme mixture demonstrates optimal enzymatic activity at a pH of about 3.0.

In some embodiments, the enzyme or enzyme mixture demonstrates at least about 10% of its maximum enzymatic activity in a pH range of from about 0.5 to about 7. In some embodiments, the enzyme or enzyme mixture demonstrates at least about 10% of its maximum enzymatic activity in a pH range of from about 0.5 to about 4.5, or from about 0.5 to about 3.0, or from about 0.5 to about 1.5, or any pH range included between and including any two of these values. In some embodiments, the enzyme or enzyme mixture demonstrates at least about 10% of its maximum enzymatic activity in a pH range of from about 2.0 to 3.0. In some embodiments, the enzyme or enzyme mixture demonstrates at least about 10% of its maximum enzymatic activity in a pH range of from about 4 to about 7, or from about 4.5 to about 6.5, or from about 5 to about 6, or any pH range included between and including any two of these values. In some embodiments, the enzyme or enzyme mixture demonstrates at least about 10% of its maximum enzymatic activity at a pH of about 5.5. In some embodiments, the enzyme or enzyme mixture demonstrates at least about 10% of its maximum enzymatic activity at a pH of about 3.0.

In some embodiments, the enzyme or enzyme mixture demonstrates at least about 15% of its maximum enzymatic activity in a pH range of from about 0.5 to about 7. In some embodiments, the enzyme or enzyme mixture demonstrates at least about 15% of its maximum enzymatic activity in a pH range of from about 0.5 to about 4.5, or from about 0.5 to about 3.0, or from about 0.5 to about 1.5, or any pH range included between and including any two of these values. In some embodiments, the enzyme or enzyme mixture demonstrates at least about 15% of its maximum enzymatic activity in a pH range of from about 2.0 to 3.0. In some embodiments, the enzyme or enzyme mixture demonstrates at least about 15% of its maximum enzymatic activity in a pH range of from about 4 to about 7, or from about 4.5 to about 6.5, or from about 5 to about 6, or any pH range included between and including any two of these values. In some embodiments, the enzyme or enzyme mixture demonstrates at least about 15% of its maximum enzymatic activity at a pH of about 5.5. In some embodiments, the enzyme or enzyme mixture demonstrates at least about 15% of its maximum enzymatic activity at a pH of about 3.0.

In some embodiments, the enzyme or enzyme mixture demonstrates at least about 20% of its maximum enzymatic activity in a pH range of from about 0.5 to about 7. In some embodiments, the enzyme or enzyme mixture demonstrates at least about 20% of its maximum enzymatic activity in a pH range of from about 0.5 to about 4.5, or from about 0.5 to about 3.0, or from about 0.5 to about 1.5, or any pH range included between and including any two of these values. In some embodiments, the enzyme or enzyme mixture demonstrates at least about 20% of its maximum enzymatic activity in a pH range of from about 2.0 to 3.0. In some embodiments, the enzyme or enzyme mixture demonstrates at least about 20% of its maximum enzymatic activity in a pH range of from about 4 to about 7, or from about 4.5 to about 6.5, or from about 5 to about 6, or any pH range included between and including any two of these values. In some embodiments, the enzyme or enzyme mixture demonstrates at least about 20% of its maximum enzymatic activity at a pH of about 5.5. In some embodiments, the enzyme or enzyme mixture demonstrates at least about 20% of its maximum enzymatic activity at a pH of about 3.0.

In some embodiments, the enzyme or enzyme mixture demonstrates at least about 25% of its maximum enzymatic activity in a pH range of from about 0.5 to about 7. In some embodiments, the enzyme or enzyme mixture demonstrates at least about 25% of its maximum enzymatic activity in a pH range of from about 0.5 to about 4.5, or from about 0.5 to about 3.0, or from about 0.5 to about 1.5, or any pH range included between and including any two of these values. In some embodiments, the enzyme or enzyme mixture demonstrates at least about 25% of its maximum enzymatic activity in a pH range of from about 2.0 to 3.0. In some embodiments, the enzyme or enzyme mixture demonstrates at least about 25% of its maximum enzymatic activity in a pH range of from about 4 to about 7, or from about 4.5 to about 6.5, or from about 5 to about 6, or any pH range included between and including any two of these values. In some embodiments, the enzyme or enzyme mixture demonstrates at least about 25% of its maximum enzymatic activity at a pH of about 5.5. In some embodiments, the enzyme or enzyme mixture demonstrates at least about 25% of its maximum enzymatic activity at a pH of about 3.0.

In some embodiments, the enzyme or enzyme mixture demonstrates at least about 30%, 35%, 40%, 45%, 50%, 55%, 60%, 65%, or 75% of its maximum activity, or any percent activity included between any two of these values, in a pH range of from about 0.5 to about 7. In some embodiments, the enzyme or enzyme mixture demonstrates at least about 30%, 35%, 40%, 45%, 50%, 55%, 60%, 65%, or 75% of its maximum activity, or any percent activity included between any two of these values, in a pH range of from about 0.5 to about 4.5, or from about 0.5 to about 3.0, or from about 0.5 to about 1.5, or any pH range included between and including any two of these values. In some embodiments, the enzyme or enzyme mixture demonstrates at least about 30%, 35%, 40%, 45%, 50%, 55%, 60%, 65%, or 75% of its maximum activity, or any percent activity included between any two of these values, in a pH range of from about 2.0 to 3.0. In some embodiments, the enzyme or enzyme mixture demonstrates at least about 30%, 35%, 40%, 45%, 50%, 55%, 60%, 65%, or 75% of its maximum activity, or any percent activity included between any two of these values, in a pH range of from about 4 to about 7, or from about 4.5 to about 6.5, or from about 5 to about 6, or any pH range included between and including any two of these values. In some embodiments, the enzyme or enzyme mixture demonstrates at least about 30%, 35%, 40%, 45%, 50%, 55%, 60%, 65%, or 75% of its maximum activity, or any percent activity included between any two of these values, at a pH of about 5.5. In some embodiments, the enzyme or enzyme mixture demonstrates at least about 30%, 35%, 40%, 45%, 50%, 55%, 60%, 65%, or 75% of its maximum activity, or any percent activity included between any two of these values, at a pH of about 3.0.

In some embodiments, the enzyme or enzyme mixture is a hyperthermophilic enzyme or hyperthermophilic enzyme mixture that exhibits activity at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, the hyperthermophilic enzyme or enzyme mixture exhibits at least about 10% of its maximum activity at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, the hyperthermophilic enzyme or enzyme mixture exhibits at least about 15% of its maximum activity at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, the hyperthermophilic enzyme or enzyme mixture exhibits at least about 20% of its maximum activity at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, the hyperthermophilic enzyme or enzyme mixture exhibits at least about 25% of its maximum activity at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, the hyperthermophilic enzyme or enzyme mixture exhibits at least about 30%, 35%, 40%, 45%, 50%, 55%, 60%, 65%, or 75% of its maximum activity, or any percent activity included between any two of these values, at temperatures of about 60° C., 65° C., 70° C., 75° C., 80° C., 85° C., 90° C., 95° C., 100° C., 105° C., 110° C., 115° C., 120° C., 125° C., or at any temperature included between any two of these values. In some embodiments, the hyperthermophilic enzyme or enzyme mixture exhibits optimal activity at temperatures ranging from about 65° C. to about 100° C., or from about 70° C. to about 95° C., or from about 75° C. to about 90° C., or any range included between and including any two of these values. In some embodiments, the hyperthermophilic enzyme or enzyme mixture exhibits at least about 50% of its maximal activity at temperatures ranging from about 65° C. to about 100° C., or from about 70° C. to about 95° C., or from about 75° C. to about 90° C., or any range included between and including any two of these values.

In some embodiments, the enzyme or enzyme mixture demonstrates enzymatic activity at temperatures ranging from about 50° C. to about 125° C. For example, the enzyme or enzyme mixture demonstrates enzymatic activity at temperature conditions of about 50° C., 55° C., 60° C., 65° C., 70° C., 75° C., 80° C., 85° C., 90° C., 95° C., 100° C., 105° C., 110° C., 110° C., 115° C., 120° C., 125° C., or any temperature included between any two of these values. In some embodiments, the enzyme or enzyme mixture demonstrates optimal enzymatic activity at temperature conditions of about 50° C., 55° C., 60° C., 65° C., 70° C., 75° C., 80° C., 85° C., 90° C., 95° C., 100° C., 105° C., 110° C., 110° C., 115° C., 120° C., 125° C., or any temperature included between any two of these values.

In some embodiments, the enzyme or enzyme mixture demonstrates at least about 10% of its maximum enzymatic activity at temperatures ranging from about 50° C. to about 125° C. For example, the enzyme or enzyme mixture demonstrates at least about 10% of its maximum enzymatic activity at temperature conditions of about 50° C., 55° C., 60° C., 65° C., 70° C., 75° C., 80° C., 85° C., 90° C., 95° C., 100° C., 105° C., 110° C., 110° C., 115° C., 120° C., 125° C., or any temperature included between any two of these values.

In some embodiments, the enzyme or enzyme mixture demonstrates at least about 15% of its maximum enzymatic activity at temperatures ranging from about 50° C. to about 125° C. For example, the enzyme or enzyme mixture demonstrates at least about 15% of its maximum enzymatic activity at temperature conditions of about 50° C., 55° C., 60° C., 65° C., 70° C., 75° C., 80° C., 85° C., 90° C., 95° C., 100° C., 105° C., 110° C., 110° C., 115° C., 120° C., 125° C., or any temperature included between any two of these values.

In some embodiments, the enzyme or enzyme mixture demonstrates at least about 20% of its maximum enzymatic activity at temperatures ranging from about 50° C. to about 125° C. For example, the enzyme or enzyme mixture demonstrates at least about 20% of its maximum enzymatic activity at temperature conditions of about 50° C., 55° C., 60° C., 65° C., 70° C., 75° C., 80° C., 85° C., 90° C., 95° C., 100° C., 105° C., 110° C., 110° C., 115° C., 120° C., 125° C., or any temperature included between any two of these values.

In some embodiments, the enzyme or enzyme mixture demonstrates at least about 25% of its maximum enzymatic activity at temperatures ranging from about 50° C. to about 125° C. For example, the enzyme or enzyme mixture demonstrates at least about 25% of its maximum enzymatic activity at temperature conditions of about 50° C., 55° C., 60° C., 65° C., 70° C., 75° C., 80° C., 85° C., 90° C., 95° C., 100° C., 105° C., 110° C., 110° C., 115° C., 120° C., 125° C., or any temperature included between any two of these values.

In some embodiments, the enzyme or enzyme mixture demonstrates at least about 30%, 35%, 40%, 45%, 50%, 55%, 60%, 65%, or 75% of its maximum activity, or any percent activity included between any two of these values, at temperatures ranging from about 50° C. to about 125° C. For example, the enzyme or enzyme mixture demonstrates at least about 30%, 35%, 40%, 45%, 50%, 55%, 60%, 65%, or 75% of its maximum activity, or any percent activity included between any two of these values, at temperature conditions of about 50° C., 55° C., 60° C., 65° C., 70° C., 75° C., 80° C., 85° C., 90° C., 95° C., 100° C., 105° C., 110° C., 110° C., 115° C., 120° C., 125° C., or any temperature included between any two of these values.

In some embodiments, the enzyme or enzyme mixture demonstrates loss of enzymatic activity at ambient temperature and neutral pH ranges. For example, hyperthermophilic enzymes can undergo loss of activity at temperatures ranging from about 25° C. to 45° C., or from about 30° C. to 37° C. Acidophilic enzymes can undergo loss of activity at neutral pH values of from about 4.5 to 7.0 or above. In embodiments where a hyperthermophilic and/or acidophilic enzyme is provided, lowering temperature conditions to 25° C. to 45° C., and/or raising pH conditions to about 4.5 or above, can result in loss of enzymatic activity. In some embodiments, lowering temperature conditions to about 30° C. to 37° C., and/or raising pH conditions to about 4.5 to 7.0, can result in loss of enzymatic activity. In some embodiments, lowering temperature conditions to about 30° C. to 37° C., and/or raising pH conditions to about 7.0 or above, can result in loss of enzymatic activity. In some embodiments, lowering temperature conditions to about 25° C. to 45° C., or to about 30° C. to 37° C., is sufficient to result in loss of enzymatic activity. In some embodiments, raising the pH to about 4.5 or above, or to about 4.5 to 7.0, or to about 7.0 and above, is sufficient to result in loss of enzymatic activity. In some embodiments, lowering temperature conditions to about 25° C. to 45° C. and raising pH conditions to about 4.5 or above results in loss of enzymatic activity. In some embodiments, lowering temperature conditions to about 30° C. to 37° C. and raising pH conditions to about 4.5 to 7.0 results in loss of enzymatic activity. In some embodiments, lowering temperature conditions to about 30° C. to 37° C. and raising pH conditions to about 7.0 or above results in loss of enzymatic activity. Loss of enzymatic activity can mean a reduction of at least about 25%, 30%, 35%, 40%, 45%, 50%, 55%, 60%, 65%, 70%, 75%, 80%, 85%, 90%, 95% or 100% of enzymatic activity relative to baseline levels at non-ambient temperatures (e.g., about 50° C. to 110° C.) and non-neutral (e.g., about 0.5 to 4.5) pH ranges.

In some embodiments, the enzyme or enzyme mixture is an ultrastable enzyme or ultrastable enzyme mixture. In some embodiments, the ultrastable enzyme or enzyme mixture exhibits stability and activity at temperatures ranging from about 60° C. to about 125° C. as described herein. In some embodiments, the ultrastable enzyme or enzyme mixture exhibits activity and stability at pH values ranging from about 0.5 to about 5.5. In some embodiments, the ultrastable enzyme or enzyme mixture exhibits a half-life ranging from about 1 hour to about 300 hours at temperatures ranging from about 60° C. to about 125° C. and/or at pH values ranging from about 0.5 to about 5.5. In some embodiments, the ultrastable enzyme or enzyme mixture exhibits resistance to chemical and enzymatic degradation, denaturation, and inactivation and exhibit retention of at least about 50% of enzymatic activity in the presence of a chemical and enzymatic degradant, denaturant, or inactivator relative to activity in the absence of the degradant, denaturant, or inactivator.

In some embodiments, the enzyme or enzyme mixture is a hyperthermophilic acidophilic enzyme or a hyperthermophilic acidophilic enzyme mixture. As used herein, the term "hyperthermophilic acidophilic" typically refers to an enzyme that exhibits activity (1) at temperatures ranging from about 60° C. to about 125° C., and (2) at pH values ranging from about 0.5 to about 5.5. In some embodiments, a hyperthermophilic acidophilic enzymes are active (1) at temperatures of about 60° C., 65° C., 70° C., 75° C., 80° C., 85° C., 90° C., 95° C., 100° C., 105° C., 110° C., 115° C., 120° C. 125° C., or at any temperature included between any two of these values, and (2) at pH values of about 0.5, 1.0, 1.5, 2.0, 2.5, 3.0, 3.5, 4.0, 4.25, 4.5, 4.75, 5.0, 5.25, 5.5, or at any pH value included between any two of these values. In some embodiments, a hyperthermophilic acidophilic enzymes exhibit activity (1) at temperatures of about 70° C., 75° C., 80° C., 85° C., 90° C., 95° C., or at any temperature included between any two of these values, and (2) at pH values of about 4.0, 4.25, 4.5, 4.75, 5.0, 5.25, 5.5, or at any pH value included between any two of these values. In some embodiments, a hyperthermophilic acidophilic enzymes exhibit at least about 50% of its maximal activity (1) at temperatures of about 70° C., 75° C., 80° C., 85° C., 90° C., 95° C., or at any temperature included between any two of these values, and (2) at pH values of about 4.0, 4.25, 4.5, 4.75, 5.0, 5.25, 5.5, or at any pH value included between any two of these values. Hyperthermophilic acidophilic enzymes can be isolated or obtained from hyperthermophilic acidophiles or other organisms and can exhibit activity at any of the foregoing temperature and pH ranges suitable for hyperthemophilic acidophile growth and/or survival.

The enzyme or enzymes provided in the composition can be a protease, a lipase, a cellulase, a hemicellulase, a glycoside hydrolase, an endoprotease, a carboxyesterase, an amylase, an alpha-amylase, an endoglucanase, an endopullulanase, a PNGase, a b-glycosideense, a trehalase, a pullulanase, a peptidase, a signal peptidase, a xylanase, a cellobiohydrolase (CBH), a β-glucosidase, a peroxidase, a phospholipase, an esterase, a cutinase, a pectinase, a pectate lyase, a mannanase, a keratinase, a reductase, an oxidase, a phenoloxidase, a lipoxygenase, a ligninase, a tannase, a pentosanase, a malanase, a β-glucanase, an arabinosidase, a hyaluronidase, a chondroitinase, a laccase, a xyloglucanase, a xanthanase, an acyltransferase, a galactanase, a xanthan lyase, a xylanase, an arabinase, a glycohydrolase, a glycosyltransferase, a glycosidase, an endo- or exo-glycosidase and combinations thereof. In some embodiments, the composition comprises a protease and a glycohydrolase. In some embodiments, the composition comprises a protease and a glycosyltransferase. In some embodiments, the composition comprises a protease and a glycohydrolase.

In some embodiments, the enzyme is one that is isolated from a hyperthermophilic or thermophilic organism. In some embodiments, the enzyme is one that is isolated from an acidophilic organism. In some embodiments, the enzyme is isolated from an Archaeal organism that is hyperthermophilic and/or acidophilic. For example, enzymes can be isolated from an organism of the Sulfolobales order, the Thermococcales order, the Thermoproteales order, the Acidilobales order, the Thermoplasmatales order, and the like. In some embodiments, the enzyme is isolated from a bacteria that is hyperthermophilic and/or acidophilic. For example, enzymes can be isolated from an organism of the Actinomycetales order, the Thermales order, the Thermoanaerobacteriales order, the Clostridiales order, the Acidothiobacillales order, the Nitrospirales order, the Rhodospirillales order, and the like. In some embodiments, the enzyme is isolated from a fungi that is hyperthermophilic and/or acidophilic.

In some embodiments, the enzyme is one that can be identified and isolated as described in WO 2014/081973. Enzymes having sequences as described in WO 2014/081973 can also be suitable for use in the compositions disclosed herein. For example, protease enzymes having amino acid sequences as described in WO 2014/081973 (e.g., SEQ ID NOs: 25-35) can be incorporated into the compositions disclosed herein.

2.2. Additives

At least one additive can also be employed for the compositions disclosed herein. For example, an acid may be added in order to reduce the pH to a desired pH range. Suitable acids for use in the compositions include, for example, nitric acid, phosphoric acid, hydrofluoric acid, sulfuric acid, hydrochloric acid, acetic acid, paracetic acid, peroxyacetic acid, citric acid, glycolic acid, lactic acid, formic acid, methane sulfonic acid, alkyl $C_{8-10}$ polyglycolic acid, and mixtures or combinations thereof. The acid can be added in any amount ranging from about 0.1 wt % to 85 wt %, or from about 0.5 wt % to 80 wt 00 or from about 1 wt % to about 75 wt 00 or from about 2.5 wt % to about 70 wt 00 or from about 5 wt % to about 65 wt 00 or from about 10 wt % to about 60 wt 00 or from about 15 wt % to about 55 wt 00 or from about 20 wt % to about 50 wt 00 or from about 25 wt % to about 45 wt 00 or from about 30 wt % to 40 wt %, or any range included between and including any two of these values. For example, the amount of acid can be about 0.1 wt %, 0.25 wt %, 0.5 wt %, 1 wt %, 2.5, wt %, 5 wt %, 7.5 wt %, 10 wt %, 12.5 wt %, 15 wt %, 17.5 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, or any amount included between any two of these values.

In some embodiments, where mixtures or combinations of two or more acids are provided, the total amount of acid can range from about 0.1 wt % to 85 wt %, or from about 0.5 wt % to 80 wt %, or from about 1 wt % to about 75 wt %, or from about 2.5 wt % to about 70 wt 00 or from about 5 wt % to about 65 wt 00 or from about 10 wt % to about 60 wt %, or from about 15 wt % to about 55 wt 00 or from about 20 wt % to about 50 wt 00 or from about 25 wt % to about 45 wt 00 or from about 30 wt % to 40 wt %, or any range included between and including any two of these values. For example, the total amount of acid can be about 0.1 wt %, 0.5 wt %, 1 wt %, 2.5, wt %, 5 wt %, 7.5 wt %, 10 wt %, 12.5 wt %, 15 wt %, 17.5 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, or any amount included between any two of these values. In an exemplary embodiment, the composition can contain about 45% nitric acid and 5% phosphoric acid.

Other additives can also be provided to the composition. In some embodiments, the additives are provided to enhance biopolymer digestion. In some embodiments, the additives are provided to facilitate biopolymer modification. Exemplary additives used in proteomics and biopolymer digestion include, for example, iodoacetamide (IAA), dithiothreitol (DTT), RapiGest SF, PPS Silent® Surfactant, Invitrosol™, ProteaseMAX™, and mixtures or combinations thereof. In some embodiments, a suitable additive can be at least one selected from the group consisting of: poly(oxy-1,2-ethanediyl),alpha-(nonylphenyl)-omega-hydroxy-, dipropylene glycol monomethyl ether, sodium xylene sulfonate, potassium 4-dodecylbenzene sulfonate, triethanolamine dodecylbenzene sulfonate, triethanolamine, hydrogen peroxide, D-glucopyranose (oligomeric, decy octyl glycosides), D-glucopyranose (oligomeric, $C_{10-6}$-alkyl glycosides), sodium formate, sodium hydroxide, tetrasodium EDTA, and water.

In some embodiments, the additive can comprise a solvent such as, for example, an alcohol, alkanol, polyol or a nitrile. The alkanol can be soluble or miscible with water and lipids, and comprises a $C_1$ to $C_{10}$ alkyl group that is straight or branched, substituted or non-substituted. Useful alkanols include short chain alcohols, such as $C_1$-$C_8$ primary, secondary and tertiary alcohols, e.g., methanol, ethanol, n-propanol, iso-propanol, and butanol. Exemplary alkanols include the various isomers of $C_3$ alcohols, particularly iso-propanol. $C_1$-$C_8$ diols can also be used in the alkanol constituent. Nitrile compound such as acetonitrile can be used as the nitrile constituent in aqueous reactions.

The polyol can be an alkylene glycol, such as, for example, glycerol, ethylene glycol, propylene glycol, 1,2-propylene glycol, 1,3-propylene glycol, glycerine, 1,4-butylene glycol and mixtures thereof.

In some embodiments, the additive comprises an antifoam component, such as, for example, a silicone-based anti-foam component.

In some embodiments, the additive includes an alkanolamine selected from the group consisting of monoalkanolamine, dialkanolamine, trialkanolamine, alkylalkanolamine, trialkylamine, triethanolamine and combinations thereof.

In some embodiments, the additive includes a conventional enzyme stabilizing agent, e.g. a polyol such as propylene glycol or glycerol, a sugar or sugar alcohol, a polyamine lactic acid, boric acid, or a boric acid derivative, e.g. an aromatic borate ester, a phenyl boronic acid derivative such as 4-formylphenyl boronic acid.

In some embodiments, the additive includes a chelating agent. The chelating agent can be, for example, a metal ion chelating agent. Metal ion chelating agents can include, for example, copper, iron and/or manganese chelating agents and mixtures thereof. Such chelating agents can be selected from the group consisting of phosphonates, amino carboxylates, amino phosphonates, succinates, polyfunctionally-substituted aromatic chelating agents, 2-pyridinol-N-oxide compounds, hydroxamic acids, carboxymethyl inulins and mixtures thereof. Chelating agents can be present in the acid or salt form including alkali metal, ammonium, and substituted ammonium salts thereof, and mixtures thereof.

Aminocarboxylates chelating agents include, but are not limited to, ethylenediaminetetracetates (EDTA); ethylene glycol tetraacetates (EGTA), N-(hydroxyethyl)ethylenediaminetriacetates (HEDTA); nitrilotriacetates (NTA); ethylenediamine tetraproprionates; triethylenetetraaminehexacetates, diethylenetriamine-pentaacetates (DTPA); methylglycinediacetic acid (MGDA); Glutamic acid diacetic acid (GLDA); ethanoldiglycines; triethylenetetraaminehexaacetic acid (TTHA); N-hydroxyethyliminodiacetic acid (HEIDA); dihydroxyethylglycine (DHEG); ethylenediaminetetrapropionic acid (EDTP), trans-1,2-diamino-cyclohexan-N,N,N',N'-tetraacetic acid (CDTA), nitrilo-2,2',2"-triacetic acid, diethylenetriamine-N,N,N',N',N"-pentaacetic acid, methylamine, histidine, malate and phytochelatin, hemoglobin, chlorophyll, siderophore, pyocyanin, pyoverdin, Enterobactin, peptides and sugars, humic acid, citric acid, water softeners, phosphonates, tetracycline, gadolinium, organophosphorus compound 2,2'-bis(diphenylphosphino)-1,1'-binaphthyl, pentetic acid; N,N-Bis(2-(bis-(carboxymethyl)amino)ethyl)-glycine, N,N-bis (carboxymethyl)glycine, triglycollamic acid; [(Carboxymethyl)imino]bis-(ethylenenitrilo)]-tetraacetic acid), Trilone A, α, α', α"-trimethylaminetricarboxylic acid, tri(carboxymethyl)amine, aminotriacetic acid, Titriplex i, and Hampshire NTA acid, and salts and derivatives thereof.

Phosphorus-containing chelating agents include, but are not limited to, diethylene triamine penta (methylene phosphonic acid) (DTPMP CAS 15827-60-8); ethylene diamine tetra(methylene phosphonic acid) (EDTMP CAS 1429-50-1); 2-Phosphonobutane 1,2,4-tricarboxylic acid (Bayhibit® AM); hexamethylene diamine tetra(methylene phosphonic acid) (CAS 56744-47-9); hydroxy-ethane diphosphonic acid (HEDP CAS 2809-21-4); hydroxyethane dimethylene phosphonic acid; 2-phosphono-1,2,4-Butanetricarboxylic acid (CAS 37971-36-1); 2-hydroxy-2-phosphono-Acetic acid (CAS 23783-26-8); Aminotri(methylenephosphonic acid) (ATMP CAS 6419-19-8); P,P'-(1,2-ethanediyl)bis-Phosphonic acid (CAS 6145-31-9); P,P'-methylenebis-Phosphonic acid (CAS 1984-15-2); Triethylenediaminetetra(methylene phosphonic acid) (CAS 28444-52-2); P-(1-hydroxy-1-methylethyl)-Phosphonic acid (CAS 4167-10-6); bis(hexamethylene triamine penta(methylenephosphonic acid)) (CAS 34690-00-1); N2,N2,N6,N6-tetrakis(phosphonomethyl)-Lysine (CAS 194933-56-7, CAS 172780-03-9), salts thereof, and mixtures thereof. Preferably, these aminophosphonates do not contain alkyl or alkenyl groups with more than about 6 carbon atoms.

A biodegradable chelator that can also be used herein is ethylenediamine disuccinate (EDDS). In some embodiments, the [S,S]isomer as described in U.S. Pat. No. 4,704, 233 can be used. In some embodiments, the trisodium salt of EDDA can be used, though other forms, such as magnesium salts, are also be useful. Polymeric chelating agents such as Triton P® can also be useful.

Polyfunctionally-substituted aromatic chelating agents can also be used in the compositions disclosed herein. Compounds of this type in acid form are dihydroxydisulfobenzenes, such as 1,2-dihydroxy-3,5-disulfobenzene, also known as Tiron. Other sulphonated catechols may also be used. In addition to the disulfonic acid, the term "tiron" can also include mono- or di-sulfonate salts of the acid, such as, for example, the disodium sulfonate salt, which shares the same core molecular structure with the disulfonic acid.

The chelating agent can also include a substituted or unsubstituted 2-pyridinol-N-oxide compound or a salt thereof, can also be provided as a chelating agent. This includes tautomers of the compound, e.g., 1-Hydroxy-2 (1H)-pyridinone, as a chelating agent. In some embodiments, the chelating agent is selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof. In some embodiments, the 1-Hydroxy-2(1H)-pyridinone compound is selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2 (1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof.

Chelating agents can also include hydroxamic acids, which are a class of chemical compounds in which a hydroxylamine is inserted into a carboxylic acid. The general structure of a hydroxamic acid is the following:

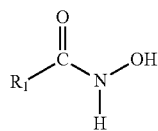

Suitable hydroxamates are those where $R_1$ is $C_4$- to $C_{14}$-alkyl, including normal alkyl, saturated alkyl, salts thereof and mixtures thereof. For example, when the $C_8$-alkyl is present, the compound is called octyl hydroxamic acid.

In some embodiments, the additive can be a stabilizer, such as, for example, a hyaluronic acid stabilizer, a polyvinylpyrrolidone stabilizer, or a polyol stabilizer. Exemplary polyols are disclosed herein and include, for example, propylene glycol and glycerol. In some embodiments, the stabilizer is albumin or a sugar or sugar alcohol, such as, for example, mannitol, trehalose or sorbitol. In some embodiments, the stabilizer is a salt, such as, for example, potassium chloride, magnesium sulfate, and the like. In some embodiments, the stabilizer is an enzyme stabilizer. Any conventional enzyme stabilizer can be used, for example, water-soluble sources of calcium and/or magnesium ions. In some embodiments, the enzyme stabilizer can be a reversible protease inhibitor, such as, for example, a lactic acid or a boron compound. Exemplary boron compounds include, but are not limited to, borate, 4-formyl phenylboronic acid, phenylboronic acid and derivatives thereof. In some embodiments, the enzyme stabilizer can be, but is not limited to, compounds such as calcium formate, sodium formate and 1,2-propane diol.

The additive can be provided in the composition in any amount ranging from about 0.05 wt % to 85 wt %, or from about 0.1 wt % to 80 wt %, or from about 0.5 wt % to about 75 wt 00 or from about 1 wt % to about 70 wt 00 or from about 2.5 wt % to about 65 wt %, or from about 5 wt % to about 60 wt %, or from about 10 wt % to about 55 wt 00 or from about 15 wt % to about 50 wt 00 or from about 20 wt % to about 45 wt %, or from about 25 wt % to 40 wt %, or any range included between and including any two of these values. For example, the amount of additive provided in the composition can be about 0.05 wt %, 0.1 wt %, 0.25%, 0.5 wt %, 1 wt %, 2.5, wt %, 5 wt %, 7.5 wt %, 10 wt %, 12.5 wt %, 15 wt %, 17.5 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, or any amount included between any two of these values.

The composition can include one or more surfactants, which may be an anionic surfactant, a cationic surfactant, a non-ionic surfactant, a semi-polar surfactant, a zwitterionic surfactant, a fatty acid type surfactant, a modified fatty acid surfactant, a polysorbate, an amphoteric surfactant, a polysaccharide surfactant, a silicone emulsion, a hydrotrope, or a mixture thereof.

Exemplary anionic surfactants that can be provided in the compositions disclosed herein include, but are not limited to, sulfates and sulfonates, e.g., linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

Exemplary cationic surfactants that can be provided in the compositions disclosed herein include, but are not limited to, alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

Exemplary non-ionic surfactants that can be provided in the compositions disclosed herein include, but are not limited to, alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN® and TWEEN®, the ethoxylates of alkyl polyethylene glycol ethers, polyalkylene glycol (e.g., 100% Breox FCC92) and alcohol alkoxylate EO/PO (e.g., Plurafac LF403). Exemplary alcohol ethoxylates include fatty alcohol ethoxylates, e.g., tridecyl alcohol alkoxylate, ethylene oxide adduct, alkyl phenol ethoxylates, and ethoxy/propoxy block surfactants, and combinations thereof.

Exemplary semipolar surfactants that can be provided in the compositions disclosed herein include, but are not limited to, amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

Exemplary zwitterionic surfactants that can be provided in the compositions disclosed herein include, but are not limited to, betaine, alkyldimethylbetaine, sulfobetaine, and combinations thereof.

Further non-limiting examples of a surfactant include a fatty acid type surfactant such as caprylic acid (e.g., 100% Prifrac 2912). Non-limiting examples of a modified fatty acid include, e.g., alkyl ($C_{21}$) dibasic fatty acid, Na salt (40%, Diacid H240). Non-limiting examples of a polysorbate include potassium sorbate (e.g., Tween® 20/60/80). Non-limiting examples of an amphoteric surfactant include lauryl dimethyl betaine (e.g., Empigen BB). Non-limiting examples of a polysaccharide surfactant include alkyl $C_8$-$C_{10}$ polyglycoside (e.g., 70% Triton® BG10). Non-limiting examples of a silicone emulsion include a polydimethyl siloxane emulsion (e.g., Dow Corning Antifoam 1510).

A hydrotrope is a compound that dissolves hydrophobic compounds in aqueous solutions. Typically, hydrotropes consist of a hydrophilic part and a hydrophobic part (similar to surfactants) but the hydrophobic part is generally too small to cause spontaneous self aggregation. Exemplary hydrotropes include, but are not limited to, benzene sulfonates, naphthalene sulfonates, alkyl benzene sulfonates, naphthalene sulfonates, alkyl sulfonates, alkyl sulfates, alkyl diphenyloxide disulfonates, and phosphate ester hydrotropes. Exemplary alkyl benzene sulfonates include, for example, isopropylbenzene sulfonates, xylene sulfonates, toluene sulfonates, cumene sulfonates, as well as mixtures any two or more thereof. Exemplary alkyl sulfonates include hexyl sulfonates, octyl sulfonates, and hexyl/octyl sulfonates, and mixtures of any two or more thereof.

Additional exemplary surfactants include, but are not limited to, CHAPS, Big CHAP, CHAPSO, NP-40, sodium dodecyl sulfate (SDS), polysorbate 20 (Tween 20), polysorbate 80 (Tween 80), Triton® X-100, octyl glucoside, octyl thioglucoside, deoxycholate, and mixtures of combinations thereof.

The surfactant can be provided in the composition in any amount ranging from about 0.05 wt % to 85 wt %, or from about 0.1 wt % to 80 wt %, or from about 0.5 wt % to about 75 wt 00 or from about 1 wt % to about 70 wt 00 or from about 2.5 wt % to about 65 wt 00 or from about 5 wt % to about 60 wt 00 or from about 10 wt % to about 55 wt 00 or from about 15 wt % to about 50 wt 00 or from about 20 wt % to about 45 wt 00 or from about 25 wt % to about 40 wt %, or any range included between and including any two of these values. For example, the amount of surfactant provided in the composition can be about 0.05 wt %, 0.1 wt %, 0.25 wt %, 0.5 wt %, 1 wt %, 2.5, wt %, 5 wt %, 7.5 wt %, 10 wt %, 12.5 wt %, 15 wt %, 17.5 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, or any amount included between any two of these values.

In embodiments wherein two or more surfactants are provided in the composition, the total amount of surfactant in the composition can be any amount ranging from about 0.05 wt % to 85 wt %, or from about 0.1 wt % to 80 wt %, or from about 0.5 wt % to about 75 wt %, or from about 1 wt % to about 70 wt %, or from about 2.5 wt % to about 65 wt %, or from about 5 wt % to about 60 wt %, or from about 10 wt % to about 55 wt %, or from about 15 wt % to about 50 wt %, or from about 20 wt % to about 45 wt %, or from about 25 wt % to 40 wt %, or any range included between and including any two of these values. For example, the total amount of surfactant can be about 0.05 wt %, 0.1 wt %, 0.5 wt %, 1 wt %, 2.5, wt %, 5 wt %, 7.5 wt %, 10 wt %, 12.5 wt %, 15 wt %, 17.5 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, or any amount included between any two of these values.

3. Sample Preparation

Also provided herein are methods of preparing a biological sample for analysis, wherein the method comprises: (a) providing the biological sample, (b) contacting the biological sample with a composition comprising an enzyme as disclosed herein, and (c) incubating the mixture comprising the sample and said composition for at least about one (1) second. The methods result in the digestion or modification of at least one protein or biopolymer present in the sample. Modification of the at least one protein or biopolymer present includes, but is not limited to, deglycosylation, reduction of disulfide bonds, methylation, or alkylation at one or more sites in the at least one protein or biopolymer.

The biological sample can be or include any material or matter containing at least one biomolecule of interest. For example, the biological sample can be a tissue, a population of cells, a cell lysate, a cell pellet, a cell culture solution, a biological fluid (e.g., blood, milk, urine, semen), a plant tissue, a plant fluid, a food product, a gel sample, an environmental sample, a medical sample, and the like. The biological sample can be a result of a prior analytical method, such as, for example, an SDS-PAGE gel slice containing a biomolecule of interest.

In some embodiments, the biological sample can be processed or treated prior to contact with the composition comprising the enzyme in step (b). For example, in embodiments wherein the biological sample is a tissue, a population of cells, or a cell culture solution, the cells in the sample can be disrupted or lysed to form a cell lysate or cell extract. Disruption of the cells can be achieved by mechanical, chemical, enzymatic and other means as are commonly known in the art. Mechanical approaches include bead beating, use of pressure such as from a French press and the like, sonication or other methods known in the art. Chemical methods include exposure to chaotropes such as urea, thiourea, or guanidine hydrochloride to lyse the cells and solubilize their contents. In some embodiments, organic acid/solvents mixtures can be utilized to disrupt cells. Enzymatic methods include using lysozyme, lysostaphin or other lytic enzymes to form "holes" in the cell walls that allow the contents to leak out into the surrounding solution. In some embodiments, a chemical or enzymatic agent is contacted with the sample prior to contacting the sample with the composition comprising the enzyme. In some embodiments, a chemical or enzymatic agent is included in the composition comprising the enzyme, and chemical or enzymatic disruption of the cells during step (c) of the sample preparation method.

In some embodiments, the mixture comprising the sample and composition in step (c) is incubated at an incubation temperature that ranges from about 50° C. to about 125° C. In some embodiments, the incubation temperature is about 50° C., 55° C., 60° C., 65° C., 70° C., 75° C., 80° C., 85° C., 90° C., 95° C., 100° C., 105° C., 110° C., 115° C., 120° C., 125° C., or any temperature included between any two of these values. In some embodiments, the incubation temperature is at least about 50° C., 55° C., 60° C., 65° C., 70° C., 75° C., 80° C., or 85° C. In some embodiments, the incubation temperature ranges from about 60° C. to about 100° C. In some embodiments, the incubation temperature ranges from about 70° C. to about 90° C. In some embodiments, the incubation temperature ranges from about 70° C. to about 85° C. In some embodiments, the incubation temperature ranges from about 75° C. to about 85° C. In some embodiments, the incubation temperature ranges from about 75° C. to about 80° C.

In some embodiments, the mixture comprising the sample and composition in step (c) is incubated at a pH of from about 0.5 to about 4.5, or from about 0.5 to about 3.0, or from about 0.5 to about 1.5, or any pH range included between and including any two of these values. In some embodiments, the mixture in step (c) is incubated at a pH of about 2.0 to 3.0. In some embodiments, the mixture in step (c) is incubated at a pH of from about 4 to about 7, or from about 4.5 to about 6.5, or from about 5 to about 6, or any pH range included between and including any two of these values. In some embodiments, the mixture in step (c) is incubated at a pH of about 5.5. In some embodiments, the mixture in step (c) is incubated at a pH of about 3.0.

In some embodiments, the mixture comprising the sample and composition in step (c) is incubated in the presence of an additive as disclosed herein. For example, the additive can be an acid, a protein or biopolymer digestion additive, a solvent, an anti-foam component, an enzyme stabilizing agent, a chelating agent, a stabilizer, a surfactant, a hydrotrope, and the like as described herein. In some embodiments, the additive is provided in any amount ranging from about 0.05 wt % to 85 wt %, or from about 0.1 wt % to 80 wt %, or from about 0.5 wt % to about 75 wt %, or from about 1 wt % to about 70 wt %, or from about 2.5 wt % to about 65 wt %, or from about 5 wt % to about 60 wt %, or from about 10 wt % to about 55 wt %, or from about 15 wt % to about 50 wt %, or from about 20 wt % to about 45 wt %, or from about 25 wt % to 40 wt %, or any range included between and including any two of these values. For example, the amount of additive provided in the composition can be about 0.05 wt %, 0.1 wt %, 0.25%, 0.5 wt %, 1 wt %, 2.5, wt %, 5 wt %, 7.5 wt %, 10 wt %, 12.5 wt %, 15 wt %, 17.5 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, or any amount included between any two of these values, wherein the weight percentages are based on the total weight of sample and composition. In some embodiments, the additive is provided in any amount ranging from about 0.05% (v/v) to 85% (v/v) or from about 0.1% (v/v) to 80% (v/v), or from about 0.5% (v/v) to about 75% (v/v), or from about 1% (v/v) to about 70% (v/v), or from about 2.5% (v/v) to about 65% (v/v), or from about 5% (v/v) to about 60% (v/v), or from about 10% (v/v) to about 55% (v/v), or from about 15% (v/v) to about 50% (v/v), or from about 20% (v/v) to about 45% (v/v), or from about 25% (v/v) to 40% (v/v), or any range included between and including any two of these values. For example, the amount of additive provided in the composition can be about 0.05 wt %, 0.1% (v/v), 0.25%, 0.5% (v/v), 1% (v/v), 2.5,% (v/v), 5% (v/v), 7.5% (v/v), 10% (v/v), 12.5% (v/v), 15% (v/v), 17.5% (v/v), 20% (v/v), 25% (v/v), 30% (v/v), 35% (v/v), 40% (v/v), 45% (v/v), 50% (v/v), 55% (v/v), 60% (v/v), 65% (v/v), 70% (v/v), 75% (v/v), 80% (v/v), 85% (v/v), or any amount included between any two of these values, wherein the (v/v) percentages can be based on the total volume of sample and composition.

In some embodiments, the method results in at least about 5% digestion of a protein or biopolymer in the sample. In some embodiments, the method results in at least about 10%, 15%, 20%, 25%, 30%, 35%, 40%, 45%, 50%, 55%, 60%, 65%, 70%, 75%, 80%, 85%, 90%, or 95% digestion of a protein or biopolymer in the sample. In some embodiments, the method results in at least about 10% digestion of a protein or biopolymer in the sample. In some embodiments, the method results in at least about 15% digestion of a protein or biopolymer in the sample. In some embodiments, the method results in at least about 20% digestion of a protein or biopolymer in the sample. In some embodiments, the method results in at least about 25% digestion of a protein or biopolymer in the sample. In some embodiments, the method results in at least about 30% digestion of a protein or biopolymer in the sample. In some embodiments, the method results in at least about 35% digestion of a protein or biopolymer in the sample. In some embodiments, the method results in at least about 40% digestion of a protein or biopolymer in the sample. In some embodiments, the method results in at least about 45% digestion of a protein or biopolymer in the sample. In some embodiments, the method results in at least about 50% digestion of a protein or biopolymer in the sample. In some embodiments, the method results in at least about 55% digestion of a protein or biopolymer in the sample. In some embodiments, the method results in at least about 60% digestion of a protein or biopolymer in the sample. In some embodiments, the method results in at least about 65% digestion of a protein or biopolymer in the sample. In some embodiments, the method results in at least about 70% digestion of a protein or biopolymer in the sample. In some embodiments, the method results in at least about 75% digestion of a protein or biopolymer in the sample. In some embodiments, the method results in at least about 80% digestion of a protein or biopolymer in the sample. In some embodiments, the method results in at least about 85% digestion of a protein or biopolymer in the sample. In some embodiments, the method results in at least about 90% digestion of a protein or biopolymer in the sample. In some embodiments, the method results in at least about 95% digestion of a protein or biopolymer in the sample. In some embodiments, the method results in about 100% digestion of a protein or biopolymer in the sample. The percent digestion can be measured on a (w/w) basis or a mass/mass basis.

Incubation of the mixture comprising the sample and the composition in step (c) can be for any duration of time ranging from about 5 minutes to about 30 days. The duration of time for the incubation period can be any amount of time as along as the enzyme remains active. In some embodiments, the sample and the composition in step (c) are incubated for a duration of time ranging from about 5 minutes to about 300 minutes, or from about 10 minutes to about 150 minutes, or from about 15 minutes to about 120 minutes, or from about 20 minutes to about 90 minutes, or from about 30 minutes to about 75 minutes, or from about 40 minutes to about 60 minutes, or any range included between and including any two of these values. In some embodiments, incubation of the sample and the composition in step (c) can be for any duration of time ranging from about 1 second to about 120 minutes, or from about 30 seconds to about 100 minutes, or from about 1 minute to about 90 minutes, or from about 10 minutes to about 75 minutes, or from about 30 minutes to about 60 minutes, or any range included between and including any two of these values.

In some embodiments, the mixture comprising the sample and the composition in step (c) is incubated for less than about eight hours. In some embodiments, the mixture in step (c) is incubated for less than about four hours. In some embodiments, the mixture in step (c) is incubated for less than about 120 minutes. In some embodiments, the mixture in step (c) is incubated for less than about 90 minutes. In some embodiments, the mixture in step (c) is incubated for less than about 60 minutes. In some embodiments, the mixture in step (c) is incubated for less than about 45 minutes. In some embodiments, the mixture in step (c) is incubated for less than about 30 minutes. In some embodiments, the mixture in step (c) is incubated for less than about 15 minutes. In some embodiments, the mixture in step (c) is incubated for less than about 10 minutes. In some embodiments, the mixture in step (c) is incubated for a duration of time of less than about 5 minutes. In some embodiments, the mixture in step (c) is incubated for a duration of time of less than about 1 minute. In some embodiments, the mixture in step (c) is incubated for a duration of time of less than about 30 seconds. In some embodiments, the mixture in step (c) is incubated for a duration of time of less than about 10 seconds. In some embodiments, the mixture in step (c) is incubated for a duration of time of less than about 5 seconds.

In some embodiments, the mixture comprising the sample and the composition in step (c) is incubated for less than about 5 minutes. For example, the mixture in step (c) can be incubated for about 1 second, about 2 seconds, about 5 seconds, about 10 seconds, about 15 seconds, about 20 seconds, about 30 seconds, about 60 seconds, about 90 seconds, about 120 seconds, for about 3 minutes, or for about 4 minutes.

In some embodiments, the mixture comprising the sample and the composition in step (c) is incubated for a duration of time ranging from about 12 hours to about 7 days, or from about 24 hours to about 6 days, or from about 36 hours to about 5 days, or from about 48 hours to about 4 days. In some embodiments, the mixture in step (c) can be incubated for a duration of time ranging from about 12 hours to about 24 hours. In some embodiments, the mixture in step (c) can be incubated for a duration of time ranging from about 24 hours to about 36 hours. In some embodiments, the mixture in step (c) can be incubated for a duration of time ranging from about 24 hours to about 48 hours. In some embodiments, the mixture in step (c) can be incubated for a duration of time ranging from about 48 hours to about 6 days. In some embodiments, the mixture in step (c) can be incubated for a duration of time ranging from about 72 hours to about 5 days.

In some embodiments, the mixture comprising the sample and the composition in step (c) are incubated for a duration of time ranging from about 1 day to about 30 days, or from about 5 days to about 25 days, or from about 10 days to about 20 days. In some embodiments, the mixture in step (c) are incubated for a duration of time ranging from about 15 days to about 30 days, In some embodiments, the mixture in step (c) can be incubated for about 10, 11, 12, 13, 14, 15, 16, 17, 18, 19, or 20 days. In some embodiments, the mixture in step (c) can be incubated for about 21, 22, 23, 24, 25, 26, 27, 28, 29, or 30 days.

In some embodiments, the method further comprises a step (c)(i) of adjusting the pH of the mixture comprising the sample and the composition. In some embodiments, the pH of the mixture is adjusted to a range of about 4.5 to about 10.0. In some embodiments, the pH of the mixture is adjusted to a range of about 5.0 to about 10.0. In some embodiments, the pH of the mixture is adjusted to a range of about 7.0 to about 10.0. In some embodiments, the pH of the mixture is adjusted to about 7.5, 8.0, 8.5, 9.0, 9.5, or 10.0. The step of adjusting the pH of the mixture results in a decrease of the enzymatic activity of the composition and can be achieved by, for example, adding a sufficient amount of base, aqueous solution, or water to the mixture.

In some embodiments, the method further comprises a step (c)(ii) comprising adjusting the temperature of the mixture to a temperature ranging from about 4° C. to about 37° C. In some embodiments, the temperature of the mixture is adjusted to about 4° C. In some embodiments, the temperature of the mixture is adjusted to about 10° C. In some embodiments, the temperature of the mixture is adjusted to about 12° C. In some embodiments, the temperature of the mixture is adjusted to about 15° C. In some embodiments, the temperature of the mixture is adjusted to about 20° C. In some embodiments, the temperature of the mixture is adjusted to about 25° C. In some embodiments, the temperature of the mixture is adjusted to about 30° C. In some embodiments, the temperature of the mixture is adjusted to about 32° C. In some embodiments, the temperature of the mixture is adjusted to about 35° C. In some embodiments, the temperature of the mixture is adjusted to about 37° C.

In some embodiments, the step of adjusting the pH of the mixture (step (c)(i)) and/or adjusting the temperature of the mixture (step c(ii)) results in a reduction in enzymatic activity of the composition. For example, adjusting the pH of the mixture (step (c)(i)) and/or adjusting the temperature of the mixture (step c(ii)) can result in a decrease by about 25%, 30%, 35%, 40%, 45%, 50%, 55%, 60%, 65%, 70%, 75%, 80%, 85%, 90%, 95% or 100% of enzymatic activity relative to baseline (e.g., enzymatic activity prior to the steps (c)(i) and (c)(ii)). In some embodiments, adjusting the pH of the mixture (step (c)(i)) and/or adjusting the temperature of the mixture (step c(ii)) can result in a decrease of at least about 25%, 30%, 35%, 40%, 45%, 50%, 55%, 60%, 65%, 70%, 75%, 80%, 85%, 90%, 95%, 98% or 99% of enzymatic activity relative to baseline. In some embodiments, carrying out step (c)(i) and/or (c)(ii) can result in a 100% decrease of enzymatic activity relative to baseline. In some embodiments, carrying out step (c)(i) and/or (c)(ii) can result in complete elimination of enzymatic activity relative to baseline. In some embodiments, step (c)(i) is carried out to reduce enzymatic activity as disclosed herein. In some embodiments, step (c)(ii) is carried out to reduce enzymatic activity as disclosed herein. In some embodiments, steps (c)(i) and (c)(ii) are carried out to reduce enzymatic activity as disclosed herein.

In some embodiments, steps (a) to (c) (including (c)(i) and (c)(ii), if undertaken), are carried out in a single vessel or container.

In some embodiments, subsequent to step (c), (c)(i), and/or (c)(ii), the mixture is further treated to remove contaminants. In some embodiments, subsequent to step (c), (c)(i), and/or (c)(ii), the mixture, or a portion thereof, is directly analyzed for proteomic, glycomic, glycoproteomic analysis. For example, in some embodiments, subsequent to step (c), (c)(i), and/or (c)(ii), the mixture, or a portion thereof, is injected into a mass spectrometer device for analysis.

In some embodiments, subsequent to step (c), (c)(i), and/or (c)(ii), the mixture undergoes a treatment step (d) that allows removal of contaminants and sample clean-up for subsequent analysis by mass spectrometry. The treatment step (d) results in removal of salts or lipids from the crude cell lysate or extract, removal of organic solvents and/or chemical additives in in the mixture, and enrichment of one or more analytes of interest (e.g. a digested protein or biopolymer) relative to one or more other components of the sample.

In some embodiments, treatment of the mixture in step (d) comprises removing one or more contaminants by filtration of ultrafiltration. Filtration and ultrafiltration techniques are known to those of skill in the art, e.g., as described by Ivanov and Lazarev (2011. *Sample preparation in biological mass spectrometry*. Dordrecht: Springer, xxix, 1089 pages).

In some embodiments, treatment of the mixture in step (d) comprises removing one or more contaminants by selective precipitation. In some embodiments, the selective precipitation is carried out by acetone precipitation, trichloroacetic acid (TCA) precipitation, chloroform-methanol precipitation, and/or ethyl acetate precipitation. Selective precipitation techniques are known in the art, and can be carried out in accordance with protocols described, for example, in Ivanov and Lazarev (2011. *Sample preparation in biological mass spectrometry*. Dordrecht: Springer, xxix, 1089 pages).

In some embodiments, treatment of the mixture in step (d) comprises removing one or more contaminants by chromatography. Chromatographic separation methods include one or more of ion exchange, size exclusion, hydrophobic liquid interaction chromatography (HILIC), hydrophobic interaction, affinity, normal-phase, or reverse-phase chromatography. In some embodiments, chromatography is carried out using a chromatography column that is configured for at least partial chromatographic separation and isolation of the digested proteins or biopolymer in the sample. The stationary phase in the chromatography column can be porous or non-porous silica or agarose particles, or a monolithic material polymerized or otherwise formed inside the column. The stationary phase can be coated with an appropriate material such as C18, C8, C4 or another suitable derivative, or contain cation exchanger or other material, or the combination of the above to facilitate the separation of the proteins, and such material may be chemically bonded to the particles or monolith inside the column. Particle sizes typically range from about 1.5 µm to 30 µm. Pore sizes can range from 50 to 300 angstroms. Inside diameters of columns typically range from about 50 µm to 2.1 mm, and column length from about 0.5 cm to 25 cm or longer. In some embodiments, the mobile phase or eluent can be a pure solvent, or a mixture of two or more solvents, and may contain added salts, acids and/or other chemical modifiers. In some embodiments, the proteins are separated on the column based on one or more physiochemical properties, including size, net charge, hydrophobicity, affinity, or other physiochemical properties. In some embodiments, the chromatography technique comprises high-performance liquid chromatography (HPLC). In some embodiments, the chromatography process comprises ultra-performance liquid chromatography (UPLC). Chromatography, HPLC, and UPLC techniques are known in the art and are described, for example, in Ivanov and Lazarev (2011. *Sample preparation in biological mass spectrometry*. Dordrecht: Springer, xxix, 1089 pages).

In some embodiments, treatment of the mixture in step (d) comprises removing one or more contaminants by a sample-purification device, such as, for example, a solid phase extraction (SPE) cartridge. In some embodiments, the SPE cartridge is in line directly with the high resolution/accurate mass instrument. In some embodiment, the SPE cartridge is a polypropylene tip with a small volume of silica or other sorbent containing bonded C4, C8, C18, RP4H, or RPSH or other functional groups immobilized in the cartridge, for example, a StageTip™ cartridge (Thermo Fisher Scientific). In some embodiments, polymeric sorbents or chelating agents are used. The bed volume can be as small as 1 µL or less but greater volumes are also contemplated. In some embodiments, the SPE cartridge is used once.

In some embodiments, treatment of the mixture in step (d) can include one or more of the techniques described supra. For example, in some embodiments, the treatment step (d) can comprise a filtration step and a selective precipitation step. In some embodiments, the treatment step (d) can comprise a filtration step and a chromatography step. In some embodiments, the treatment step (d) can comprise a selective precipitation step and a chromatography step. In some embodiments, the treatment step (d) can comprise a filtration step, a selective precipitation step, and a chromatography step. The filtration step, selective precipitation step, and chromatography step can be carried out in any sequence order. Treatment of the mixture in step (d) typically results in sufficient removal of one or more contaminants such that digested protein or biopolymer in the prepared sample is suitable for analysis, e.g., by mass spectrometry. For example, treatment of the mixture in step (d) can provide sufficient removal of one or more contaminants such that the one or more contaminants is undetectable or provides minimal interference during analysis of the sample.

In some embodiments, the method further comprises a step (e) of drying the mixture. In some embodiments, step (e) results in removal of about 85%, 90%, 95%, 96%, 97%, 98%, 99%, or 99.5% of the liquid in the mixture. Drying the mixture can be carried out by placing the sample at an elevated temperature (≥37° C.) and/or under vacuum. In some embodiments, drying the mixture can be carried out by lyophilization.

In some embodiments, subsequent to any of steps (c) (e.g., subsequent to step (c), step (c)(i), step (c)(ii)), step (d), and/or step (e)), the method further comprises storing the mixture containing the prepared sample for a duration of time ranging from about 30 days to about 10 years. In some embodiments, the mixture is stored for at least about 30 days. In some embodiments, the mixture is stored for at least about 45 days. In some embodiments, the mixture is stored for at least about 60 days. In some embodiments, the mixture is stored for at least about 90 days. In some embodiments, the mixture is stored for at least about six months. In some embodiments, the mixture is stored for at least about a year. Storage conditions include temperatures ranging from about −70° C. to room temperature (approximately 25° C. to 28° C.).

4. Common Applications

The compositions and methods of using the same for sample preparation as disclosed herein can be applied to any type of analytical method, including, but not limited to mass spectrometry-based proteomic analysis, glycomic analysis, glycoproteomic analysis, lipomic analysis, amino acid analysis, enzymatic assay, and immunochemical assay, among other biological and biochemical analyses.

In some embodiments, the compositions and methods of sample preparation disclosed herein are directed to use in mass spectometry based proteomics. There are two main approaches for mass spectrometry-based proteomics, top-down and bottom-up analyses. Top-down methods analyze whole proteins, while bottom-up approaches investigate the peptides from digested proteins. The compositions and methods disclosed herein have broad applicability to bottom-up approaches for analysis but are not limited to bottom-up approaches. In some embodiments, the compositions and methods disclosed herein can be used in further evaluation of a biological sample after top-down analysis has taken place. The sample is contacted with a composition comprising In some embodiments, the compositions and methods of sample preparation disclosed herein are directed to use in immunochemical analysis. In some embodiments, a composition comprising a protease is contacted with the sample for analysis by immunochemistry. In some embodiments, a composition comprising a protease and a glycohydrolase is contacted with the sample for analysis by immunohistochemistry.

5. Kits

Also provided herein are kits for preparing or digesting analytical samples, wherein the kit comprises: an enzyme or enzyme mixture, an acid, optionally one or more additives, and instructions for their use. The enzyme or enzyme mixture can be a thermophilic, hyperthermophilic and/or acidophilic enzyme as described herein. The acid and optional additive can be any acid and additive as disclosed herein.

In some embodiments, the enzyme or enzyme mixture is provided as a lyophilized product, which can optionally be provided with a diluent. In some embodiments, the enzyme or enzyme mixture is provided as a suspension. In some embodiments, the enzyme or enzyme mixture is provided as a solution. In some embodiments, the enzyme or enzyme mixture is provided in one container, and the optionally provided diluent is provided in a second, separate container. In some embodiments, instructions for preparing the enzyme or enzyme mixture in the optionally provided diluent are provided.

In some embodiments, the enzyme or enzyme mixture, the acid and the optional additive(s) are provided in separate, individual containers. In some embodiments, the enzyme (or enzyme mixture) and the acid are provided in the same container, and the optional additive(s) are provided in a separate container. In some embodiments, the acid and optional additive(s) are provided in the same container, and the enzyme (or enzyme mixture) is provided in a separate container.

In some embodiments, the kit comprises a microfluidics apparatus, and the enzyme or enzyme mixture is immobilized on a structure that forms part of the apparatus. In such embodiments, a sample can be provided to the apparatus and digested, cleaved, or otherwise prepared for analysis during in-line flow as part of the upstream fluidics of an analyzer, e.g., a mass spectrometer.

In some embodiments, the kit comprises an enzyme mixture comprising an ultrastable enzyme and at least one mesophilic enzyme. Temporally-distinct digestions of the sample can be carried out by sequentially incubating the enzyme mixture and sample at a first temperature at which the at least one mesophilic enzyme is optimally active, followed by incubation at a second temperature at which the ultrastable enzyme is optimally active, optionally followed by incubation at one or more sequential temperatures in which each sequential temperature corresponds to a temperature at which one or more additional ultrastable enzymes is optimally active. Such "thermal switching" allows multiple sequential activities to be applied to a single sample separated by time using a single formulation and segmented temperature incubations to control the respective activities.

In some embodiments, the kits can be stored at ambient (about 20° C.-25° C.) temperatures. In some embodiments, the kits can be stored at about 4° C. In some embodiments, the kits can be stored at temperatures of from about 4° C. to about 20° C. In some embodiments, the kits can be stored at temperatures of up to about 30° C.

In some embodiments, the kits have a storage shelf-life of at least about three months. In some embodiments, the kits have a storage shelf-life of at least about six months. In some embodiments, the kits have a storage shelf-life of at least about nine months. In some embodiments, the kits have a storage shelf-life of at least about 12 months, 18 months, 24 months, 30 months or 3 years.

EXAMPLES

Example 1

Production of Candidate Ultrastable Enzymes

Potentially useful gene sequences were identified using standard bio-informatics approaches. Genes of interest were isolated and cloned using standard molecular biology techniques according to a scheme similar to those disclosed in WO 2014/081973, which is incorporated herein by reference in its entirety. Functional enzymes were produced by recombinant expression in hyperthermophilic and acidophilic microbes of the domain Archaea of the order Sulfolobales. Transformed microbes were cultured at 80° C. and pH=3.0, and culture medium included carbon, nitrogen, phosphorous, and sulfur sources and trace minerals. Genetic constructs of genes of interest were designed to target gene products to the extracellular space using localization sequences similar to those described previously (WO 2014/081973). Recombinant enzymes accumulated in the culture media and were concentrated and buffer exchanged using commercially available tangential flow filtration devices. In some embodiments, enzymes were designed to have an epitope, a poly-histidine fusion (e.g., a histidine tag) or another useful modification to facilitate purification and/or characterization. Enzymes were concentrated 200-10,000× from the original solution and filter sterilized and stored at room temperature, −20° C., −80° C. or lyophilized. Further chromatographic purifications are carried out for each individual enzyme to >99% homogeneity for the activity of interest.

Enzymes suitable for acidic pH environments have at least 25% of their maximum activity at pH values ranging from about 0.5 to 4.5. Exemplary optimum activities range from about pH 2.5 to 3.5. Enzymes suitable in neutral pH environments have at least 25% of their maximum activity pH values ranging from about 4 to 7. Exemplary optimum activity for such an enzyme can be at about pH 5.5.

Enzymes suitable for hyperthermophilic environments have at least 25% of their maximum activity at temperatures ranging from about 70° C. to about 110° C. Exemplary optimum activities range can be from about 70° C. to about 90° C., or from about 75° C. to about 85° C., or at about 80° C.

Example 2

Characterization of Ultrastable Protease Enzymes

Three exemplary proteases were purified and assayed for enzymatic activity over a range of pH and temperature values. Enzymatic activity was assayed by standard protease assay holding one parameter at a fixed value while varying the values of the other parameter. Operational ranges were defined by ≥50% maximal activity. Approximate optimal temperatures, pH, and half-life were measured and are indicated in FIG. 1.

Figure 2:
FIG. 2 includes protease zymograms of two purified acid-, heat-, and detergent-stable proteases using a gelatin-impregnated SDS-PAGE (1% sodium dodecyl sulfate, SDS) incubated after electrophoresis at pH 3.0 in dilute acid at 80° C. for 30 minutes.

Two of the proteases were further analyzed for detergent, acid, and thermal stability by assessing different mobility patterns on a gelatin-impregnated SDS-PAGE (1% SDS). The SDS-PAGE gel was incubated after electrophoresis at pH 3.0 in dilute acid at 80° C. for 30 minutes. As illustrated in FIG. 2, protease activity is visible as a white bands or smears against the blue background, which indicates digestion of gelatin protein impregnated throughout the gel matrix. FIG. 2 thus illustrates retained protease activity at acidic pH (3.0) and elevated temperature (80° C.) after exposure to SDS during the running of the gel, for the assayed protease enzymes, indicating detergent, acid, and thermal stability of the enzymes.

Example 3

Comparison of Exemplary Enzymes to Commercial Formulations

Figure 8:
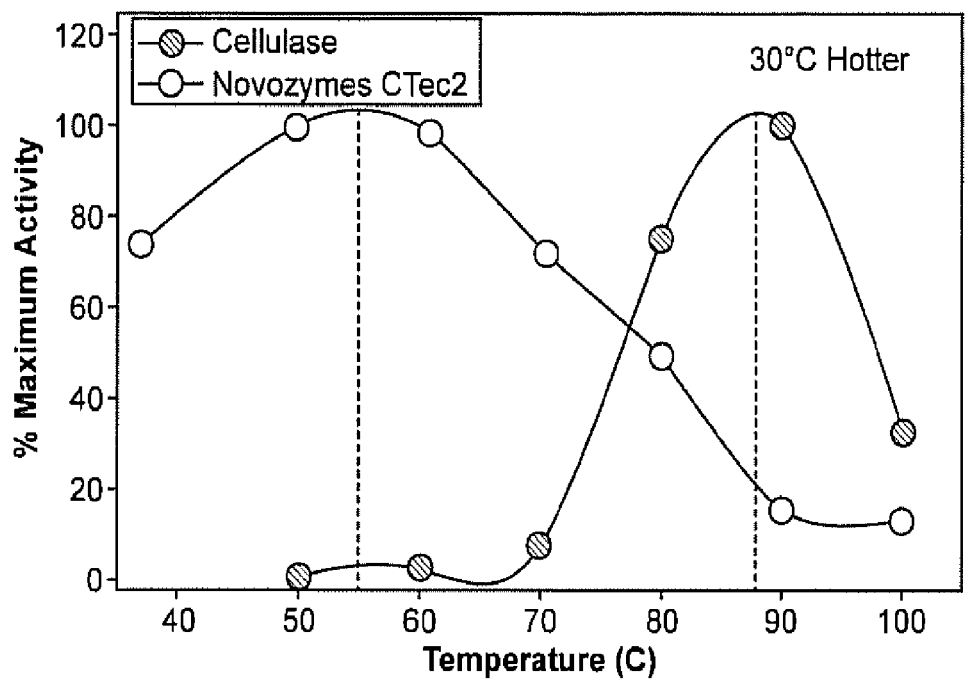
FIG. 8 is a graph illustrating head-to-head comparison of the heat and acid compatibility for a single exemplary ultrastable cellulase disclosed herein compared to market leading cellulase formulation of a mix of enzymes that has been optimized for acid and heat stability.
Figure 8:
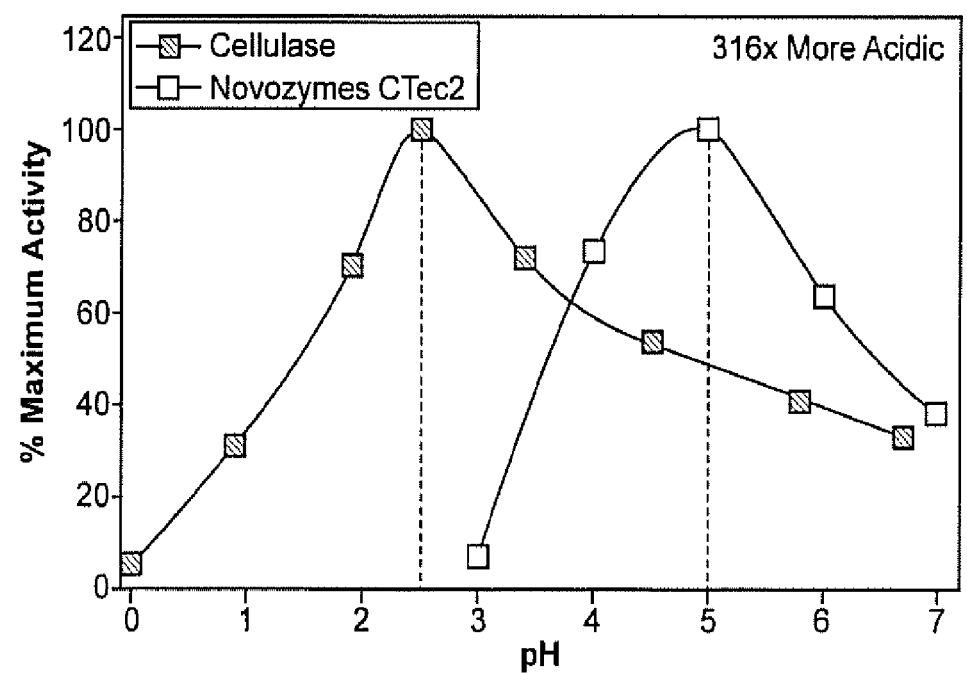

The enzymes disclosed herein were compared to commercially available formulations (e.g., Novozymes CTec2) that were optimized for acid and heat stability over many years. In the comparison study, the enzymes described herein significantly outperformed the commercial formulations (FIG. 8). For example, it was observed that the ultrastable cellulase optimal activity occurs at a temperature that is 30° C. higher than that of comparable commercially available cellulase enzymes. In addition, it was observed that the ultrastable cellulase functioned optimally in a pH range that is >300× more acidic (by about 2.5 pH units) than the functional pH range of commercially available comparators.

Example 4

Evaluation of Proteases for Sample Preparation (Ms-Based Proteomic Analysis)

Figure 3:
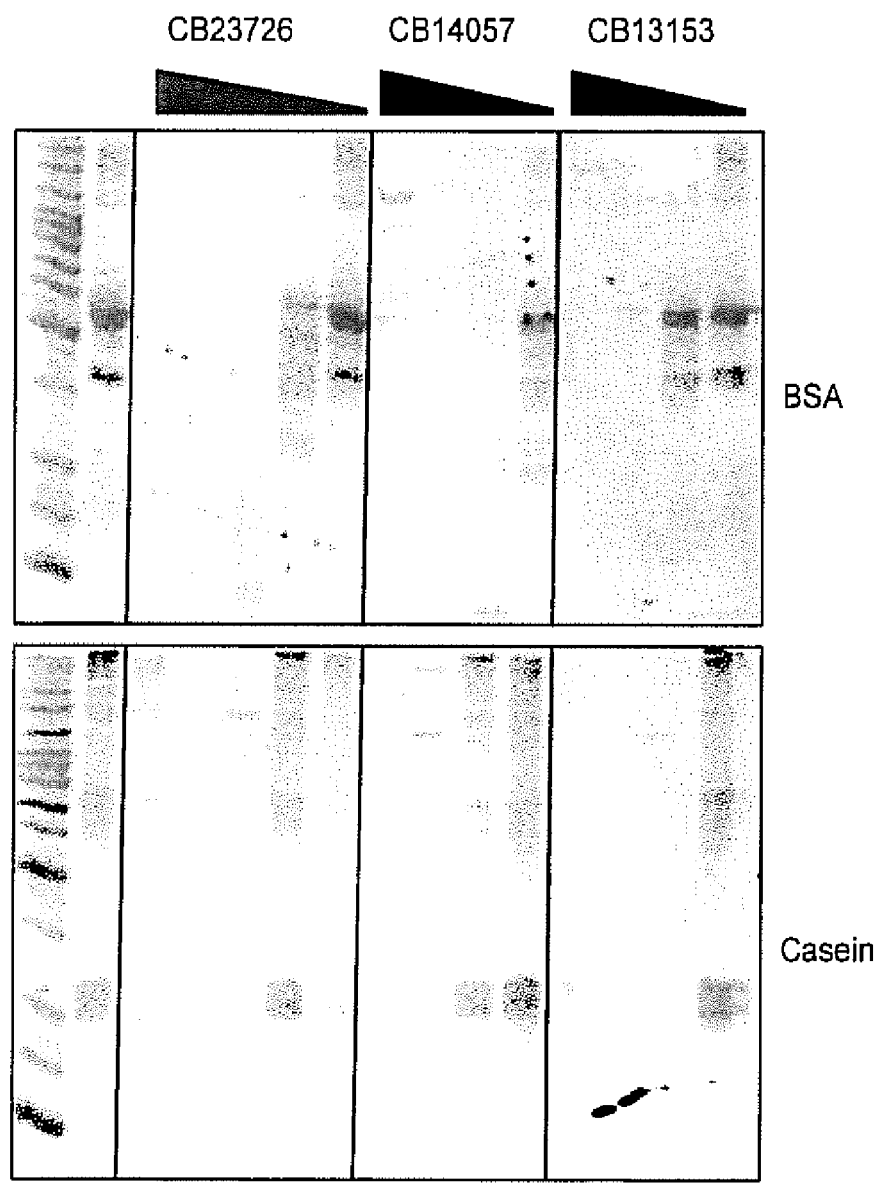
FIG. 3 includes representative Coomassie blue stained SDS-PAGE gels of BSA and Casein reactions with exemplary proteases in a log (×0.1) dilution series.
Figure 4:
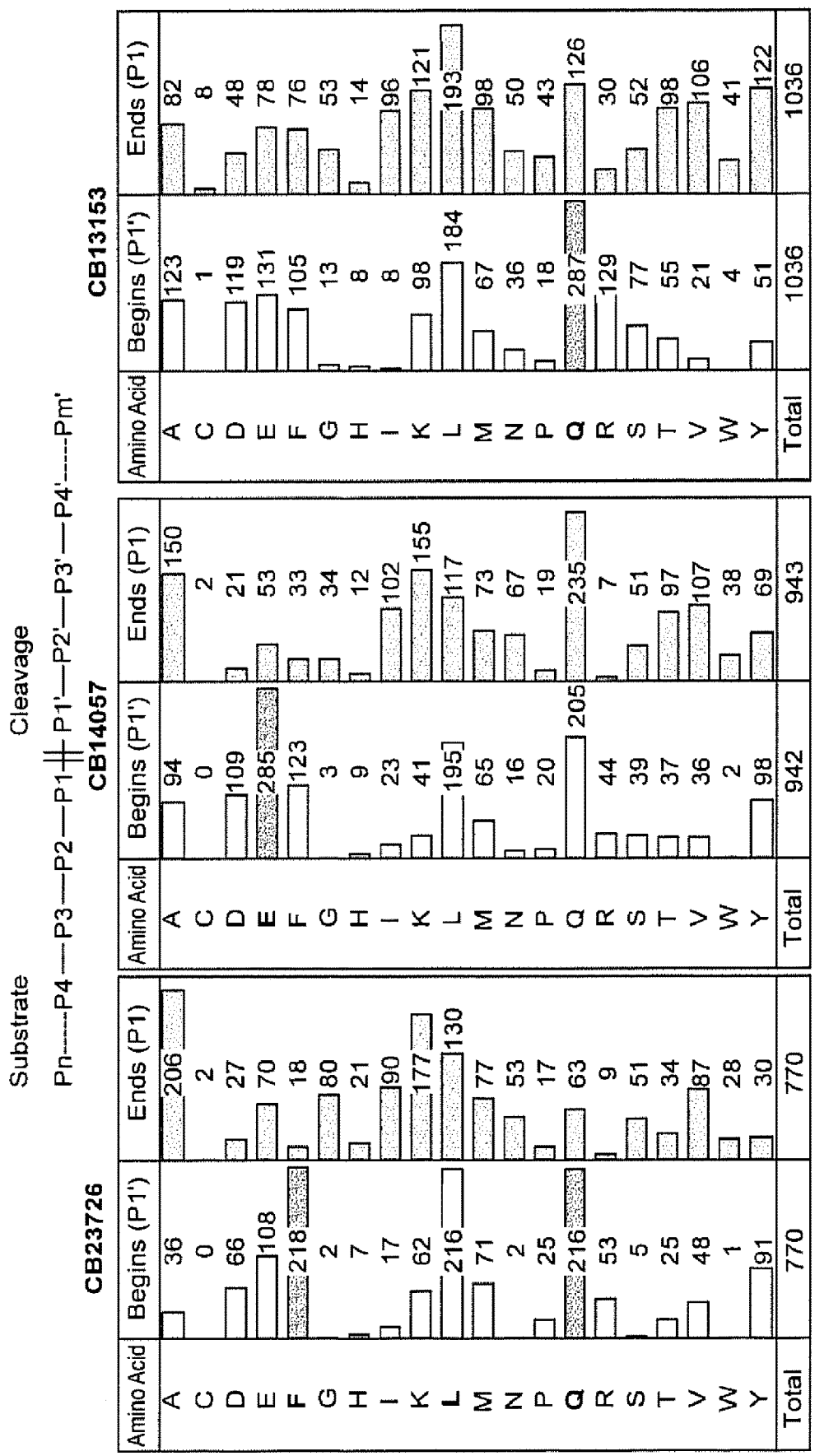
FIG. 4 illustrates peptide analyses of proteolytic cleavage of casein and BSA reactions by acid- and heat-stable proteases.

Experiments were conducted to apply hyper-heat and acid stable proteases to in-solution digestions of common proteins for proteomic analysis. Due to the large amount of available proteomics data for BSA, casein, myoglobin and ovalbumin, preliminary proteomics analyses of digestion of BSA and casein with three candidate proteases were carried out (FIG. 3). Each protease enzyme was incubated with BSA or casein for 1 hour at pH 3.0 in dilute acid at 80° C. A representative reaction was selected form each series, and the products were analyzed by tandem mass spectrometry to identify the resulting peptides. FIG. 4 illustrates the peptide analysis of proteolytic cleavage of casein and BSA by the proteases. Approximately 1000 peptide ions were scored for each digestion to preliminarily map the cleavage pattern of the respective proteases on BSA and casein. The number of peptide ions identified with the indicated amino acids at the P1 and P1' locations are indicated in FIG. 4. FIG. 5 includes a table summarizing the results of the peptide mapping and cleavage specificity of the tested proteases.

The results suggested that one candidate protease is pepsin-like. In contrast, the other two candidate proteases showed novel cleavage specificity (not all data shown). Additional research is needed to further characterize the candidate proteases, including identification of key parameters for in-solution digests including; coverage statistics, cleavage specificity, and signal intensities (digestion efficiencies) and benchmarking against commercial trypsin protocols for mass spectrometry.

Example 5

Compatibility of Non-Protease Ultrastable Enzymes with Ultrastable Protease Enzymes Non-protease ultrastable enzymes were incubated with ultrastable protease enzymes to determine sensitivity of the non-protease ultrastable enzymes to degradation by the ultrastable protease enzymes.

Figure 6:
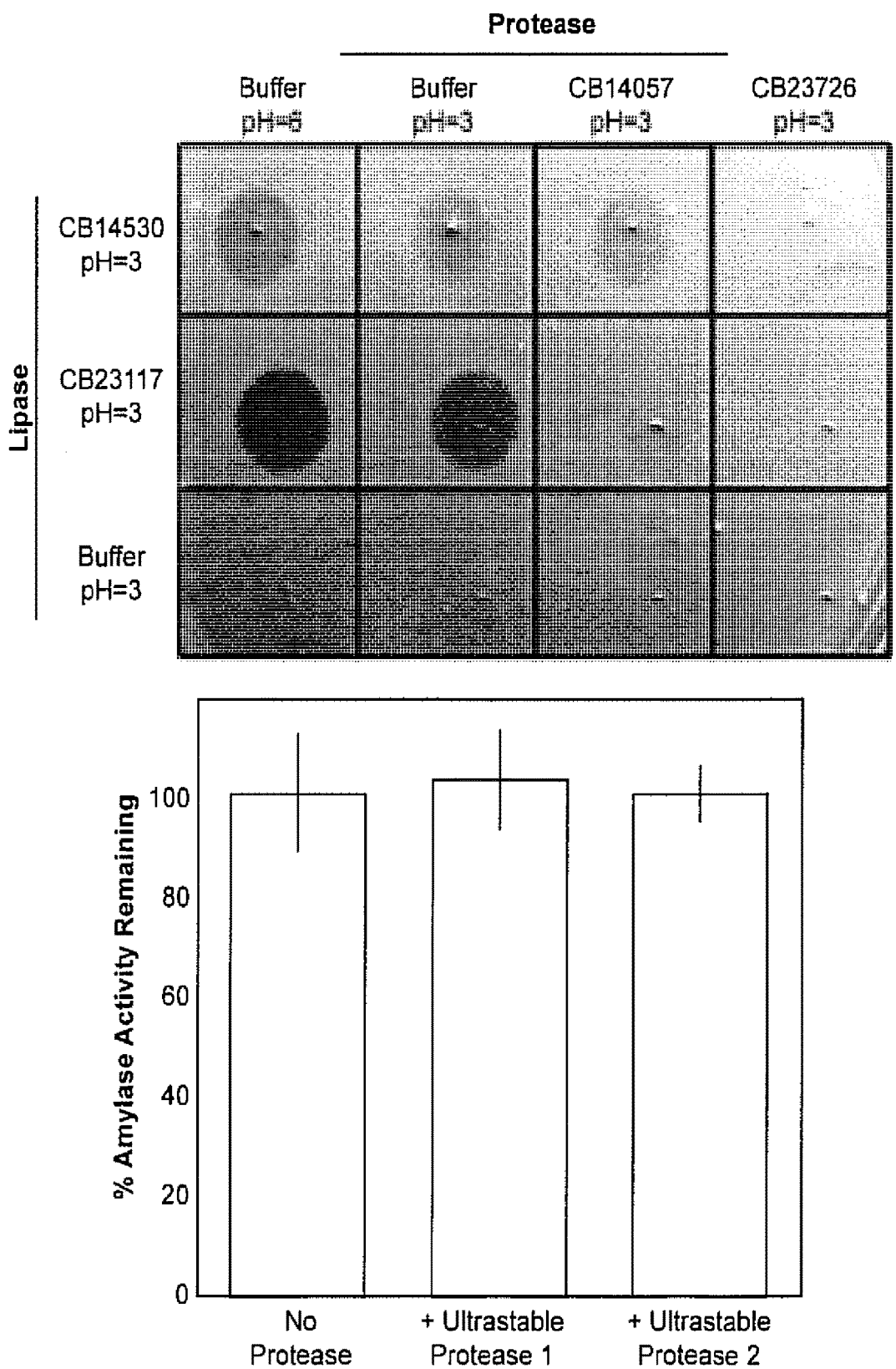
FIG. 6 illustrates the compatibility of non-protease ultrastable enzymes with ultrastable proteases.

In a first experiment, unique combinations of an ultrastable lipase enzyme mixed with an ultrastable protease enzyme were spotted on a gellan gum plate containing a biological fat in the form of a triacylglycerol (tributyrin) emulsion with a pH of 3.0. The plate was then incubated at 80° C. for 60 minutes. As illustrated in FIG. 6 (top panel), three of the protease/lipase combinations illustrated lipase sensitivity to degradation by the protease, while one combination illustrated lipase stability in the presence of protease (top row, third column).

In a second experiment, an ultrastable amylase enzyme was incubated in the presence or absence of one of two ultrastable proteases, and activity of the amylase enzyme was monitored for one hour at the optimal conditions for each protease. Activity was measured in triplicate with a standard biochemical assay for amylase activity. As illustrated in FIG. 6 (bottom panel), the amylase enzyme retained its activity in the presence of both tested proteases.

Figure 7:
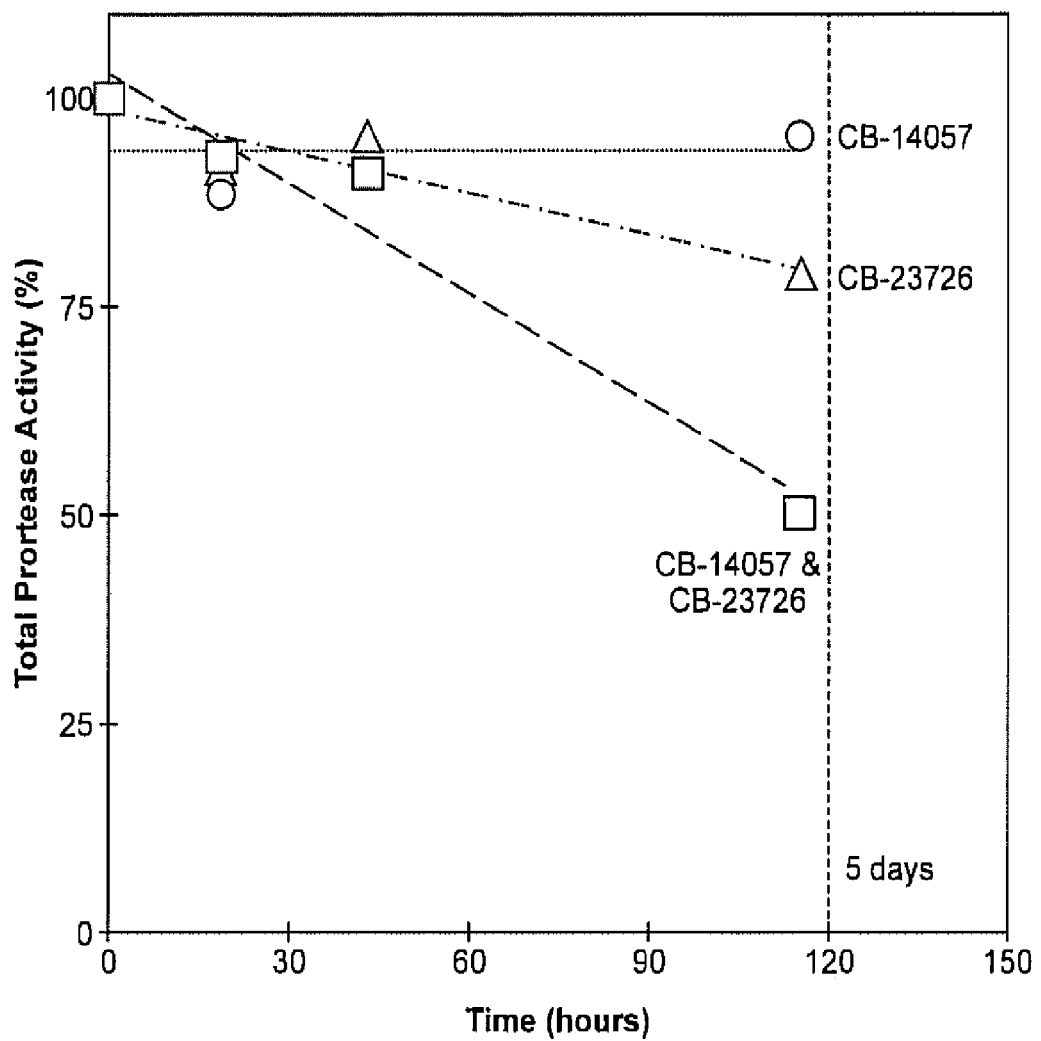
FIG. 7 is a scatter plot that illustrates minimal autolysis of ultrastable proteases and protease resistance of these enzymes.

In a third experiment, two ultrastable proteases were incubated together, and cross-compatibility activity of the proteases was assayed. The proteases were incubated separately or together at 80° C., pH 3.0 for up to five days and subsequently assayed using a standard biochemical assay for protease activity. As illustrated in FIG. 7, the results indicated that over 50% of original activity was exhibited by the mixture of proteases under the tested conditions, indicating resistance to proteolysis for both enzymes.

The results indicate that ultrastable lipase/protease, amylase/protease, and protease/protease combinations can be used on enzyme substrates without incurring enzyme inactivation by protease activity.

Example 6

Optimization of Enzyme Concentration (Ms-Based Proteomic Analysis)

Figure 9:
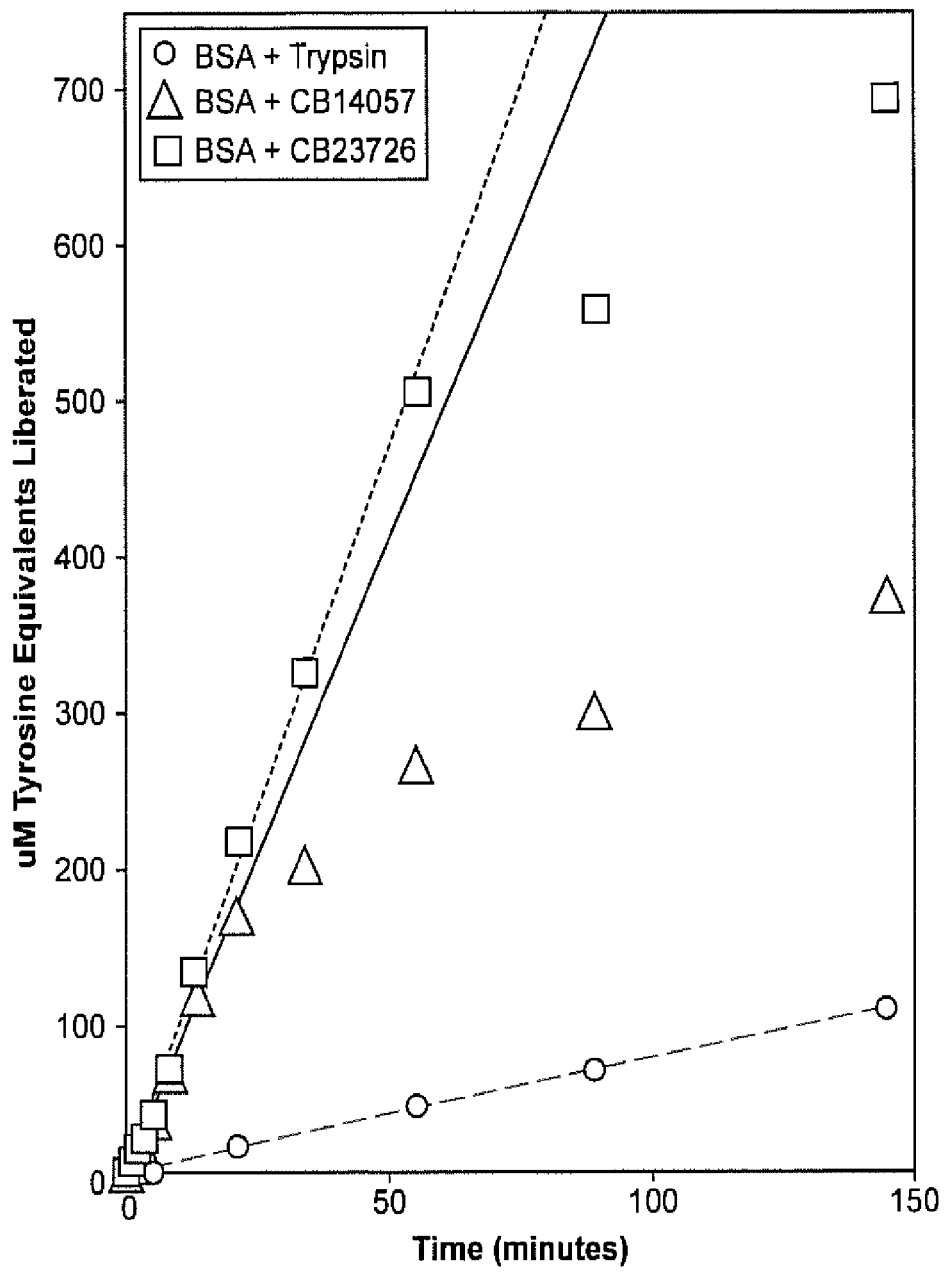
FIG. 9 is a time course graph of proteolyzed product formed using the standard tyrosine equivalence assay for two ultrastable proteses as compared to trypsin on the same bovine serum albumin (BSA) substrate

A series of enzyme/substrate ratios was tested at the defined optima for the candidate ("CB") proteases. Initially, the assays were carried out for one hour and visualized on coomassie brilliant blue (CBB)-stained SDS-PAGE as described (Example 4, FIG. 3). The initial experiment was used to approximately define appropriate enzyme concentrations for digestion reactions for various substrates and to guide serial enzyme concentration amounts for the proteomic analysis with finer gradation between concentration points. Initial rates were estimated from the linear regression of initial points before the break from linearity. All reactions were prepared with 1 µg of tested enzyme and 200 µg of BSA substrate, and enzyme/substrate mixtures were incubated at the temperature and pH optima for each tested enzyme. As enzyme concentration depends on time and substrate concentration, biochemical experimental data was also collected at various enzyme concentrations to provide information on enzyme amounts in formulations (FIG. 9). The results illustrated in FIG. 9 indicate that the tested ultrastable proteases exhibited significantly higher digestion rates of BSA compared to trypsin under their respective optimal conditions.

Example 7

Optimization of Sample Incubation (Digestion) Times (MS-Based Proteomic Analysis)

For each candidate enzyme, after defining the enzyme to substrate ratios best suited for proteomic analyses, the relative effectiveness of a selected enzyme concentration with various substrates is examined and compared to results using higher enzyme concentrations and shorter incubation times and/or lower enzyme concentrations and longer incubation times. Since adequate digestion with the benchmark enzyme trypsin typically requires 4 to 24 hours, the focus is on identifying reaction conditions that provide maximum digestion and coverage in less than 60 minutes. Based on preliminary experiments in which candidate proteases were compared to trypsin, there is a potential for significantly reduced digestion times (~1/10×) relative to trypsin (FIG. 9). Based on the preliminary experiments, it was observed that trypsin did not break from linearity while the candidate ("CB") enzymes digested enough BSA to break from linearity (i.e. sub-saturating substrate concentrations). Further studies are needed to investigate enzyme amount and reaction condition variables with readouts to include mass spectrometry in addition to biochemical assays.

Example 8

Optimization of Sample pH (MS-Based Proteomic Analysis)

Experiments to quantify the level and specificity of chemical hydrolysis from the heated acid reaction conditions for candidate enzymes on a set of test proteins are carried out. Previously, it was determined that candidate ("CB") protease enzymes exhibited nearly equivalent levels of biochemical activity in nitric, phosphoric, sulfuric, and citric acids (data not shown). Since these acids may have differing background hydrolysis or amino acid side chain chemistries at elevated temperatures, activity and acid hydrolysis of candidate enzymes in the presence of various acids set across a range of pH (1.5-4 at 80° C.) is carried out. In circumstances, certain pH can cause precipitation of target protein. Accordingly, experiments are carried out to compare the proteolytic performance under target protein precipitating pH conditions relative to other pH values that show less, or no, precipitation of target protein along the tested pH gradients. The results of such studies provides a basis for acids and pH values that are useful for formulating reaction mixes for commercial proteomics products.

Example 9

Optimization of Sample Temperature (MS-Based Proteomic Analysis)

As considerable efforts are being put towards automation of proteomic samples, including front-end immobilized enzyme reactor (IMER) technologies, candidate enzymes are investigated for use in automated processes involving enzyme immobilization and re-use for proteomics. To identify a practical intersect between temperatures and proteolytic performance, a study to investigate the function of candidate enzymes (e.g. proteases) in the context of proteomic mass spectrometry at temperatures below and above an identified optima is carried out. Lower temperatures may provide gains in enzyme half-lives for IMER and other relevant contexts. In contrast, elevated temperatures may reduce reaction times for one-off digestion applications.

Example 10

Assessment of Candidate Enzymes for Glycoproteomic Applications

Candidate enzymes are investigated for potential activity in debranching or depolymerizing glycans or cleave O- and N-linked sugar/protein bonds. Posttranslational modifications, particularly large and heterogeneous glycosylations, can interfere with proteases, chromatography, and yield limited protein coverage. Glycosylation of a large fraction of target proteins is particularly pronounced in membrane proteomics and neurobiology among other fields. Mesophilic enzymes are currently a leading option for the removal and/or degradation of these complex sugars for mass spectrometry analyses. However, the currently available enzymes require separate steps prior to proteolytic reactions, as trypsin degrades and inactivates the glycan-acting enzymes if the two enzymes are incubated together. The objective of such studies is to identify hyperstable candidate enzymes that can positively impact proteomic analysis of glycoproteins in addition to retaining their enzymatic activity despite the heat and acid of the reaction conditions. In a more particular embodiment, isolated thermo-acid stable glycohydrolases are investigated for their thermostability, utility in glycoprotein proteomics, and compatibility with candidate proteases.

Test substrates can include, e.g., RNase B, for demonstration of N-linked deglycosylation using SDS-PAGE and proteomics, and interleukin-6 and α1-Acid Glycoprotein for O- and N-linked deglycosylation (Sigma). Candidate enzymes are tested for activity on these glycoprotein substrates. Experimental readouts include, e.g., gel mobility alteration and changes in protein coverage using proteomic data. Biochemical assays for detecting free sugars are also used if appropriate. Positive controls include commercially available protein deglycosylation kits (Sigma).

A matrix of each result generated from reaction between a candidate enzyme and a substrate, as evaluated by SDS-PAGE stained with coomassie brilliant blue (CBB) or Schiff stain for glycans is produced. The initial experiments provide a coarse readout on the enzymes that have the most significant effect on the glycosylation, and the class(es) of glycans that are acted upon by using the various substrates. Collation of these data is used to guide follow-on experiments. Once a set of promising candidate enzymes is determined, proteomic analyses is carried out with trypsin (benchmark) and the candidate proteases using reaction conditions determined prior (Examples 3-7). Identification of enzymes that deglycosylate the substrates in a manner that liberates peptides from the linked glycans is carried out based on these data. The utility of such hyperstable glycan enzymes for single-step glycoproteomic reactions is further assessed and formulated with hyperstable candidate proteases.

Example 11

Assessment of Compatibility of Ultrastable Proteases with Glycohydrolases for Formulation Commercially available deglycosylation kits and procedures involve many steps and are laborious and time consuming (e.g., Sigma deglycosylation-kits). Glycoproteomic protocols are generally multiple step, can be somewhat complex, time consuming, and require extensive sample handling and subsequent losses and introduce significant sample-to-sample variation. Much of the process time and steps can be attributed to sequential incubations and drying to remove SDS from gel slices and to compensate for the incompatibility of glycan enzymes and protease enzymes. Some protocols also involve a thermal denaturation step of 100° C. to assist in downstream enzymatic digestion. Accordingly, there are potential advantages for combining multiple steps into a single process step that significantly reduces time, handling, and variability. Specifically, heat denaturation, deglycosylation, and proteolytic digestion that are tolerant of SDS from gel slices can be carried out in a single step using ultrastable enzyme formulations.

A limited set of pilot experiments was carried out to 1) further assess a library of potentially useful glycan enzymes, and 2) assess the compatibility of these enzymes with proteases for acid/heat/detergent stable formulations. Guided by the results from Example 9, the relative stability of glycan-cleaving enzymes in the presence of hyperstable proteases was assessed. Pilot experiments for two candidate glycohydrolases were previously carried out, and both enzymes retained >95% of their activity after one hour at 80° C. and pH=3 in the presence of excess of two candidate proteases (data not shown).

However, not all of candidate enzymes are resistant to protease cleavage, suggesting that 1) various enzymes have differing resistance to hyperstable candidate proteases, and 2) the resistance can be pairwise-specific. To illustrate these points, a matrix of pH, protease, and lipase reactions with a visual readout assay is provided in FIG. 6. In FIG. 6, the results were generated by reacting two different lipases with two different proteases with pH 3 or 6 buffer controls for 30 minutes at 80° C. Aliquots of 7.5 µL of the resulting reaction mixtures were then spotted onto a solid matrix plate with a pre-formed emulsion of ghee (clarified butter) at pH=3 and incubated at 80° C. for 30 minutes and photographed against a dark background. The lipase activity on the ghee emulsion is visualized as clearing of opacity, to notably differing degrees for the different lipases (FIG. 6, top two rows). In particular, this experiment revealed a combination of protease and lipase that were compatible for co-formulation (FIG. 6, box), while other protease/lipase combinations resulted in significantly diminished lipase activity. These data indicate that not all hyperstable candidate enzymes are equally resistant to various hyperstable candidate proteases.

A similar matrix of tests between the proteases and glycan-digesting enzymes is executed. Protease compatibility of glycohydrolases is assessed by established biochemical assays for each relevant glycohydrolase activity being tested as compared to mock reactions lacking protease. Remaining glycohydrolytic activity after protease pre-treatment indicates protease resistance, and the values give an indication of the level of resistance and allow ranking of candidate glycohydrolases for co-formulation with candidate proteases.

Example 12

Assessing Simultaneous Deglycosylation and Proteolysis of Candidate Enzymes

Glycohydrolases that show potential for removing glycans to allow identification of modified peptides are further tested. A subset of enzymes that show incompatibility with candidate proteases is tested in a two-step deglycosylation protocol. The protease-tolerant glycohydrolases (as identified) are tested for their impact on proteomic coverage of the glycoprotein substrates in single-step glycoproteomic reactions. Initial incubation times, enzyme doses, and optimal pH and temperatures for reactions is guided by previous experimentation (e.g., as illustrated in Example 2) as well as historical data. The objective of these experiments is furthering the development of a set of products that simplify glycoproteomic and proteomic sample preparation. These products can take many forms, however, experimentation to date encourages an embodiment of a dried 96-well plate format that is stable at room temperature and requires only rehydration, sample addition, and incubation prior to proteomic analysis.

Example 13

Preparation of a Sample Using an Enzyme Mixture

A biological sample is obtained and incubated with a composition containing a mesophilic glycohydrolase and an ultrastable protease. The mixture is incubated at 37° C. for one hour and subsequently incubated at 80° C. for one hour. The mixture is optionally incubated at a pH of between 2 to 5 for one or both incubation periods. Incubation at the lower temperature allows enzymatic cleavage of carbohydrates at glycosylated sites in proteins of the sample. Subsequent incubation at the higher temperature allows enzymatic digestion of the proteins in the sample to produce smaller peptide fragments for proteomic analysis. After the second incubation period, the sample is injected onto a mass spectrometer for proteomic analysis.

Example 14

Preparation of a Sample for Lipomic Analysis

A biological sample is obtained and incubated with a composition an ultrastable lipase and optionally, an ultrastable protease. The mixture is incubated at 80° C. for one hour. The mixture is optionally incubated at a pH of between 2 to 5 and/or optionally incubated in the presence of a detergent, a surfactant, and/or a redox compound. After the incubation period, the sample is analysed for lipomic analysis.

Example 15

Preparation of a Sample for Glycomic Analysis

A biological sample is obtained and incubated with a composition an ultrastable amylase and optionally, an ultrastable protease. The mixture is incubated at 80° C. for one hour. The mixture is optionally incubated at a pH of between 2 to 5 and/or optionally incubated in the presence of a detergent, a surfactant, and/or a redox compound. After the incubation period, the sample is analysed for glycomic analysis.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. Anson M L (1938) The Estimation of Pepsin, Trypsin, Papain, and Cathepsin with Hemoglobin. J Gen Physiol 22: 79-89.
2. Ciocalteu OFaV (1929) ON TYROSINE AND TRYPTOPHANE DETERMINATIONS IN PROTEINS. J Biol Chem 73: 627-650.
3. Ivanov A R, Lazarev A (2011) Sample preparation in biological mass spectrometry. Dordrecht: Springer. xxix, 1089 pages.

What is claimed:

1. A method of preparing a biological sample, comprising:
   (a) providing the biological sample comprising at least one biopolymer;
   (b) contacting the sample with a composition comprising an ultrastable enzyme from an organism of the Archaea domain, to form a reaction mixture, wherein the ultrastable enzyme cleaves the biopolymer at one or more specific sites, and wherein the ultrastable enzyme is selected from the group consisting of SEQ ID NO: 26 and SEQ ID NO: 35; and
   (c) incubating the reaction mixture for at least one second to digest the at least one biopolymer present in the biological sample, at a pH between 0.5-7.0 and a temperature between 50° C.-150° C., and
   wherein steps (a) to (c) produce a prepared sample for proteomic, glycomic, or glycoproteomic analysis, and wherein the prepared sample is injected into an analytical device for proteomic, glycomic, or glycoproteomic analysis after step (c).

2. The method of claim 1, wherein the biological sample is prepared for mass spectrometry-based proteomic, glycomic, glycoproteomic, lipomic, amino acid, enzymatic, or immunochemical analysis.

3. The method of claim 1, wherein the sample is selected from the group consisting of a tissue, a cell pellet, a cell lysate, a cell culture solution, a biological fluid, a food product, and a gel sample.

4. The method of claim 1, wherein the composition of step (b) further comprises an acid.

5. The method of claim 4, wherein the composition of step (b) comprises an acid, wherein the acid is selected from the group consisting of nitric acid, phosphoric acid, hydrofluoric acid, sulfuric acid, hydrochloric acid, acetic acid, paracetic acid, citric acid, glycolic acid, formic acid, and combinations thereof.

6. The method of claim 1, wherein the composition of step (b) further comprises a surfactant or detergent.

7. The method of claim 1, wherein the composition of step (b) further comprises an additive.

8. The method of claim 1, wherein the reaction mixture in step (c) is incubated at a temperature of from about 50° C. to about 150° C.

9. The method of claim 1, wherein the reaction mixture in step (c) is incubated at a pH from about 0.5 to about 7.0.

10. The method of claim 1, wherein the reaction mixture in step (c) is incubated for less than 8 hours.

11. The method of claim 1, wherein the reaction mixture in step (c) is incubated for a duration of time ranging from about 12 hours to about 7 days.

12. The method of claim 1, wherein the method results in at least 5% digestion of the total amount of the biopolymer in the sample.

13. The method of claim 1, further comprising adjusting the pH of the reaction mixture to a pH value from about 4.5 to about 7.0, after incubating the reaction mixture.

14. The method of claim 13, further comprising adjusting the temperature of the reaction mixture to a temperature from about 4° C. to about 37° C., after adjusting the pH of the reaction mixture to a pH value from about 4.5 to about 7.0.

15. The method of claim 1, further comprising treating the reaction mixture to remove one of more contaminants, and wherein treating the reaction mixture comprises removing one or more contaminants from the reaction mixture by chromatography.

16. The method of claim 1, further comprising drying the reaction mixture.

17. The method of claim 1, further comprising storing the prepared sample for a duration of time from about 30 days to about 10 years.

18. The method of claim 4, wherein the composition of step (b) further comprises an additive, wherein the additive is selected from the group consisting of: iodoacetamide (IAA), dithiothreitol (DTT), and any combination thereof.

19. The method of claim 1, wherein the composition of step (b) further comprises an oxidizer.

* * * * *

SEQUENCE LISTING

```
<160> NUMBER OF SEQ ID NOS: 35

<210> SEQ ID NO 1
<211> LENGTH: 49
<212> TYPE: DNA
<213> ORGANISM: Artificial Sequence
<220> FEATURE:
<223> OTHER INFORMATION: synthetic nucleotide sequence

<400> SEQUENCE: 1
cgccgcggcc gggatttgaa cccgggtcac gggctcgaga ggcccgcat          49

<210> SEQ ID NO 2
<211> LENGTH: 49
<212> TYPE: DNA
<213> ORGANISM: Artificial Sequence
<220> FEATURE:
<223> OTHER INFORMATION: synthetic nucleotide sequence

<400> SEQUENCE: 2
tgccgcggcc gggatttgaa cccgggtcag gggctcgaga ggcccgcat          49

<210> SEQ ID NO 3
<211> LENGTH: 45
<212> TYPE: DNA
<213> ORGANISM: Artificial Sequence
<220> FEATURE:
<223> OTHER INFORMATION: synthetic nucleotide sequence

<400> SEQUENCE: 3
ggggcgcgga ctgaggctcc gctggcgaag gcctgcacgg gttca              45

<210> SEQ ID NO 4
<211> LENGTH: 44
<212> TYPE: DNA
<213> ORGANISM: Artificial Sequence
<220> FEATURE:
<223> OTHER INFORMATION: synthetic nucleotide sequence

<400> SEQUENCE: 4
gggggcggac tgaggctccg ctggcgaagg cctgcacggg ttca               44

<210> SEQ ID NO 5
<211> LENGTH: 28
<212> TYPE: DNA
<213> ORGANISM: Artificial Sequence
<220> FEATURE:
<223> OTHER INFORMATION: synthetic nucleotide sequence

<400> SEQUENCE: 5
tccgctggcg aaggcctgca cgggttca                                 28
```

```
<210> SEQ ID NO 6
<211> LENGTH: 48
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (29)..(29)
<223> OTHER INFORMATION: S = C or G

<400> SEQUENCE: 6
gccgcggccg ggatttgaac ccgggtcasg ggctcgagag gcccgcat          48

<210> SEQ ID NO 7
<211> LENGTH: 49
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (1)..(1)
<223> OTHER INFORMATION: Y = C or T
<220> FEATURE:
<221> NAME/KEY: misc_feature
<222> LOCATION: (30)..(30)
<223> OTHER INFORMATION: S = C or G

<400> SEQUENCE: 7
ygccgcggcc gggatttgaa cccgggtcas gggctcgaga ggcccgcat         49

<210> SEQ ID NO 8
<211> LENGTH: 28
<212> TYPE: DNA
<213> ORGANISM: Artificial Sequence
<220> FEATURE:
<223> OTHER INFORMATION: synthetic nucleotide sequence

<400> SEQUENCE: 8
tccgctggcg aaggcctgca cgggttca                                28

<210> SEQ ID NO 9
<211> LENGTH: 44
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (4)..(4)
<223> OTHER INFORMATION: S = C or G

<400> SEQUENCE: 9
gggsgcggac tgaggctccg ctggcgaagg cctgcacggg ttca              44

<210> SEQ ID NO 10
<211> LENGTH: 22073
<212> TYPE: DNA
<213> ORGANISM: Artificial Sequence
<220> FEATURE:
<223> OTHER INFORMATION: synthetic nucleotide vector sequence

<400> SEQUENCE: 10
tcattttttc ctaaaaattg ctcctttaca tttcatcacc ttatcctcga taatcttatt    60
tatagttctt aatgctgtta atggattccc tgcattataa atacttcttc caatgatttc   120
```

```
ataatccgct ccagcacata ctgcatcgcc ataacttcca ccttgactac ccatacccgg    180
agagactatg gtcattttt tcgaagtctct cctatactgc gttatatgat ctaatttagt    240
ccctccaact actattcctt ttgggcttat ctctcttata acgttttta tatagtctgc    300 gaataacgta ctccatcctt catgtgacat tacggcaact aagtataaat ttttagagtt    360
tgcatcaaga tatcttttta attcatctag agatcccctta acgcctataa aggaatgtgc   420
tatgaacgag ttggcgaaag ataatctttc aactatgctt ttcattatgt atccgatatc    480
tgcaagctta aaatcaacaa taatttcctc cacgtctaaa ccaattaaga gctctctagt    540
tttatccact cctagatcta aaactaaagg taaaccaact tttatcccat ataactcatt    600
ttccatctct ttaagaactt gatatgagag aggtttatcc attgctaata ttactctact    660
tttcaacatt cttcaccaaa taatctagaa ttgacttctt ttcattatcc ttaagtttat    720
cactcttcaa caattcatct agaatttctg aaattttaaa tagagagtgt aatttgactc    780 ctagttttc caatctttgt gaagccccctt cttgtctatc tatgattact agtgcgtctg    840
aaactttacc tccaccgtta agaatctcca atgttgcttt ctctatggat actcctgtag    900
ttgcaacgtc atctactaac aatactcttt ttccttttac atcgagttct aatgtacgat    960
tagttccatg acctttcttt tctattctaa tatatcccat aggctcttta aggttacaag   1020
ctatgaatgc cgataaggga actcctccag tggctattcc tactattata tcatggggta   1080
tatcttttgc tttctttata gcttgattaa ctatatcgta aaattctgga taatttggta   1140
aaggtcttaa gtctaagtaa tatggactaa ccttacctga tgttaaaacg aaacttccta   1200
ttaataataa tttcctttcg agtaagactt ctgcgaaatt catacgtaga gactctgcga   1260
aaaagaattt aaatatactt ctatcataac cagttataag ggctttgtga gattaagaca   1320
cgtagtttcg tcgcttgact tgaccagaga tgactacttt agaatattcg aacttgcaga   1380
caagttctat gatgtaaaaa aactaaatta tctatcaggg aaagtagttt cattagcatt   1440
ctttgagcca agtactagaa ctgctcaaag ctttcatact gcagcaataa aattaggtgc   1500
tgatgtgata ggatttgcat ccgaggagtc tacttcgata gcaaaaggtg aaaatttggc   1560
tgataccatt aggatgctaa acaactattc aaactgtatt gtaatgagac ataagtttga   1620
tggggcagca ttattcccta ggccgtgatt tcgtaatatt gtaagttaaa tttagcgtag   1680
attttgttta ttatatttttt tagaatttca cgaataaagc ttaagtaaga gggataagcg   1740
aataagatct tgtctttata tactattatc tttctcggat aaagctctct tttaattctc   1800
ttggttatct catctttact gcatatttca cataatcttc ttcctcctac tacgtttatg   1860
gcatttcttt tgttacatct ttcgcacatc atattagagg agaatggatt tcctatttat   1920
ttaaaaaatt acttctcggt ttagctgaga gaaaaatttt tatataagcg atactaatgt   1980
tctcacggaa cggtgttgtg aggtactagt ccagtgtggt ggaattctgc agatatcaac   2040
aagtttgtac aaaaaagctg aacgagaaac gtaaatgat ataaatatca atatattaaa    2100
ttagattttg cataaaaaac agactacata atactgtaaa acacaacata tccagtcact   2160
atggcggccg cattaggcac cccaggcttt acactttatg cttccggctc gtataatgtg   2220
tggattttga gttaggatcc gtcgagattt caggagcta aggaagctaa aatgagagaaa  2280 aaaatcactg gatataccac cgttgatata tcccaatggc atcgtaaaga acattttgag   2340
gcatttcagt cagttgctca atgtacctat aaccagaccg ttcagctgga tattacggcc   2400 ttttttaaaga ccgtaaagaa aaataagcac aagtttatc cggcctttat tcacattctt   2460
gcccgcctga tgaatgctca tccggaattc cgtatggcaa tgaaagacgg tgagctggtg   2520
```

```
atatgggata gtgttcaccc ttgttacacc gttttccatg agcaaactga aacgttttca    2580
tcgctctgga gtgaatacca cgacgatttc cggcagtttc tacacatata ttcgcaagat    2640
gtggcgtgtt acggtgaaaa cctggcctat ttccctaaag ggtttattga gaatatgttt    2700
ttcgtctcag ccaatccctg ggtgagtttc accagttttg atttaaacgt ggccaatatg    2760
gacaacttct tcgcccccgt tttcaccatg gcaaatatt atacgcaagg cgacaaggtg     2820
ctgatgccgc tggcgattca ggttcatcat gccgtttgtg atggctttcc atgtcggcag    2880
aatgcttaat gaattacaac agtactgcga tgagtggcag ggcggggcgt aaagatctgg    2940
atccggctta ctaaaagcca gataacagta tgcgtatttg cgcgctgatt tttgcggtat    3000
aagaatatat actgatatgt atacccgaag tatgtcaaaa agaggtatgc tatgaagcag    3060
cgtattacag tgacagttga cagcgacagc tatcagttgc tcaaggcata tatgatgtca    3120
atatctccgg tctggtaagc acaaccatgc agaatgaagc ccgtcgtctg cgtgccgaac    3180
gctggaaagc ggaaaatcag gaagggatgg ctgaggtcgc ccggtttatt gaaatgaacg    3240
gctcttttgc tgacgagaac aggggctggt gaaatgcagt ttaaggttta cacctataaa    3300
agagagagcc gttatcgtct gtttgtggat gtacagagtg atattattga cacgcccggg    3360
cgacggatgg tgatccccct ggccagtgca cgtctgctgt cagataaagt ctcccgtgaa    3420
ctttacccgg tggtgcatat cggggatgaa agctggcgca tgatgaccac cgatatggcc    3480
agtgtgccgg tctccgttat cggggaagaa gtggctgatc tcagccaccg cgaaaatgac    3540
atcaaaaacg ccattaacct gatgttctgg ggaatataaa tgtcaggctc ccttatacac    3600
agccagtctg caggtcgacc atagtgactg gatatgttgt gttttacagt attatgtagt    3660 ctgttttta tgcaaaatct aatttaatat attgatattt atcattttt acgtttctcg      3720 ttcagctttc ttgtacaaag tggttgatat ccagcacagt ggcgccggcc gccaccgcgg    3780
tggagctcga attcgtaatc atgtcatagc tgtttcctgt gtgaaattgt tatccgctca    3840
caattccaca caacatacga gccggaagca taaagtgtaa agcctggggt gcctaatgag    3900
tgagctaact cacattaatt gcgttgcgct cactgcccgc tttccagtcg ggaaacctgt    3960
cgtgccagct gcattaatga atcggccaac gcgcggggag aggcggtttg cgtattgggc    4020
gctcttccgc ttcctcgctc actgactcgc tgcgctcggt cgttcggctg cggcgagcgg    4080
tatcagctca ctcaaaggcg gtaatacggt tatccacaga atcaggggat aacgcaggaa    4140
agaacatgtg agcaaaaggc cagcaaaagg ccaggaaccg taaaaaggcc gcgttgctgg    4200 cgttttcca taggctccgc cccctgacg agcatcacaa aaatcgacgc tcaagtcaga    4260
ggtggcgaaa cccgacagga ctataaagat accaggcgtt tccccctgga agctccctcg    4320
tgcgctctcc tgttccgacc ctgccgctta ccggatacct gtccgccttt ctcccttcgg    4380
gaagcgtggc gctttctcat agctcacgct gtaggtatct cagttcggtg taggtcgttc    4440
gctccaagct gggctgtgtg cacgaacccc cgttcagcc cgaccgctgc gccttatccg    4500
gtaactatcg tcttgagtcc aacccggtaa gacacgactt atcgccactg gcagcagcca    4560
ctggtaacag gattagcaga gcgaggtatg taggcggtgc tacagagttc ttgaagtggt    4620
ggcctaacta cggctacact agaaggacag tatttggtat ctgcgctctg ctgaagccag    4680
ttaccttcgg aaaaagagtt ggtagctctt gatccggcaa acaaaccacc gctggtagcg    4740 gtggttttt tgtttgcaag cagcagatta cgcgcagaaa aaaaggatct caagaagatc    4800
ctttgatctt ttctacgggg tctgacgctc agtggaacga aaactcacgt taagggattt    4860
```

```
tggtcatgag attatcaaaa aggatcttca cctagatcct tttaaattaa aaatgaagtt      4920
ttaaatcaat ctaaagtata tatgagtaaa cttggtctga cagttaccaa tgcttaatca      4980
gtgaggcacc tatctcagcg atctgtctat ttcgttcatc catagttgcc tgactccccg      5040
tcgtgtagat aactacgata cgggagggct taccatctgg ccccagtgct gcaatgatac      5100
cgcgagaccc acgctcaccg gctccagatt tatcagcaat aaaccagcca gccggaaggg      5160
ccgagcgcag aagtggtcct gcaactttat ccgcctccat ccagtctatt aattgttgcc      5220
gggaagctag agtaagtagt tcgccagtta atagtttgcg caacgttgtt gccattgcta      5280
caggcatcgt ggtgtcacgc tcgtcgtttg gtatggcttc attcagctcc ggttcccaac      5340
gatcaaggcg agttacatga tcccccatgt tgtgcaaaaa agcggttagc tccttcggtc      5400
ctccgatcgt tgtcagaagt aagttggccg cagtgttatc actcatggtt atggcagcac      5460
tgcataattc tcttactgtc atgccatccg taagatgctt ttctgtgact ggtgagtact      5520
caaccaagtc attctgagaa tagtgtatgc ggcgaccgag ttgctcttgc ccggcgtcaa      5580
tacgggataa taccgcgcca catagcagaa ctttaaaagt gctcatcatt ggaaaacgtt      5640
cttcggggcg aaaactctca aggatcttac cgctgttgag atccagttcg atgtaaccca      5700
ctcgtgcacc caactgatct tcagcatctt ttactttcac cagcgtttct gggtgagcaa      5760
aaacaggaag gcaaaatgcc gcaaaaaagg gaataagggc gacacggaaa tgttgaatac      5820
tcatactctt cctttttcaa tattattgaa gcatttatca gggttattgt ctcatgagcg      5880
gatacatatt tgaatgtatt tagaaaaata acaaataggg gttccgcgc acatttcccc       5940 gaaaagtgcc acctgacgtc taagaaacca ttattatcat gacattaacc tataaaaata      6000
ggcgtatcac gaggcccttt cgtctcgcgc gtttcggtga tgacggtgaa aacctctgac      6060
acatgcagct cccggagacg gtcacagctt gtctgtaagc ggatgccggg agcagacaag      6120
cccgtcaggg cgcgtcagcg ggtgttggcg ggtgtcgggg ctggcttaac tatgcggcat      6180
cagagcagat tgtactgaga gtgcaccata tgcggtgtga ataccgcac agatgcgtaa       6240 ggagaaaata ccgcatcagg cgccattcgc cattcaggct gcgcaactgt tgggaagggc      6300
gatcggtgcg ggcctcttcg ctattacgcc agctggcgaa aggggggatgt gctgcaaggc     6360 gattaagttg ggtaacgcca gggttttccc agtcacgacg ttgtaaaacg acggccagtg      6420
ccaagcttgc atgcctgcag agtctcatat gtttcctcac ttattgaaat gttaagcctt      6480
ttgactatcc tatctttcct cttctctatc atttaggtca ccttgtttat tgttatttga      6540
aatacgtatc cgtcttcgtc acatcgaagt ataattttgt atccattatt agcatattct      6600
acgtcaaagt tcccacaaca ataattcggg tcttcggact cgttatagac tttgctccaa      6660
ccatcttttt gtagtgcctc ttctaagtag tctactctga tgaagccttc atcatattcg      6720
ttcagtaccc taaagcttat actatcaatg cctaatacgt ctaatagctt caacagatcg      6780
aatataggaa cttgcaccat catttcagct caccttaatg agctgatata attccgcttc      6840
tatcttttga acttggaagt atgccttgcc tagcttttgc ttatccatat tgcccgttat      6900
tctatcaatc ttaatctcgt ggattaatga taatagctct ctgacatcct catcaagcat      6960
ttcaaataat tctttctcta agacttcttt actcattgtt tttcacctta gcaaactcat      7020
ctaacgttgt ttgtctcagt tctctttttct ttatcaaata aaattccgaa tgtcccttct     7080
tattgttatt actgtacttc atgtcagttc actgctttgc cttttataaat ccttgatccg     7140 tttgctcaaa atttgcgggc tgggcatcaa atatcttagc tatattgtct tgtgtttgct      7200
cttgtttttg ttcttctttc tgctcttgct taatccattt gaacgttgtc tttctgtttt      7260
```

-continued

```
tgtattgtac ttcacactcg tctggatgtc tttcgcaaat agctttcaat gctctctgta    7320
tgttatacgc actcgggact gaaatctcaa attgagctag tatatcctct aacgttaatt    7380
cacctttctt ttcaagaatt ttatacatta tttccgccat cttgtatgaa tttagagttt    7440
gtgccatatt cccatcccac tctatctata ctctatgtat aaattagtat ttaagtctta    7500
ctctatctat actctatcta tctctctata tacacagtgt ttgggtaact ggcaaaattc    7560
tgtctgactg ctgtctgaca agagtttact ctatctctct atatctatat acacaaacag    7620
agttagtcga ctctgtgtat cttatgtatc ttatacaaaa aatatgggat gtgcaaaatc    7680
tgagctacta atactgcttg aatatataga tagagagtgt aaggactacg agagttgtaa    7740
aagaataata gtagagctag aagagagagt gaagaaaata gctttcgtag aagcaataaa    7800
tgatttgttc taaactactt ttttctctct atctctatat ctatatatat acataactaa    7860
aactaaaaga ataaacaaaa aactaacaaa atcaactcac cattatacaa actcagaaaa    7920
actatttttt tgttatactc ttaccccata tatatataga tatatagata gagagagata    7980
gagtatagta gggcatttaa gatttttagaa gttcttcaat gcgtcttctg attgcatctg    8040
caacaaactc ttgtctgctt atatatccgc ccttgcctga cgctattagt tcatctattt    8100
gttttgctaa ttcgattgga atcgaaacgg tcacatattc ttttttgact gatttcctcg    8160
gcatacgcta tctatactat attaatatga taatattaaa tgattcacga tatatagata    8220
gagtatagat agagtaaagt ttaaatactt atatagatag agtatagata gagggttcaa    8280
aaaatggttt caccccaaac ccgaaaagaa gaagagttat tagaaaaaca aaattcagtt    8340
ttttatttgt taactttagg aaggaaaccg tatggttcat atttgcatat aaaaattgaa    8400
ctagacgaag atgaaaaatt agagaaggaa atctatgcgg ataacattaa gctagagaat    8460
gaattaagac aactgaagag gttgtatgaa gtatatcaga gcgtagagat tgacgatgct    8520
cagaaagcaa tacagaagga agcattactg acgatagcga aaatactaag tgtttttgac    8580
ttctgaggag gctgaggggc aatgaaggct gaggaaacaa tcgtggaaca gattcaggac    8640
ataattcaaa aacttcgcta ttatacagga agatcaaata gacatttcaa gatgattaga    8700 aactatatg aggagtgtat aataaatagta gacgctgagg agtttataca agaaaataac    8760
actctaagca ttactgtata ttctgaggat cttatatatt atactgttga tatcccgctg    8820
aatttcatta aacatgtatt cgtatccgct tcgattgatc agctcaatga tcagcttcag    8880
ctaaaatata atgagggtct gattagagtt tctcttactt tgaacgatga cttatgtgag    8940
aaactgagaa gctcatactg cggtgatatt acattcttta atgaggctga ggggcaatga    9000
aggctagggt tgaatacatc aaattaccta gatgttacac aaaaacttat agaaaaatcg    9060
aagcgaaaaa gaacaacgac ggtacaatag aattaacgtt agaggaaaca atgcaagtaa    9120
tatcctttaa actaccccg gcgttaaatg caaaactaga acaaattgcg atcaaagaaa    9180
agaaaagcaa gagtgaaatt attcgaatag cgttagcgag gtatgtagaa aatgtttaga    9240
tgccccatct gcgggttcaa aacgctgaga ttgttcgcgc ttaaacaaca tactcgaagg    9300
gagcatgtgt tggtcaaatg tcccatatgc gggttcacgg ggaagcattt atctcaacat    9360
ttctatagta ggtatgatat tgaccatctc atatactgct acctattctc ttctttcaga    9420
ttgcctaaga atgttaggtt agcaataaag agaaaattag aggttgagtg aataatgtat    9480
caatgtctac gttgtggtgg tatatttaat aaaagaagag aagtggttga gcatttgctt    9540
gtagggcata agcacaagga tagactaaca ctggactttt attatatcta cttcagggtg    9600
```

```
agaggacaat gaacctaatt gatatcatct tattttacgg ctttcaattc aacgattatt    9660
ggacaactgt cttagggttg agagtgggtg cggaagagaa gaatcccata gcgggtctgt    9720
tcatttcatc accgtatcgt ttagcgttgt ttaagtttgg ccttatcacc attggtatgt    9780
ttatattaat ttatgttgtt agattcaaga catggacaga gatcgtattg actgtaacag    9840
acgttgtcga atgccttgtc acgctgaata atacccttac gattaggagg tacaaaagga    9900
ggggcgttag aggatgacgg agtcagacgt tgactcaggt agtaaaaaat acctgagtaa    9960
ccataagggg atttttattc atgtcacact ggaagagtta aagcgttacc accaacttac    10020
gccggaacag aagaggttga taagggcaat cgtcaaaacg cttattcata acccgcaact    10080
gttggatgaa agcagttatc tttacagatt gctcgcgagt aaagcgattt cacagtttgt    10140
ctgcccgctt tgtctaatgc ccttcagctc ttccgtatca ctaaagcaac acatccgtta    10200
tactgaacac acaaaggttt gcccggtgtg taaaaaggag tttacctcaa ccgattcagc    10260
cctagaccat gtttgcaaaa agcataatat ctgcgttagt taggctcttt ttaaagtcta    10320
ccttcttttt cgcttacaat gaggaagtcc cttctagccc tactaaccct atccctagcg    10380
ttactatcgt ttttaataac accatcgatg gcattgaatt ctggcggttc accgataccg    10440
atatattata actattataa ctactatagc cttaacgcag aagggtttgg attcagtttc    10500
aataatagca ataattgggt tgaaacgaac tttatctcaa taaccataaa cttacctagt    10560
tcattaccaa ataactatca aatcaataat gcctattcta tcgtagtagg attatcacca    10620
tatccggtta gcaatataaa cattttaat agcccattag aagcatatgt tgaactattc    10680
tcaaacccac cgaatacata tccaaatgaa ataggatttg tagttagtta cggctcaact    10740
gtattttata gttataccac actgtatagc agttttgcgg gcacacaact aacaataact    10800
atatcatata ccggaaatgg gtttggtgtg caattctctg acagtaacgg gttctctcac    10860
tcagtttcgg taagttcggt aaactttgta ccatatggtg ctctaatact cggatcacta    10920
atcccgaacg ggaactatta ctactaccca gtaggtaaca tgttaccgaa tgcatcggtg    10980
aacttctcat atacgatctc aagtttcaca atagaaggaa acccggccac atccgtcgat    11040
attaccacac ttggattaga aggaaacact gcaatatata cttcaagtag caattggttc    11100
aaatgggtat ccggtagtgt ggttatcaca aatgccgttg cctataccta taccgatttg    11160
gctagaatag gaggaagtgc acaaataaac tatactgcat cgcagctata ttaagcaaaa    11220
tcttttttta cctctttta aatctgtctt atatgaaaaa actgtttaca gttgtaggtt    11280
ctattttctc tggtttgggg atttggctta agtcaataga ccagtcattt tatttaacga    11340
aagtattgta taacggaaaa gtaattgaaa tagttctaac gcccgagaca aatgaagtcg    11400
tgaaatcttc caacggtgtt atgaacgcaa gtgtaacttc tctaccttcc acaattctat    11460
accaagcaca atccgtgcct tcaataaatg gaggaactct tagtgtaata aataccacag    11520
ttcaaccgcc atggtatgct aacttatggc ctgaagtctt aacaataggt atagtgatgt    11580
tgggaattgc aatattcagc tggattaaac ttaaatttag aagatagccc tttttaaagc    11640
cataaatttt ttatcgctta atgaagtggg gactattatt cttaataatg tttatatcca    11700 tttttttccct caactctta gccctattaa tcggcggagg agggcccaac aataatggtg    11760
cgggagttta cactcagact ataacagtta acggaggaac cgtacgaact actcttaacg    11820
gttcaacgct ttctaccgca ccatggctca accctcttta cgtaagcgtc tacaacacat    11880
actaccttca ggttttgccg aaccaagagt atattgacaa caacgtttcg ttatccctaa    11940
atacggctaa cattgcgtta aacgtcactt ggttattggc gtcctcaagc aatacgggat    12000
```

```
cctacggtgc aatcgccata ggctacggag tgaactttcc cgcggggttt gtcaataact    12060
acggtccttc cgcaccttac acgccggacg gaatcgtaat atatctcatg aaaggaggca    12120
tgccgaccta tcgtttattc gtatacttca atggagttga gcagttaaac gtttcagtcg    12180
ggtcaatcag tgtgggacaa aaaataggtt tagggttctt ttatctacag aacacacttt    12240
acgtttacta ctataacggt actttaaaga cttggtcatt aacgcccggt acgctgatta    12300
ctataaatag taattacgtt atagacgcac agaatatagg gccgggctac ggctacggtc    12360
aatgggtaat agttaattat caatatgcga tgccggttac tgcacaactg acggttagtt    12420
atttcgcatt agggtacaat gtatatcatt tcttaatggc ttatgcgggt gctggaaacc    12480
cggtaaacat aactgcgaat aacggggctt cttacagtat aacgggtata gttgcagaga    12540
agaactttac gataacggga attcagcaag gcctagccta tgctttcagc ttgttaggga    12600
aaccgaatgg cttatactta ttatatatgg ggccaattga gggcagccca ccaacgtggt    12660
atgtaaacgt aaccgtaggg cttcagatcg ttacacccca gaaaacgata aactacaact    12720
taacaatacc agtaatcgtt gagggctatg cgttatacccc ttctgttaac gtaccttccg    12780
gaacttacct aagcggacag actattagct ttaccctctc atcgttcttg ggataccctt    12840
caggcttagg ctattacacc gcagtaaatc taatcgcaaa cgtaacaata aacggtgtga    12900
gtcatgctat cccctatagt ttcaccccga tagtgcaaac cccgataact tattactaca    12960
ctgttatagt ggatgaagga caatttgcat taatagatta tcaagggagt ttcacagtcc    13020
tacccgcaca gagtcagccc gtgatattca ttacttctta tcctagaatt gggctattag    13080
gacaaacgat aactgtgact ttccagttca cttataatag tcccgtagcg aatgtaactc    13140
aatcagcgtt tacgcaatca tctaatattc tcgcttttgc ctatgcgaaa atggtaacaa    13200
caaacgctat agttcagttc aaggcgtatt ggctaagtgc taatgacggg ttggtgatta    13260
taactcaaac gaataactat ctaattccgt ttaatagcag tataacgggc ttaaacttcg    13320
caaacaatag tgttaatacg ttaacgtttc agattgtaac gggtaactat gtacaaataa    13380
ctagctcagc gggaggcgtg cttaccctaa gcaatactag tccgattata ggaataaggt    13440
tctattacgg ttccggtgtc ctacacctga actggttctt cgttagcggt atcatttttgc    13500 agtctgcaac ggcaaatcag gcttacgtta ttttgacggg gactaaccca aatacgcttt    13560
cacagtatac gacgggctat actaacgctt cggggttcgg tactgtaacg ctgaagttga    13620
gttacactcc ttacgaactt gtggatgtag actggtacgg cgttacatac gctttgttaa    13680
acattagcgt ttcaaacact actacagtaa gcagtactac gaccgtgaac acaacaacgc    13740
ttaactataa ctacactaag cctttcagca ataacatagc acctaacagt cagctttatg    13800
acttctcagc gtatcagccg tgggcggaaa ttatcggat tgtggtcgtg gtcgtcatag    13860
ctctgctggg ctggaagttc ggcgggtctg cgggagcttc gggtggtgcg gttatggggt    13920
taatcgcagt cagctactta ggtttactgc cttggtacct attctacatc ttcgtattcg    13980
gtatcgctct attacttgct aaagtatttg tagaccgttt catggggagg gaggaatgac    14040
ggacgcaatc agtttagcct tgcaaacggg cttagggccg gtggtagggg taattatcat    14100
actggcaatg atgggctaa cgtataagat agcgggaaag atcccggcaa tcataacggg    14160
aatagcctcg gctttcgtcc taatgtttat ggatttttta ccgttatttt ggggtatcgc    14220
aataatcttc gggttaatcg cgggtatggt ggtgacaagg gatggggact aagttagtcg    14280
tttacgtctt attgtttgac gtcttcctat cgttagtggt aggtgcctac tcgggtatag    14340
```

```
caccgccaag tattccaccg gtacctacat atgcttcagc ccaactcacg gcaagtctaa    14400
tcacatggac agtgggatgg cctcctatta cattatggcc tcagataacg cttattccgc    14460
cgttttcgat tttgggtgca aacttccccg gcttaaccat tcctagctta acgatacccg    14520
gtgtaacgct cttctcaata agcttcagct ggttagcccc aattatttat attgcaaatt    14580
ggatcatttg ggtctttcag actgttgcta gtgtgctatc ttatttactt aatatcttta    14640
cgggttcggt aggtctattg agtagtgtac ccgtcttagg gccattttg accgccttcg    14700 tgttgatagt taacttcgtg ttagtgtggg aattaatcaa gttaattagg gggtcggaat    14760
gacggagtat aacgcaaaca gtataagggc taagatactg aggcgtaaaa tccttcaact    14820
gattgcggaa aactacgttt tgtcagcgtc gttaatctct cacacactct tactctcata    14880
cgccacagtg cttaggcact tgcgtatcct taacgatgag ggctatatcg aattgtataa    14940
gcaaggtagg acgctatacg caaaaatccg cgataatgcg aaacaaattc agattctgaa    15000
ttcagaactg gagggttta aaaacgtaag cgggaagccg atattgacca aggatgagac    15060
tcctaaggag tttggcaaga agatagcct cactcaaaga ggctaaggtt gcactaaaag    15120
tagcaagcga ccccagaaag tacttcaacg aagaacagat gactgaggct tacaggatat    15180
tctggcagac atgggacggg gacataatta gaagtgctag aaggttcgtg gaagtagcaa    15240
aggcaaaccc caagctcaca aaaggtgaag caaccaacat aggcgtattg ttgggcttat    15300
tcatcttcat actaataggt atagtactat tgcccgtaat cgttagccaa gtcaacaacc    15360
tcacaagcgg tacttcaccc caagtaaccg gtactaacgc cacactcctg aacttagtgc    15420
cgttattcta tatcctagtc ctcataatag tccccgcagt cgtggcgtat aagatataca    15480
aagactgagg tgtgagggat ggaaatcagt ttaaagccaa tcattttttt ggtcgttttt    15540
atcatcgtag ggatagcact attcggccct ataaacagtg ttgtaaataa cgttaccaca    15600
tcgggaacct acactactat agtttccggt actgttacta cgtcttcatt tgtgtcaaat    15660
ccgcaatacg taggtagcaa taacgctact atcgtagcct tagtgccgtt attctatatc    15720
ctagtcctca taatagtccc cgcagtcgtg gcgtataagt tgtataagga ggagtgatat    15780
gaagtgggtg caaaaggcga taagagacc cgggagggta catcgctacc ttatgaggct    15840
ctacggcaaa cgggcgttta caaaagacgg tgacataaag gcaagttatc tcgataaggc    15900
gataaagcac gttaaaaaag ctaagatccc gaaagagaag aaacgtagtt tactgtcagc    15960
cctactgtta gcgaaaaggc ttaagcggat gcaccgcaag taggccctt ataaagtcat    16020 attctttttc tttccctgat gagtgcgtta ggggatgtaa tctacatctt gggttttctc    16080
tttccggctt tagggctaat cagccgaaac tatcttgtta acttaatggc attcataata    16140
ggaacagtcg ccttttttggt cttcgtccaa ggctataccg atatagcgtt cagcagttcg    16200 acgtttact taggagtact gcctctacta cttggtctcg tcaacttagg ctatttcttc    16260
aattggttga gggaggaaag gatatgaggt ggggtagaag agatgatagg gataccggca    16320
aaatacttcg aaataggagt cgtaatagat tcaacattta tcattatgtc tctactgtta    16380
agaaagtcaa agagacagag agagaactcc ttcgacttac gcaaacatgg aaggctatta    16440
ggcttatatc ttataatagc gtcggcatca gcattaatcg tctcacatct cgccttatac    16500
acaaactaca tgaactactt aacgggctta tctcttaatg cgtttctgtt ttatcttggg    16560
ttgaggtgtt tgcatgtctg atgggaaact cctttctgct ttcgaggagg aattaagaaa    16620
agcccaaagc ctagaggaat taagcaaaa gtatgaggaa gcccaaaaac aaatagctga    16680
cggcaaagta ctaaagaggc tatacaaggt ttatgagaaa aggcaaacag aattaatgct    16740
```

```
tcagcaatat aggcagataa aggctgaact ggaaaagagg aaaaaggtaa agaaaaagga    16800
taaagccgac ataagggtta gagtagtaaa gaagtgdata aattcacgct tattcagtgc    16860
tgagcattac gtcgcattac tgcaagaaaa tcaagacggc ttatcgatac tatttctaag    16920
aagagcaaaa cttatagaaa atcaaggcta tctaatgcta gaagtgaaga agttaaggaa    16980
ggcatgggtt ttaacggctg aacctatact ccttgaaagg ttaaaattcc cattcggcaa    17040
aaagtttgta gccgtgcatt tcgttttacc caattatcct tacacacttc agcttaaacc    17100
ggatgaaaaa ctgaaagagt tagcagttaa ggcgataaac gggcctcaaa taatgagcgc    17160
aatgatacgt acaaagttct tcgaagcgtt agctagggta ggaagcgggc ctgatctgat    17220
gatgctcata atcggcgttg tcatggggat tggcataggc gtagcgatag gtttcggtat    17280
agctaacgca aacttaacgc atttgctatc tcaacacgtt acgaacacta cagtgacaca    17340
tactacgacc acaacgactt caccctcatt cacgattccc tcaaactcct caaaaggggt    17400
gagctaaaat ggtctcagta acagaaataa taacatatgg acgagaagca atagaaagaa    17460
taatatgcaa atattttaaa gattcgaaaa tagaaaagat attattcttg ccgagtgagg    17520
aagacgtaaa ggcaaaatat atcattggac gggtagggtt tataaggatt agtaatacgt    17580
ggtctggaat tgtcgtagtt gacggggtac aaatacctt cgttgctgaa gtccaccta    17640 atggcaagat tgatatttac ctttatcctc aaaaggactt ctacttagca catttggtgg    17700
gtgagctgaa tggctaaaaa gaacggctta acagaactag agcaattaaa gaaagagaac    17760
gaagagttga gaaagaagtt agaagagtta gaggcgttga tcaataacga tagcgatgac    17820
gacgaagagt tgcaggaaat cgaaaacccg tacaccgtta caaccgtgc aatagatgaa    17880 ttagtaagcc caaaggacac aatgttctat ttgtcgggaa accagatatc gttaatctta    17940
agtgcttttg aattcgcccg cttaccgacg tacttcggtg aggaaccggt aacggagtta    18000
gcggaatacg cccataagtt gaaacattat ctcgtttcga aaggaggaag aggaaggagg    18060
gatatactga gagtcctacg cgttagttca ggtcagacaa gagagaacgt aaacaaatca    18120
attctgaaac aattatttga ccatggtaag gaacatgaag atgaagaaga gtaatgaatg    18180
gttatggtta gggactaaaa ttataaacgc ccataagact aacggctttg aaagtgcgat    18240
tattttcggg aaacaaggta cgggaaagac tacttacgcc cttaaggtgg caaaagaagt    18300
ttaccagaga ttaggacatg aaccggacaa ggcatgggaa ctggccccttg actctttatt    18360 ctttgagctt aaagatgcat tgaggataat gaaaatattc aggcaaaatg ataggacaat    18420
accaataata atttcgacg atgctgggat atggcttcaa aaatatttat ggtataagga    18480
agagatgata aagttttacc gtatatataa cattattagg aatatagtaa gcggggtgat    18540
cttcactacc ccttcccta acgatatagc gttttatgtg agggaaaagg ggtggaagct    18600
gataatgata acgagaaacg gaagacaacc tgacggtacg ccaaaggcag tagctaaaat    18660
agcggtgaat aagataacga ttataaaagg aaaaataaca aataagatga aatgaggac    18720 agtagacgat tatacggtca agcttccgga ttgggtatat aaagaatatg tggaaagaag    18780
aaaggtttat gaggaaaaat tgttggagga gttggatgag gttttagata gtgataacaa    18840
aacgaaaaac ccgtcaaacc catcactact aacgaaaatt gacgacgtaa caagatagtg    18900
atacgggtaa tgtcagaccc cttttagcca ttccgcatac ttttatatt gctctttcgc    18960 tatgccgaag agcgatacgt aatgttgcgt taaaacgcgt gtcggtttac gcccttgaat    19020
aaaatcgata atatctaacg gtacgcttag ctcagccatc ttagacgcta cgaatttgcg    19080
```

-continued

```
gaagtacttt atcgctatag cgtccttatg acgtcgttca aagtccgcta ttgcccactt    19140
cgtcacctct actctcttca gaggcgttat gtggaataca tagaagacgc ccttatatcc    19200
cctagtccaa ctaagcggat aataacagac gtcgttaccg caaatgtccc tttcgggttc    19260
cttcagcact ttcagtattt cgctcagcct aacgcccgac tcgagagcga tacggtagat    19320
gaagtagacg ttttcgctat agtcttttgc taattgtaac gtccttttta tctcttccaa    19380
cgttggaatg tagatatcag cgttcgcctt cttcaccttt accgctttca atattttatc    19440
cgcaaattca tcatgtatga tattgcgtga cgctaagaaa cgtgcaaaga gtcggtaagc    19500
cttctgtgcg tctctcgtct ctttatacgg ctttgatata gcattgatgt agtcctttgc    19560
agttttttcg cttatccccc tttcgttcat gagatagtcg tagaacgcct ttatgttgcc    19620
gtccgtcgcg tattggcgca aattggcaac caacgctatt ttacgtcgtt cagttccctc    19680
ttttccgcct ccggagccgg aggtcccggg ttcaaatccc ggcgggtccg cttgtagggg    19740
agtatcccct acgaccccta atttcatttt tagatatgat tcaacgacgt cagctaaagg    19800
acccacgtaa cgctctttta cctcaccgtt ttcatactct agcttgtaaa cataataccg    19860
cccttttcctc tcgcgtaaaa tataatcccc gtatttataa cgcgtcttat ctttcgtcat    19920
ttcgcctcac agtattatgg ttgccaaaac gggcttataa gcattggcaa cccgttaatt    19980
tttgccgtta aaacacgttg aattgaaaga agacggcaaa gaatccacac aggtaatact    20040
aaaaaagtag tattacttac attagaagga ctcatttgtc caccttgtat tctagccatg    20100
ctatctctgc cttcagctca tctagcttcc cctttatgtc tgtcaggtca aggggaactc    20160
ctctcattaa cctgagttcg ttttcgattt tttcaagctc cttttccaac tcctctagtt    20220
tctctaattc ctttagtcgt tcttccaatt tcttttccaa tttccccttt gcgtcattta    20280
taattatgct tactacccaa acaattccta aatcagaaat aattattaac tcctctgagt    20340
tgaatatcat tttccgcccc tcgctaaata ctccttaaag ctctgataga accccttcag    20400
actaacccgt aagtctgtta ggttcttcca gtattgtaat gggattaagt aatagtagct    20460
tactgcatct ctctcaaatt tgtccttctt aatctttcct tgcttttcta agttgagtat    20520
ttgcagtgct gagatacatt ttaacttgtc ctcagcatct gaatagtgta taaaccaaac    20580
cctccccata acctcattct gctttgcaac ttctacttta gtgcttaata ttgcgtaaac    20640
gctttcgccg tatctttctt tgctctgttc ttcagtccat gaacttcccg taatatctat    20700
ccaaattaaa ggataatatt ctgtcttagc cttaacgtat aaagtcaaat cgtatttatc    20760
ttgcagaccg ctatagtatt gctcatttat tacattagtt aaagtcccca cgccagttgg    20820
gcggatataa acatcaaagt ctaacaaacc cttagcccgc cactttgata aagagattaa    20880
gagcttttcca aaaactaggt attctcgccc taaataagtt gaagggagga tataatcctc    20940
agcttgatta ccccaatact ttagcttaaa attagtttca gccatctcac tcaccatatt    21000
gaaacgtggg ctagtatgtg aatcagtact gatgctattg caaataacac acttgcagta    21060
gcaattccta ttacaatcca tttaccataa tccaccttag tttgttggtc aatatactcg    21120
ttgatgatct ttagtatttc tggctttagt tctgataatg aaaggaagac agaggcataa    21180
agtactaagg aggatgtgaa cagattatcc gccttttctg aaagtttata aagctcatat    21240
cttgctctct cataatcttc ataattaata atttcatcaa acttttctac ttgctcttca    21300
tattctttct tcagagagta aggagttgtc ttttcaatta ctcctaattt tattaacttc    21360
ttaacagctt ccttaaatcc ttgttttattg ctagcatacg ctaaagggtc ttttccttct    21420
tgagaagctc tatagataac tatagcacca taaacaatat ttacaatatc gtatggtaag    21480
```

```
gaatacgcac cgatttgggc aatatcttca actcttcttt gatccatcta gttcacctct   21540
ttttgatttg tttgtaggtt tctatcgcag ttttcagcga tatcgcaaat agcttcccct   21600
tttccgttag gtatagcctc ttttcgcctc tttcttgacg ctctttcacg aagccctctt   21660
gtattaggaa ctttttttgca tcataaaagg tggcagtgga catgggaaat tctgcgttta   21720
ctttcttgta taggtcatat gttgctattc cttcattatc atatagataa gccaatacta   21780
tggcttcggg gtagaagaat ggtgtacttt tcatatcctc ctcactcctc agcctctaat   21840
agcttaactg cctcctctat caactgtccc attgtctttc cagtctttgc cttaagcctc   21900
tgcagtaaat ggtaaaaaga ttttacttat tccgttctct tctgagaacc gcttgctttt   21960
tacgattaaa ttccacatat catctaagat agagtgttgt ggttctagct tcctcgtgta   22020
gattttcccc tattaatgtt agtttataaa gaccggctat ttttttcacta att          22073
```

<210> SEQ ID NO 11
<211> LENGTH: 21706
<212> TYPE: DNA
<213> ORGANISM: Artificial Sequence
<220> FEATURE:
<223> OTHER INFORMATION: synthetic vector nucleotide sequence

<400> SEQUENCE: 11

```
tcatttttc ctaaaaattg ctcctttaca tttcatcacc ttatcctcga taatcttatt     60
tatagttctt aatgctgtta atggattccc tgcattataa atacttcttc caatgatttc    120
ataatccgct ccagcacata ctgcatcgcc ataacttcca ccttgactac ccatacccgg    180
agagactatg gtcatttttt cgaagtctct cctatactgc gttatatgat ctaatttagt    240
ccctccaact actattcctt tgggcttat ctctctttata acgttttttaa tatagtctgc    300 gaataacgta ctccatcctt catgtgacat tacggcaact aagtataaat ttttagagtt    360
tgcatcaaga tatcttttta attcatctag agatccctta acgcctataa aggaatgtgc    420
tatgaacgag ttggcgaaag ataatctttc aactatgctt ttcattatgt atccgatatc    480
tgcaagctta aaatcaacaa taatttcctc cacgtctaaa ccaattaaga gctctctagt    540
tttatccact cctagatcta aaactaaagg taaaccaact tttatcccat ataactcatt    600
ttccatctct ttaagaactt gatatgagag aggtttatcc attgctaata ttactctact    660
tttcaacatt cttcaccaaa taatctagaa ttgacttctt ttcattatcc ttaagtttat    720
cactcttcaa caattcatct agaatttctg aaattttaaa tagagagtgt aatttgactc    780
ctagtttttc caatctttgt gaagccccctt cttgtctatc tatgattact agtgcgtctg    840
aaactttacc tccaccgtta agaatctcca atgttgcttt ctctatggat actcctgtag    900
ttgcaacgtc atctactaac aatactcttt ttcctttttac atcgagttct aatgtacgat    960
tagttccatg accttttcttt tctattctaa tatatcccat aggctcttta aggttacaag   1020
ctatgaatgc cgataaggga actcctccag tggctattcc tactattata tcatggggta   1080
tatcttttgc tttctttata gcttgattaa ctatatcgta aaattctgga taatttggta   1140
aaggtcttaa gtctaagtaa tatggactaa ccttacctga tgttaaaacg aaacttccta   1200
ttaataataa tttcctttcg agtaagactt ctgcgaaatt catacgtaga gactctgcga   1260
aaaagaattt aaatatactt ctatcataac cagttataag ggctttgtga gattaagaca   1320
cgtagtttcg tcgcttgact tgaccagaga tgactacttt agaatattcg aacttgcaga   1380
caagttctat gatgtaaaaa aactaaatta tctatcaggg aaagtagttt cattagcatt   1440
```

```
ctttgagcca agtactagaa ctgctcaaag ctttcatact gcagcaataa aattaggtgc    1500
tgatgtgata ggatttgcat ccgaggagtc tacttcgata gcaaaaggtg aaaatttggc    1560
tgataccatt aggatgctaa acaactattc aaactgtatt gtaatgagac ataagtttga    1620
tggggcagca ttattcccta gtccagtgtg gtggaattct gcagatatca acaagtttgt    1680
acaaaaaagc tgaacgagaa acgtaaaatg atataaatat caatatatta aattagattt    1740
tgcataaaaa acagactaca taatactgta aaacacaaca tatccagtca ctatggcggc    1800
cgcattaggc accccaggct ttacacttta tgcttccggc tcgtataatg tgtggatttt    1860
gagttaggat ccggtcgaga ttttcaggag ctaaggaagc taaatggag aaaaaaatca    1920 ctggatatac caccgttgat atatcccaat ggcatcgtaa agaacatttt gaggcatttc    1980
agtcagttgc tcaatgtacc tataaccaga ccgttcagct ggatattacg gcctttttaa    2040
agaccgtaaa gaaaaataag cacaagtttt atccggcctt tattcacatt cttgcccgcc    2100
tgatgaatgc tcatccggaa ttccgtatgg caatgaaaga cggtgagctg gtgatatggg    2160
atagtgttca cccttgttac accgttttcc atgagcaaac tgaaacgttt tcatcgctct    2220
ggagtgaata ccacgacgat ttccggcagt ttctacacat atattcgcaa gatgtggcgt    2280
gttacggtga aaacctggcc tatttcccta aagggtttat tgagaatatg ttttcgtct    2340 cagccaatcc ctgggtgagt ttcaccagtt ttgatttaaa cgtggccaat atggacaact    2400
tcttcgcccc cgttttcacc atgggcaaat attatacgca aggcgacaag gtgctgatgc    2460
cgctggcgat tcaggttcat catgccgttt gtgatggctt ccatgtcgg cagaatgctt    2520 aatgaattac aacagtactg cgatgagtgg cagggcgggg cgtaaagatc tggatccggc    2580
ttactaaaag ccagataaca gtatgcgtat ttgcgcgctg attttgcgg tataagaata    2640 tatactgata tgtatacccg aagtatgtca aaaagaggta tgctatgaag cagcgtatta    2700
cagtgacagt tgacagcgac agctatcagt tgctcaaggc atatatgatg tcaatatctc    2760
cggtctggta agcacaacca tgcagaatga agcccgtcgt ctgcgtgccg aacgctggaa    2820
agcggaaaat caggaaggga tggctgaggt cgcccggttt attgaaatga acggctcttt    2880
tgctgacgag aacaggggct ggtgaaatgc agtttaaggt ttacacctat aaaagagaga    2940
gccgttatcg tctgtttgtg gatgtacaga gtgatattat tgacacgccc gggcgacgga    3000
tggtgatccc cctggccagt gcacgtctgc tgtcagataa agtctcccgt gaactttacc    3060
cggtggtgca tatcggggat gaaagctggc gcatgatgac caccgatatg gccagtgtgc    3120
cggtctccgt tatcggggaa gaagtggctg atctcagcca ccgcgaaaat gacatcaaaa    3180
acgccattaa cctgatgttc tggggaatat aaatgtcagg ctcccttata cacagccagt    3240
ctgcaggtcg accatagtga ctggatatgt tgtgttttac agtattatgt agtctgtttt    3300
ttatgcaaaa tctaatttaa tatattgata tttatatcat tttacgtttc tcgttcagct    3360
ttcttgtaca aagtggttga tatccagcac agtggcgccg ccgccaccg cggtggagct    3420 cgaattcgta atcatgtcat agctgtttcc tgtgtgaaat tgttatccgc tcacaattcc    3480
acacaacata cgagccggaa gcataaagtg taaagcctgg ggtgcctaat gagtgagcta    3540
actcacatta attgcgttgc gctcactgcc cgctttccag tcgggaaacc tgtcgtgcca    3600
gctgcattaa tgaatcggcc aacgcgcggg gagaggcggt ttgcgtattg ggcgctcttc    3660
cgcttcctcg ctcactgact cgctgcgctc ggtcgttcgg ctgcggcgag cggtatcagc    3720
tcactcaaag gcggtaatac ggttatccac agaatcaggg gataacgcag gaaagaacat    3780
gtgagcaaaa ggccagcaaa aggccaggaa ccgtaaaaag gccgcgttgc tggcgttttt    3840
```

```
ccataggctc cgcccccctg acgagcatca caaaaatcga cgctcaagtc agaggtggcg    3900
aaacccgaca ggactataaa gataccaggc gtttccccct ggaagctccc tcgtgcgctc    3960
tcctgttccg accctgccgc ttaccggata cctgtccgcc tttctccctt cgggaagcgt    4020
ggcgctttct catagctcac gctgtaggta tctcagttcg gtgtaggtcg ttcgctccaa    4080
gctgggctgt gtgcacgaac ccccgttca gcccgaccgc tgcgccttat ccggtaacta     4140
tcgtcttgag tccaacccgg taagacacga cttatcgcca ctggcagcag ccactggtaa    4200
caggattagc agagcgaggt atgtaggcgg tgctacagag ttcttgaagt ggtggcctaa    4260
ctacggctac actagaagga cagtatttgg tatctgcgct ctgctgaagc cagttacctt    4320
cggaaaaaga gttggtagct cttgatccgg caaacaaacc accgctggta gcggtggttt    4380
ttttgtttgc aagcagcaga ttacgcgcag aaaaaaagga tctcaagaag atcctttgat    4440
cttttctacg ggtctgacg ctcagtggaa cgaaaactca cgttaaggga ttttggtcat     4500
gagattatca aaaaggatct tcacctagat ccttttaaat taaaaatgaa gttttaaatc    4560
aatctaaagt atatatgagt aaacttggtc tgacagttac caatgcttaa tcagtgaggc    4620
acctatctca gcgatctgtc tatttcgttc atccatagtt gcctgactcc ccgtcgtgta    4680
gataactacg atacgggagg gcttaccatc tggccccagt gctgcaatga taccgcgaga    4740
cccacgctca ccggctccag atttatcagc aataaaccag ccagccggaa gggccgagcg    4800
cagaagtggt cctgcaactt tatccgcctc catccagtct attaattgtt gccgggaagc    4860
tagagtaagt agttcgccag ttaatagttt gcgcaacgtt gttgccattg ctacaggcat    4920
cgtggtgtca cgctcgtcgt ttggtatggc ttcattcagc tccggttccc aacgatcaag    4980
gcgagttaca tgatccccca tgttgtgcaa aaaagcggtt agctccttcg gtcctccgat    5040
cgttgtcaga agtaagttgg ccgcagtgtt atcactcatg gttatggcag cactgcataa    5100
ttctcttact gtcatgccat ccgtaagatg cttttctgtg actggtgagt actcaaccaa    5160
gtcattctga gaatagtgta tgcggcgacc gagttgctct tgcccggcgt caatacggga    5220
taataccgcg ccacatagca gaactttaaa agtgctcatc attggaaaac gttcttcggg    5280
gcgaaaactc tcaaggatct taccgctgtt gagatccagt tcgatgtaac ccactcgtgc    5340
acccaactga tcttcagcat cttttacttt caccagcgtt tctgggtgag caaaaacagg    5400
aaggcaaaat gccgcaaaaa agggaataag ggcgacacgg aaatgttgaa tactcatact    5460
cttcctttt caatattatt gaagcattta tcagggttat tgtctcatga gcggatacat     5520
atttgaatgt atttagaaaa ataaacaaat aggggttccg cgcacatttc cccgaaaagt    5580
gccacctgac gtctaagaaa ccattattat catgacatta acctataaaa ataggcgtat    5640
cacgaggccc tttcgtctcg cgcgtttcgg tgatgacggt gaaaacctct gacacatgca    5700
gctcccggag acggtcacag cttgtctgta agcggatgcc gggagcagac aagcccgtca    5760
gggcgcgtca gcgggtgttg gcgggtgtcg ggctggctt aactatgcgg catcagagca     5820
gattgtactg agagtgcacc atatgcggtg tgaaataccg cacagatgcg taaggagaaa    5880
ataccgcatc aggcgccatt cgccattcag gctgcgcaac tgttgggaag ggcgatcggt    5940
gcgggcctct tcgctattac gccagctggc gaaaggggga tgtgctgcaa ggcgattaag    6000
ttgggtaacg ccagggtttt cccagtcacg acgttgtaaa acgacggcca gtgccaagct    6060
tgcatgcctg cagagtctca tatgtttcct cacttattga aatgttaagc cttttgacta    6120
tcctatcttt cctcttctct atcatttagg tcaccttgtt tattgttatt tgaaatacgt    6180
```

```
atccgtcttc gtcacatcga agtataattt tgtatccatt attagcatat tctacgtcaa    6240
agttcccaca acaataattc gggtcttcgg actcgttata gactttgctc caaccatctt    6300
tttgtagtgc ctcttctaag tagtctactc tgatgaagcc ttcatcatat tcgttcagta    6360
ccctaaagct tatactatca atgcctaata cgtctaatag cttcaacaga tcgaatatag    6420
gaacttgcac catcatttca gctcacctta atgagctgat ataattccgc ttctatcttt    6480
tgaacttgga agtatgcctt gcctagcttt tgcttatcca tattgcccgt tattctatca    6540
atcttaatct cgtggattaa tgataatagc tctctgacat cctcatcaag catttcaaat    6600
aattctttct ctaagacttc tttactcatt gttttcacc ttagcaaact catctaacgt     6660
tgtttgtctc agttctcttt tctttatcaa ataaaattcc gaatgtccct tcttattgtt    6720
attactgtac ttcatgtcag ttcactgctt tgcctttata aatccttgat ccgtttgctc    6780
aaaatttgcg ggctgggcat caaatatctt agctatattg tcttgtgttt gctcttgttt    6840
ttgttcttct ttctgctctt gcttaatcca tttgaacgtt gtctttctgt ttttgtattg    6900
tacttcacac tcgtctggat gtctttcgca aatagctttc aatgctctct gtatgttata    6960
cgcactcggg actgaaatct caaattgagc tagtatatcc tctaacgtta attcaccttt    7020
cttttcaaga atttatataca ttatttccgc catcttgtat gaatttagag tttgtgccat   7080
attcccatcc cactctatct atactctatg tataaattag tatttaagtc ttactctatc    7140
tatactctat ctatctctct atatacacag tgtttgggta actggcaaaa ttctgtctga    7200
ctgctgtctg acaagagttt actctatctc tctatatcta tatacacaaa cagagttagt    7260
cgactctgtg tatcttatgt atcttataca aaaaatatgg gatgtgcaaa atctgagcta    7320
ctaatactgc ttgaatatat agatagagag tgtaaggact acgagagttg taaaagaata    7380
atagtagagc tagaagagag agtgaagaaa atagctttcg tagaagcaat aaatgatttg    7440
ttctaaacta cttttttctc tctatctcta tatctatata tatacataac taaaactaaa    7500
agaataaaca aaaactaac aaaatcaact caccattata caaactcaga aaaactattt     7560
ttttgttata ctcttacccc atatatatat agatatatag atagagagag atagagtata    7620
gtagggcatt taagatttta gaagttcttc aatgcgtctt ctgattgcat ctgcaacaaa    7680
ctcttgtctg cttatatatc cgcccttgcc tgacgctatt agttcatcta tttgttttgc    7740
taattcgatt ggaatcgaaa cggtcacata ttctttttg actgatttcc tcggcatacg     7800
ctatctatac tatattaata tgataatatt aaatgattca cgatatatag atagagtata    7860
gatagagtaa agtttaaata cttatataga tagagtatag atagagggtt caaaaaatgg    7920
tttcacccca aacccgaaaa gaagaagagt tattagaaaa acaaaattca gttttttatt    7980
tgttaacttt aggaaggaaa ccgtatggtt catatttgca tataaaaatt gaactagacg    8040
aagatgaaaa attagagaag gaaatctatg cggataacat taagctagag aatgaattaa    8100
gacaactgaa gaggttgtat gaagtatatc agagcgtaga gattgacgat gctcagaaag    8160
caatacagaa ggaagcatta ctgacgatag cgaaaatact aagtgttttt gacttctgag    8220
gaggctgagg ggcaatgaag gctgaggaaa caatcgtgga acagattcag gacataattc    8280
aaaaacttcg ctattataca ggaagatcaa atagacattt caagatgatt agaaactatt    8340
atgaggagtg tataataata gtagacgctg aggagtttat acaagaaaat aacactctaa    8400
gcattactgt atattctgag gatcttatat attatactgt tgatatcccg ctgaatttca    8460
ttaaacatgt attcgtatcc gcttcgattg atcagctcaa tgatcagctt cagctaaaat    8520
ataatgaggg tctgattaga gtttctctta ctttgaacga tgacttatgt gagaaactga    8580
```

```
gaagctcata ctgcggtgat attacattct ttaatgaggc tgaggggcaa tgaaggctag    8640
ggttgaatac atcaaattac ctagatgtta cacaaaaact tatagaaaaa tcgaagcgaa    8700
aaagaacaac gacggtacaa tagaattaac gttagaggaa acaatgcaag taatatcctt    8760
taaactaccc ccggcgttaa atgcaaaact agaacaaatt gcgatcaaag aaaagaaaag    8820
caagagtgaa attattcgaa tagcgttagc gaggtatgta gaaaatgttt agatgcccca    8880
tctgcgggtt caaaacgctg agattgttcg cgcttaaaca acatactcga agggagcatg    8940
tgttggtcaa atgtcccata tgcgggttca cggggaagca tttatctcaa catttctata    9000
gtaggtatga tattgaccat ctcatatact gctacctatt ctcttctttc agattgccta    9060
agaatgttag gttagcaata aagagaaaat tagaggttga gtgaataatg tatcaatgtc    9120
tacgttgtgg tggtatattt aataaaagaa gagaagtggt tgagcatttg cttgtagggc    9180
ataagcacaa ggatagacta acactggact tttattatat ctacttcagg gtgagaggac    9240
aatgaaccta attgatatca tcttatttta cggctttcaa ttcaacgatt attggacaac    9300
tgtcttaggg ttgagagtgg gtgcggaaga gaagaatccc atagcgggtc tgttcatttc    9360
atcaccgtat cgtttagcgt tgtttaagtt tggccttatc accattggta tgtttatatt    9420
aatttatgtt gttagattca agacatggac agagatcgta ttgactgtaa cagacgttgt    9480
cgaatgcctt gtcacgctga ataatacccct tacgattagg aggtacaaaa ggaggggcgt    9540
tagaggatga cggagtcaga cgttgactca ggtagtaaaa aatacctgag taaccataag    9600
gggattttta ttcatgtcac actggaagag ttaaagcgtt accaccaact tacgccggaa    9660
cagaagaggt tgataagggc aatcgtcaaa acgcttattc ataacccgca actgttggat    9720
gaaagcagtt atctttacag attgctcgcg agtaaagcga tttcacagtt tgtctgcccg    9780 cttttgtctaa tgcccttcag ctcttccgta tcactaaagc aacacatccg ttatactgaa    9840
cacacaaagg tttgcccggt gtgtaaaaag gagtttacct caaccgattc agccctagac    9900
catgtttgca aaaagcataa tatctgcgtt agttaggctc tttttaaagt ctaccttctt    9960
tttcgcttac aatgaggaag tcccttctag ccctactaac cctatcccta gcgttactat   10020 cgttttttaat aacaccatcg atggcattga attctggcgg ttcaccgata ccgatatatt   10080
ataactatta taactactat agccttaacg cagaagggtt tggattcagt ttcaataata   10140
gcaataattg ggttgaaacg aactttatct caataaccat aaacttacct agttcattac   10200
caaataacta tcaaatcaat aatgcctatt ctatcgtagt aggattatca ccatatccgg   10260
ttagcaatat aaacattttt aatagcccat tagaagcata tgttgaacta ttctcaaacc   10320
caccgaatac atatccaaat gaaataggat ttgtagttag ttacggctca actgtatttt   10380
atagttatac cacactgtat agcagttttg cgggcacaca actaacaata actatatcat   10440
ataccggaaa tgggtttggt gtgcaattct ctgacagtaa cgggttctct cactcagttt   10500
cggtaagttc ggtaaacttt gtaccatatg gtgctctaat actcggatca ctaatcccga   10560
acgggaacta ttactactac ccagtaggta acatgttacc gaatgcatcg gtgaacttct   10620
catatacgat ctcaagtttc acaatagaag gaaacccggc cacatccgtc gatattacca   10680
cacttggatt agaggaaac actgcaatat atacttcaag tagcaattgg ttcaaatggg   10740
tatccggtag tgtggttatc acaaatgccg ttgcctatac ctataccgat ttggctagaa   10800
taggaggaag tgcacaaata aactatactg catcgcagct atattaagca aaatcttttt   10860
ttacctcttt ttaaatctgt cttatatgaa aaaactgttt acagttgtag gttctatttt   10920
```

```
ctctggtttg gggatttggc ttaagtcaat agaccagtca ttttatttaa cgaaagtatt   10980
gtataacgga aaagtaattg aaatagttct aacgcccgag acaaatgaag tcgtgaaatc   11040
ttccaacggt gttatgaacg caagtgtaac ttctctacct tccacaattc tataccaagc   11100
acaatccgtg ccttcaataa atggaggaac tcttagtgta ataaatacca cagttcaacc   11160
gccatggtat gctaacttat ggcctgaagt cttaacaata ggtatagtga tgttgggaat   11220
tgcaatattc agctggatta aacttaaatt tagaagatag ccctttttaa agccataaat   11280
ttttatcgc ttaatgaagt ggggactatt attcttaata atgtttatat ccattttttc    11340
cctcaactct ttagccctat aatcggcgg aggagggccc aacaataatg gtgcgggagt    11400
ttacactcag actataacag ttaacggagg aaccgtacga actactctta acggttcaac   11460
gctttctacc gcaccatggc tcaacccctc ttacgtaagc gtctacaaca catactacct   11520
tcaggttttg ccgaaccaag agtatattga caacaacgtt tcgttatccc taaatacggc   11580
taacattgcg ttaaacgtca cttggttatt ggcgtcctca agcaatacgg gatcctacgg   11640
tgcaatcgcc ataggctacg gagtgaactt tcccgcgggg tttgtcaata actacggtcc   11700
ttccgcacct tacacgccgg acggaatcgt aatatatctc atgaaaggag gcatgccgac   11760
ctatcgttta ttcgtatact tcaatggagt tgagcagtta aacgtttcag tcgggtcaat   11820
cagtgtggga caaaaaatag gtttagggtt cttttatcta cagaacacac tttacgttta   11880
ctactataac ggtactttaa agacttggtc attaacgccc ggtacgctga ttactataaa   11940
tagtaattac gttatagacg cacagaatat agggccgggc tacggctacg gtcaatgggt   12000
aatagttaat tatcaatatg cgatgccggt tactgcacaa ctgacggtta gttatttcgc   12060
attagggtac aatgtatatc atttcttaat ggcttatgcg ggtgctggaa acccggtaaa   12120
cataactgcg aataacgggg cttcttacag tataacgggt atagttgcag agaagaactt   12180
tacgataacg ggaattcagc aaggcctagc ctatgctttc agcttgttag ggaaaccgaa   12240
tggcttatac ttattatata tggggccaat tgagggcagc ccaccaacgt ggtatgtaaa   12300
cgtaaccgta gggcttcaga tcgttacacc ccagaaaacg ataaactaca acttaacaat   12360
accagtaatc gttgagggct atgcgttata cccttctgtt aacgtacctt ccggaactta   12420
cctaagcgga cagactatta gctttaccct ctcatcgttc ttgggatacc cttcaggctt   12480
aggctattac accgcagtaa atctaatcgc aaacgtaaca ataaacggtg tgagtcatgc   12540
tatcccctat agtttcaccc cgatagtgca aaccccgata acttattact acactgttat   12600
agtggatgaa ggacaatttg cattaataga ttatcaaggg agtttcacag tcctaccgc    12660
acagagtcag cccgtgatat tcattacttc ttatcctaga attgggctat taggacaaac   12720
gataactgtg actttccagt tcacttataa tagtcccgta gcgaatgtaa ctcaatcagc   12780
gtttacgcaa tcatctaata ttctcgcttt tgcctatgcg aaaatggtaa caacaaacgc   12840
tatagttcag ttcaaggcgt attggctaag tgctaatgac gggttggtga ttataactca   12900
aacgaataac tatctaattc cgtttaatag cagtataacg ggcttaaact cgcaaacaa    12960
tagtgttaat acgttaacgt ttcagattgt aacgggtaac tatgtacaaa taactagctc   13020
agcgggaggc gtgcttaccc taagcaatac tagtccgatt ataggaatag ggttctatta   13080
cggttccggt gtcctacacc tgaactggtt cttcgttagc ggtatcattt tgcagtctgc   13140
aacggcaaat caggcttacg ttattttgac ggggactaac ccaaatacgc tttcacagta   13200
tacgacgggc tatactaacg cttcgggggtt cggtactgta acgctgaagt tgagttacac   13260
tccttacgaa cttgtggatg tagactggta cggcgttaca tacgctttgt taaacattag   13320
```

```
cgtttcaaac actactacag taagcagtac tacgaccgtg aacacaacaa cgcttaacta   13380
taactacact aagcctttca gcaataacat agcacctaac agtcagcttt atgacttctc   13440
agcgtatcag ccgtgggcgg aaattatcgg gattgtggtc gtggtcgtca tagctctgct   13500
gggctggaag ttcggcgggt ctgcgggagc ttcgggtggt gcggttatgg ggttaatcgc   13560
agtcagctac ttaggtttac tgccttggta cctattctac atcttcgtat tcggtatcgc   13620
tctattactt gctaaagtat ttgtagaccg tttcatgggg agggaggaat gacgacgca   13680 atcagtttag ccttgcaaac gggcttaggg ccggtggtag gggtaattat catactggca   13740
atgatggggc taacgtataa gatagcggga aagatcccgg caatcataac gggaatagcc   13800
tcggctttcg tcctaatgtt tatggatttt ttaccgttat tttggggtat cgcaataatc   13860
ttcgggttaa tcgcgggtat ggtggtgaca agggatgggg actaagttag tcgtttacgt   13920
cttattgttt gacgtcttcc tatcgttagt ggtaggtgcc tactcgggta tagcaccgcc   13980
aagtattcca ccggtaccta catatgcttc agcccaactc acggcaagtc taatcacatg   14040
gacagtggga tggcctccta ttacattatg gcctcagata acgcttattc cgccgttttc   14100
gattttgggt gcaaacttcc ccggcttaac cattcctagc ttaacgatac ccggtgtaac   14160
gctcttctca ataagcttca gctggttagc cccaattatt tatattgcaa attggatcat   14220
ttgggtcttt cagactgttg ctagtgtgct atcttattta cttaatatct ttacgggttc   14280
ggtaggtcta ttgagtagtg tacccgtctt agggccattt ttgaccgcct tcgtgttgat   14340
agttaacttc gtgttagtgt gggaattaat caagttaatt aggggggtcgg aatgacggag   14400 tataacgcaa acagtataag ggctaagata ctgaggcgta aaatccttca actgattgcg   14460
gaaaactacg ttttgtcagc gtcgttaatc tctcacacac tcttactctc atacgccaca   14520
gtgcttaggc acttgcgtat ccttaacgat gagggctata tcgaattgta taagcaaggt   14580
aggacgctat acgcaaaaat ccgcgataat gcgaaacaaa ttcagattct gaattcagaa   14640
ctggaggggt ttaaaaacgt aagcgggaag ccgatattga ccaaggatga gactcctaag   14700
gagtttggca agaaagatag cctcactcaa agaggctaag gttgcactaa agtagcaag   14760 cgaccccaga aagtacttca acgaagaaca gatgactgag gcttacagga tattctggca   14820
gacatgggac ggggacataa ttagaagtgc tagaaggttc gtggaagtag caaaggcaaa   14880
ccccaagctc acaaaaggtg aagcaaccaa cataggcgta ttgttgggct tattcatctt   14940
catactaata ggtatagtac tattgcccgt aatcgttagc caagtcaaca acctcacaag   15000
cggtacttca ccccaagtaa ccggtactaa cgccacactc ctgaacttag tgccgttatt   15060
ctatatccta gtcctcataa tagtccccgc agtcgtggcg tataagatat acaaagactg   15120
aggtgtgagg gatggaaatc agtttaaagc caatcatttt tttggtcgtt tttatcatcg   15180
tagggatagc actattcggc cctataaaca gtgttgtaaa taacgttacc acatcgggaa   15240
cctacactac tatagtttcc ggtactgtta ctacgtcttc atttgtgtca atccgcaat   15300 acgtaggtag caataacgct actatcgtag ccttagtgcc gttattctat atcctagtcc   15360
tcataatagt ccccgcagtc gtggcgtata agttgtataa ggaggagtga tatgaagtgg   15420
gtgcaaaagg cgataaagag acccgggagg gtacatcgct accttatgag gctctacggc   15480
aaacgggcgt ttacaaaaga cggtgacata aaggcaagtt atctcgataa ggcgataaag   15540
cacgttaaaa aagctaagat cccgaaagag aagaaacgta gtttactgtc agccctactg   15600
ttagcgaaaa ggcttaagcg gatgcaccgc aagtaggccc tttataaagt catattcttt   15660
```

```
ttctttccct gatgagtgcg ttaggggatg taatctacat cttgggtttt ctctttccgg   15720
ctttagggct aatcagccga aactatcttg ttaacttaat ggcattcata ataggaacag   15780
tcgccttttt ggtcttcgtc caaggctata ccgatatagc gttcagcagt tcgacgtttt   15840
acttaggagt actgcctcta ctacttggtc tcgtcaactt aggctatttc ttcaattggt   15900
tgagggagga aaggatatga ggtggggtag aagagatgat agggataccg gcaaaatact   15960
tcgaaatagg agtcgtaata gattcaacat ttatcattat gtctctactg ttaagaaagt   16020
caaagagaca gagagagaac tccttcgact tacgcaaaca tggaaggcta ttaggcttat   16080
atcttataat agcgtcggca tcagcattaa tcgtctcaca tctcgcctta tacacaaact   16140
acatgaacta cttaacgggc ttatctctta atgcgtttct gttttatctt gggttgaggt   16200
gtttgcatgt ctgatgggaa actcctttct gctttcgagg aggaattaag aaaagcccaa   16260
agcctagagg aattaaagca aaagtatgag gaagcccaaa aacaaatagc tgacggcaaa   16320
gtactaaaga ggctatacaa ggtttatgag aaaaggcaaa cagaattaat gcttcagcaa   16380
tataggcaga taaaggctga actggaaaag aggaaaaagg taaagaaaaa ggataaagcc   16440
gacataaggg ttagagtagt aaagaagtgg ataaattcac gcttattcag tgctgagcat   16500
tacgtcgcat tactgcaaga aaatcaagac ggcttatcga tactatttct aagaagagca   16560
aaacttatag aaaatcaagg ctatctaatg ctagaagtga agaagttaag gaaggcatgg   16620
gttttaacgg ctgaacctat actccttgaa aggttaaaat tcccattcgg caaaaagttt   16680
gtagccgtgc atttcgtttt acccaattat ccttacacac ttcagcttaa accggatgaa   16740
aaactgaaag agttagcagt taaggcgata acgggcctc aaataatgag cgcaatgata   16800
cgtacaaagt tcttcgaagc gttagctagg gtaggaagcg ggcctgatct gatgatgctc   16860
ataatcggcg ttgtcatggg gattggcata ggcgtagcga taggtttcgg tatagctaac   16920
gcaaacttaa cgcatttgct atctcaacac gttacgaaca ctacagtgac acatactacg   16980
accacaacga cttcaccctc attcacgatt ccctcaaact cctcaaaagg ggtgagctaa   17040
aatggtctca gtaacagaaa taataacata tggacgagaa gcaatagaaa gaataatatg   17100
caaatatttt aaagattcga aaatagaaaa gatattattc ttgccgagtg aggaagacgt   17160
aaaggcaaaa tatatcattg gacgggtagg gtttataagg attagtaata cgtggtctgg   17220
aattgtcgta gttgacgggg tacaaatacc tttcgttgct gaagtccacc ttaatggcaa   17280
gattgatatt tacctttatc ctcaaaagga cttctactta gcacatttgg tgggtgagct   17340
gaatggctaa aaagaacggc ttaacagaac tagagcaatt aaagaaagag aacgaagagt   17400
tgagaaagaa gttagaagag ttagaggcgt tgatcaataa cgatagcgat gacgacgaag   17460
agttgcagga aatcgaaaac ccgtacaccg ttacaaaccg tgcaatagat gaattagtaa   17520
gcccaaagga cacaatgttc tatttgtcgg gaaaccagat atcgttaatc ttaagtgctt   17580
ttgaattcgc ccgcttaccg acgtacttcg gtgaggaacc ggtaacggag ttagcggaat   17640
acgcccataa gttgaaacat tatctcgttt cgaaaggagg aagaggaagg agggatatac   17700
tgagagtcct acgcgttagt tcaggtcaga caagagagaa cgtaaacaaa tcaattctga   17760
aacaattatt tgaccatggt aaggaacatg aagatgaaga agagtaatga atggttatgg   17820
ttagggacta aaattataaa cgcccataag actaacggct ttgaaagtgc gattattttc   17880
gggaaacaag gtacgggaaa gactacttac gcccttaagg tggcaaaaga agtttaccag   17940
agattaggac atgaaccgga caaggcatgg gaactggccc ttgactcttt attctttgag   18000
cttaaagatg cattgaggat aatgaaaata ttcaggcaaa atgataggac aataccaata   18060
```

```
ataattttcg acgatgctgg gatatggctt caaaaatatt tatggtataa ggaagagatg   18120
ataaagtttt accgtatata taacattatt aggaatatag taagcggggt gatcttcact   18180
accccttccc ctaacgatat agcgttttat gtgagggaaa aggggtggaa gctgataatg   18240
ataacgagaa acggaagaca acctgacggt acgccaaagg cagtagctaa aatagcggtg   18300
aataagataa cgattataaa aggaaaaata acaaataaga tgaaatggag gacagtagac   18360
gattatacgg tcaagcttcc ggattgggta tataaagaat atgtggaaag aagaaaggtt   18420
tatgaggaaa aattgttgga ggagttggat gaggttttag atagtgataa caaaacggaa   18480
aacccgtcaa acccatcact actaacgaaa attgacgacg taacaagata gtgatacggg   18540
taatgtcaga ccccttttag ccattccgca tactttttat attgctcttt cgctatgccg   18600
aagagcgata cgtaatgttg cgttaaaacg cgtgtcggtt tacgcccttg aataaaatcg   18660
ataatatcta acggtacgct tagctcagcc atcttagacg ctacgaattt gcggaagtac   18720
tttatcgcta tagcgtcctt atgacgtcgt tcaaagtccg ctattgccca cttcgtcacc   18780
tctactctct tcagaggcgt tatgtggaat acatagaaga cgcccttata tcccctagtc   18840
caactaagcg gataataaca gacgtcgtta ccgcaaatgt cccttttcggg ttccttcagc   18900 actttcagta tttcgctcag cctaacgccc gactcgagag cgatacggta gatgaagtag   18960
acgttttcgc tatagtcttt tgctaattgt aacgtccttt ttatctcttc caacgttgga   19020
atgtagatat cagcgttcgc cttcttcacc tttaccgctt tcaatatttt atccgcaaat   19080
tcatcatgta tgatattgcg tgacgctaag aaacgtgcaa agagtcggta agccttctgt   19140
gcgtctctcg tctctttata cggctttgat atagcattga tgtagtcctt tgcagttttt   19200
tcgcttatcc ccctttcgtt catgagatag tcgtagaacg cctttatgtt gccgtccgtc   19260
gcgtattggc gcaaattggc aaccaacgct attttacgtc gttcagttcc ctcttttccg   19320
cctccggagc cggaggtccc gggttcaaat cccggcgggt ccgcttgtag gggagtatcc   19380
cctacgaccc ctaatttcat ttttagatat gattcaacga cgtcagctaa aggacccacg   19440
taacgctctt ttacctcacc gttttcatac tctagcttgt aaacataata ccgccctttc   19500
ctctcgcgta aaatataatc cccgtattta taacgcgtct tatctttcgt catttcgcct   19560
cacagtatta tggttgccaa aacgggctta taagcattgg caacccgtta attttgccg    19620 ttaaaacacg ttgaattgaa agaagacggc aaagaatcca cacaggtaat actaaaaaag   19680
tagtattact tacattagaa ggactcattt gtccaccttg tattctagcc atgctatctc   19740
tgccttcagc tcatctagct tccccttat gtctgtcagg tcaagggaa ctcctctcat     19800 taacctgagt tcgttttcga ttttttcaag ctccttttcc aactcctcta gtttctctaa   19860
ttcctttagt cgttcttcca atttcttttc caatttcccc tttgcgtcat ttataattat   19920
gcttactacc caaacaattc ctaaatcaga ataattatt aactcctctg agttgaatat    19980
cattttccgc ccctcgctaa atactcctta aagctctgat agaacccctt cagactaacc   20040
cgtaagtctg ttaggttctt ccagtattgt aatgggatta agtaatagta gcttactgca   20100
tctctctcaa atttgtcctt cttaatcttt ccttgctttt ctaagttgag tatttgcagt   20160
gctgagatac atttaacttt gtcctcagca tctgaatagt gtataaacca aaccctcccc   20220
ataacctcat tctgctttgc aacttctact ttagtgctta atattgcgta aacgctttcg   20280
ccgtatcttt ctttgctctg ttcttcagtc catgaacttc ccgtaatatc tatccaaatt   20340
aaaggataat attctgtctt agccttaacg tataaagtca aatcgtattt atcttgcaga   20400
```

```
ccgctatagt attgctcatt tattacatta gttaaagtcc ccacgccagt tgggcggata    20460
taaacatcaa agtctaacaa acccttagcc cgccactttg ataaagagat taagagcttt    20520
ccaaaaacta ggtattctcg ccctaaataa gttgaaggga ggatataatc ctcagcttga    20580
ttaccccaat actttagctt aaaattagtt tcagccatct cactcaccat attgaaacgt    20640
gggctagtat gtgaatcagt actgatgcta ttgcaaataa cacacttgca gtagcaattc    20700
ctattacaat ccatttacca taatccacct tagtttgttg gtcaatatac tcgttgatga    20760
tctttagtat ttctggcttt agttctgata atgaaaggaa gacagaggca taaagtacta    20820
aggaggatgt gaacagatta tccgcctttt ctgaaagttt ataaagctca tatcttgctc    20880
tctcataatc ttcataatta ataatttcat caaacttttc tacttgctct tcatattctt    20940
tcttcagaga gtaaggagtt gtcttttcaa ttactcctaa ttttattaac ttcttaacag    21000
cttccttaaa tccttgttta ttgctagcat acgctaaagg gtcttttcct tcttgagaag    21060
ctctatagat aactatagca ccataaacaa tatttacaat atcgtatggt aaggaatacg    21120
caccgatttg ggcaatatct tcaactcttc tttgatccat ctagttcacc tctttttgat    21180
ttgtttgtag gtttctatcg cagttttcag cgatatcgca aatagcttcc ccttttccgt    21240
taggtatagc ctcttttcgc ctctttcttg acgctctttc acgaagccct cttgtattag    21300 gaacttttt gcatcataaa aggtggcagt ggacatggga aattctgcgt ttactttctt    21360
gtataggtca tatgttgcta ttccttcatt atcatataga taagccaata ctatggcttc    21420
ggggtagaag aatggtgtac ttttcatatc ctcctcactc ctcagcctct aatagcttaa    21480
ctgcctcctc tatcaactgt cccattgtct ttccagtctt tgccttaagc ctctgcagta    21540
aatggtaaaa agattttact tattccgttc tcttctgaga accgcttgct ttttacgatt    21600
aaattccaca tatcatctaa gatagagtgt tgtggttcta gcttcctcgt gtagattttc    21660
ccctattaat gttagtttat aaagaccggc tattttttca ctaatt              21706

<210> SEQ ID NO 12
<211> LENGTH: 22015
<212> TYPE: DNA
<213> ORGANISM: Artificial Sequence
<220> FEATURE:
<223> OTHER INFORMATION: synthetic vector nucleotide sequence

<400> SEQUENCE: 12
tcattttttc ctaaaaattg ctcctttaca tttcatcacc ttatcctcga taatcttatt       60
tatagttctt aatgctgtta atggattccc tgcattataa atacttcttc caatgatttc      120
ataatccgct ccagcacata ctgcatcgcc ataacttcca ccttgactac ccatacccgg      180
agagactatg gtcatttttt cgaagtctct cctatactgc gttatatgat ctaatttagt      240
ccctccaact actattcctt tgggcttat ctctcttata acgttttaa tatagtctgc      300 gaataacgta ctccatcctt catgtgacat tacggcaact aagtataaat ttttagagtt      360
tgcatcaaga tatcttttta attcatctag agatcccta acgcctataa aggaatgtgc      420
tatgaacgag ttggcgaaag ataatctttc aactatgctt tcattatgt atccgatatc      480 tgcaagctta aaatcaacaa taatttcctc cacgtctaaa ccaattaaga gctctctagt      540
tttatccact cctagatcta aaactaaagg taaaccaact tttatcccat ataactcatt      600
ttccatctct ttaagaactt gatatgagag aggtttatcc attgctaata ttactctact      660
tttcaacatt cttcaccaaa taatctagaa ttgacttctt ttcattatcc ttaagtttat      720
cactcttcaa caattcatct agaatttctg aaattttaaa tagagagtgt aatttgactc      780
```

```
ctagtttttc caatctttgt gaagcccctt cttgtctatc tatgattact agtgcgtctg     840
aaactttacc tccaccgtta agaatctcca atgttgcttt ctctatggat actcctgtag     900
ttgcaacgtc atctactaac aatactcttt ttccttttac atcgagttct aatgtacgat     960
tagttccatg acctttcttt tctattctaa tatatcccat aggctcttta aggttacaag    1020
ctatgaatgc cgataaggga actcctccag tggctattcc tactattata tcatggggta    1080
tatcttttgc tttctttata gcttgattaa ctatatcgta aaattctgga taatttggta    1140
aaggtcttaa gtctaagtaa tatggactaa ccttacctga tgttaaaacg aaacttccta    1200
ttaataataa tttcctttcg agtaagactt ctgcgaaatt catacgtaga gactctgcga    1260
aaagaatttt aaatatactt ctatcataac cagttataag ggctttgtga gattaagaca    1320
cgtagtttcg tcgcttgact tgaccagaga tgactacttt agaatattcg aacttgcaga    1380
caagttctat gatgtaaaaa aactaaatta tctatcaggg aaagtagttt cattagcatt    1440
ctttgagcca agtactagaa ctgctcaaag ctttcatact gcagcaataa aattaggtgc    1500
tgatgtgata ggatttgcat ccgaggagtc tacttcgata gcaaaaggtg aaaatttggc    1560
tgataccatt aggatgctaa acaactattc aaactgtatt gtaatgagac ataagtttga    1620
tggggcagca ttattcccta ggggccccat ctggaaaaat aatgaggaga gtatttagag    1680
atgaagctta aagatctta gataatctga gtttgatctt ttatgtgcat tgtggtcatg    1740

ttgaattttc acgatcattt aaggactccc ataaacataa attatgtatc aaaacattaa    1800

ttgaaatata gataatagtt atattatagt tatтттттaga aaaacatcca atatgttaac    1860
aaaacgtctt ttacggaaat atataaatgt taaacaagtt aggtatacta tttataaaat    1920
agttaggtca taaagtacc cgagaactag tccagtgtgg tggaattctg cagatatcaa    1980
caagtttgta caaaaaagct gaacgagaaa cgtaaaatga tataaatatc aatatattaa    2040
attagatttt gcataaaaaa cagactacat aatactgtaa aacacaacat atccagtcac    2100

tatggcggcc gcattaggca ccccaggctt tacactttat gcttccggct cgtataatgt    2160 gtggatttt g agttaggatc cggtcgagat tttcaggagc taaggaagct aaaatggaga    2220
aaaaaatcac tggatatacc accgttgata tatcccaatg gcatcgtaaa gaacattttg    2280 aggcaттттca gtcagttgct caatgtacct ataaccagac cgttcagctg gatattacgg    2340
cctttttaaa gaccgtaaag aaaaataagc acaagtttta tccggcctt attcacattc    2400

ttgcccgcct gatgaatgct catccggaat tccgtatggc aatgaaagac ggtgagctgg    2460

tgatatggga tagtgttcac ccttgttaca ccgttttcca tgagcaaact gaaacgtttt    2520
catcgctctg gagtgaatac cacgacgatt tccggcagtt tctacacata tattcgcaag    2580
atgtggcgtg ttacggtgaa aacctggcct atttccctaa agggtttatt gagaatatgt    2640

tttcgtctc agccaatccc tgggtgagtt tcaccagttt tgatttaaac gtggccaata    2700

tggacaactt cttcgccccc gttttcacca tgggcaaata ttatacgcaa ggcgacaagg    2760

tgctgatgcc gctggcgatt caggttcatc atgccgtttg tgatggcttt ccatgtcggc    2820
agaatgctta atgaattaca acagtactgc gatgagtggc agggcggggc gtaaagatct    2880
ggatccggct tactaaaagc cagataacag tatgcgtatt tgcgcgctga tttttgcggt    2940
ataagaatat atactgatat gtatacccga agtatgtcaa aaagaggtat gctatgaagc    3000
agcgtattac agtgacagtt gacagcgaca gctatcagtt gctcaaggca tatatgatgt    3060
caatatctcc ggtctggtaa gcacaaccat gcagaatgaa gcccgtcgtc tgcgtgccga    3120
```

```
acgctggaaa gcggaaaatc aggaagggat ggctgaggtc gcccggttta ttgaaatgaa    3180
cggctctttt gctgacgaga acaggggctg gtgaaatgca gtttaaggtt tacacctata    3240
aaagagagag ccgttatcgt ctgtttgtgg atgtacagag tgatattatt gacacgcccg    3300
ggcgacggat ggtgatcccc ctggccagtg cacgtctgct gtcagataaa gtctcccgtg    3360
aactttaccc ggtggtgcat atcggggatg aaagctggcg catgatgacc accgatatgg    3420
ccagtgtgcc ggtctccgtt atcggggaag aagtggctga tctcagccac cgcgaaaatg    3480
acatcaaaaa cgccattaac ctgatgttct ggggaatata aatgtcaggc tcccttatac    3540
acagccagtc tgcaggtcga ccatagtgac tggatatgtt gtgttttaca gtattatgta    3600
gtctgttttt tatgcaaaat ctaatttaat atattgatat ttatatcatt ttacgtttct    3660
cgttcagctt tcttgtacaa agtggttgat atccagcaca gtggcgccgg ccgccaccgc    3720
ggtggagctc gaattcgtaa tcatgtcata gctgtttcct gtgtgaaatt gttatccgct    3780
cacaattcca cacaacatac gagccggaag cataaagtgt aaagcctggg gtgcctaatg    3840
agtgagctaa ctcacattaa ttgcgttgcg ctcactgccc gctttccagt cgggaaacct    3900
gtcgtgccag ctgcattaat gaatcggcca acgcgcgggg agaggcggtt tgcgtattgg    3960
gcgctcttcc gcttcctcgc tcactgactc gctgcgctcg tcgttcggc tgcggcgagc    4020 ggtatcagct cactcaaagg cggtaatacg gttatccaca gaatcagggg ataacgcagg    4080
aaagaacatg tgagcaaaag gccagcaaaa ggccaggaac cgtaaaaagg ccgcgttgct    4140
ggcgtttttc cataggctcc gcccccctga cgagcatcac aaaaatcgac gctcaagtca    4200
gaggtggcga aacccgacag gactataaag ataccaggcg tttccccctg gaagctccct    4260
cgtgcgctct cctgttccga ccctgccgct taccggatac ctgtccgcct ttctcccttc    4320
gggaagcgtg gcgctttctc atagctcacg ctgtaggtat ctcagttcgg tgtaggtcgt    4380
tcgctccaag ctgggctgtg tgcacgaacc ccccgttcag cccgaccgct gcgccttatc    4440
cggtaactat cgtcttgagt ccaacccggt aagacacgac ttatcgccac tggcagcagc    4500
cactggtaac aggattagca gagcgaggta tgtaggcggt gctacagagt tcttgaagtg    4560
gtggcctaac tacggctaca ctagaaggac agtatttggt atctgcgctc tgctgaagcc    4620
agttaccttc ggaaaaagag ttggtagctc ttgatccggc aaacaaacca ccgctggtag    4680
cggtggtttt tttgtttgca agcagcagat tacgcgcaga aaaaaaggat ctcaagaaga    4740
tcctttgatc ttttctacgg ggtctgacgc tcagtggaac gaaaactcac gttaagggat    4800
tttggtcatg agattatcaa aaaggatctt cacctagatc cttttaaatt aaaaatgaag    4860
ttttaaatca atctaaagta tatatgagta aacttggtct gacagttacc aatgcttaat    4920
cagtgaggca cctatctcag cgatctgtct atttcgttca tccatagttg cctgactccc    4980
cgtcgtgtag ataactacga tacgggaggg cttaccatct ggccccagtg ctgcaatgat    5040
accgcgagac ccacgctcac cggctccaga tttatcagca ataaaccagc cagccggaag    5100
ggccgagcgc agaagtggtc ctgcaacttt atccgcctcc atccagtcta ttaattgttg    5160
ccgggaagct agagtaagta gttcgccagt taatagtttg cgcaacgttg ttgccattgc    5220
tacaggcatc gtggtgtcac gctcgtcgtt tggtatggct tcattcagct ccggttccca    5280
acgatcaagg cgagttacat gatccccat gttgtgcaaa aaagcggtta gctccttcgg    5340
tcctccgatc gttgtcagaa gtaagttggc cgcagtgtta tcactcatgg ttatggcagc    5400
actgcataat tctcttactg tcatgccatc cgtaagatgc ttttctgtga ctggtgagta    5460
ctcaaccaag tcattctgag aatagtgtat gcggcgaccg agttgctctt gcccggcgtc    5520
```

```
aatacgggat aataccgcgc cacatagcag aactttaaaa gtgctcatca ttggaaaacg    5580
ttcttcgggg cgaaaactct caaggatctt accgctgttg agatccagtt cgatgtaacc    5640
cactcgtgca cccaactgat cttcagcatc ttttactttc accagcgttt ctgggtgagc    5700
aaaaacagga aggcaaaatg ccgcaaaaaa gggaataagg gcgacacgga aatgttgaat    5760
actcatactc ttcctttttc aatattattg aagcatttat cagggttatt gtctcatgag    5820
cggatacata tttgaatgta tttagaaaaa taaacaaata ggggttccgc gcacatttcc    5880
ccgaaaagtg ccacctgacg tctaagaaac cattattatc atgacattaa cctataaaaa    5940
taggcgtatc acgaggccct ttcgtctcgc gcgtttcggt gatgacggtg aaaacctctg    6000
acacatgcag ctcccggaga cggtcacagc ttgtctgtaa gcggatgccg ggagcagaca    6060
agcccgtcag ggcgcgtcag cgggtgttgg cgggtgtcgg gctggctta actatgcggc     6120 atcagagcag attgtactga gagtgcacca tatgcggtgt gaaataccgc acagatgcgt    6180
aaggagaaaa taccgcatca ggcgccattc gccattcagg ctgcgcaact gttgggaagg    6240
gcgatcggtg cgggcctctt cgctattacg ccagctggcg aaagggggat gtgctgcaag    6300
gcgattaagt tgggtaacgc cagggttttc ccagtcacga cgttgtaaaa cgacggccag    6360
tgccaagctt gcatgcctgc agagtctcat atgtttcctc acttattgaa atgttaagcc    6420
ttttgactat cctatctttc ctcttctcta tcatttaggt caccttgttt attgttattt    6480
gaaatacgta tccgtcttcg tcacatcgaa gtataatttt gtatccatta ttagcatatt    6540
ctacgtcaaa gttcccacaa caataattcg ggtcttcgga ctcgttatag actttgctcc    6600
aaccatcttt ttgtagtgcc tcttctaagt agtctactct gatgaagcct tcatcatatt    6660
cgttcagtac cctaaagctt atactatcaa tgcctaatac gtctaatagc ttcaacagat    6720
cgaatatagg aacttgcacc atcatttcag ctcaccttaa tgagctgata taattccgct    6780
tctatctttt gaacttggaa gtatgccttg cctagctttt gcttatccat attgcccgtt    6840
attctatcaa tcttaatctc gtggattaat gataatagct ctctgacatc ctcatcaagc    6900
atttcaaata attctttctc taagacttct ttactcattg tttttcacct tagcaaactc    6960
atctaacgtt gtttgtctca gttctctttt ctttatcaaa taaaattccg aatgtccctt    7020
cttattgtta ttactgtact tcatgtcagt tcactgcttt gcctttataa atccttgatc    7080
cgtttgctca aaatttgcgg gctgggcatc aaatatctta gctatattgt cttgtgtttg    7140
ctcttgtttt tgttcttctt tctgctcttg cttaatccat ttgaacgttg tctttctgtt    7200
tttgtattgt acttcacact cgtctggatg tctttcgcaa atagctttca atgctctctg    7260
tatgttatac gcactcggga ctgaaatctc aaattgagct agtatatcct ctaacgttaa    7320
ttcacctttc ttttcaagaa ttttatacat tatttccgcc atcttgtatg aatttagagt    7380
ttgtgccata ttcccatccc actctatcta tactctatgt ataaattagt atttaagtct    7440
tactctatct atactctatc tatctctcta tatacacagt gtttgggtaa ctggcaaaat    7500
tctgtctgac tgctgtctga caagagttta ctctatctct ctatatctat atacacaaac    7560
agagttagtc gactctgtgt atcttatgta tcttatacaa aaaatatggg atgtgcaaaa    7620
tctgagctac taatactgct tgaatatata gatagagagt gtaaggacta cgagagttgt    7680
aaaagaataa tagtagagct agaagagaga gtgaagaaaa tagctttcgt agaagcaata    7740
aatgatttgt tctaaactac tttttctctc ctatctctat atctatatat atacataact    7800
aaaactaaaa gaataaacaa aaaactaaca aaatcaactc accattatac aaactcagaa    7860
```

| | | | | | |
|---|---|---|---|---|---|
| aaactattttt | tttgttatac | tcttacccca | tatatatata | gatatataga | tagagagaga | 7920 |
| tagagtatag | tagggcattt | aagattttag | aagttcttca | atgcgtcttc | tgattgcatc | 7980 |
| tgcaacaaac | tcttgtctgc | ttatatatcc | gcccttgcct | gacgctatta | gttcatctat | 8040 |
| ttgttttgct | aattcgattg | gaatcgaaac | ggtcacatat | tcttttttga | ctgatttcct | 8100 |
| cggcatacgc | tatctatact | atattaatat | gataatatta | aatgattcac | gatatataga | 8160 |
| tagagtatag | atagagtaaa | gtttaaatac | ttatatagat | agagtataga | tagagggttc | 8220 |
| aaaaaatggt | ttcaccccaa | acccgaaaag | aagaagagtt | attagaaaaa | caaaattcag | 8280 |
| tttttattt | gttaacttta | ggaaggaaac | cgtatggttc | atatttgcat | ataaaaattg | 8340 |
| aactagacga | agatgaaaaa | ttagagaagg | aaatctatgc | ggataacatt | aagctagaga | 8400 |
| atgaattaag | acaactgaag | aggttgtatg | aagtatatca | gagcgtagag | attgacgatg | 8460 |
| ctcagaaagc | aatacagaag | gaagcattac | tgacgatagc | gaaaatacta | agtgttttg | 8520 |
| acttctgagg | aggctgaggg | gcaatgaagg | ctgaggaaac | aatcgtggaa | cagattcagg | 8580 |
| acataattca | aaaacttcgc | tattatacag | gaagatcaaa | tagacatttc | aagatgatta | 8640 |
| gaaactatta | tgaggagtgt | ataataatag | tagacgctga | ggagtttata | caagaaaata | 8700 |
| acactctaag | cattactgta | tattctgagg | atcttatata | ttatactgtt | gatatcccgc | 8760 |
| tgaatttcat | taaacatgta | ttcgtatccg | cttcgattga | tcagctcaat | gatcagcttc | 8820 |
| agctaaaata | taatgagggt | ctgattagag | tttctcttac | tttgaacgat | gacttatgtg | 8880 |
| agaaactgag | aagctcatac | tgcggtgata | ttacattctt | taatgaggct | gaggggcaat | 8940 |
| gaaggctagg | gttgaataca | tcaaattacc | tagatgttac | acaaaaactt | atagaaaaat | 9000 |
| cgaagcgaaa | aagaacaacg | acggtacaat | agaattaacg | ttagaggaaa | caatgcaagt | 9060 |
| aatatccttt | aaactacccc | cggcgttaaa | tgcaaaacta | gaacaaattg | cgatcaaaga | 9120 |
| aaagaaaagc | aagagtgaaa | ttattcgaat | agcgttagcg | aggtatgtag | aaaatgttta | 9180 |
| gatgccccat | ctgcgggttc | aaaacgctga | gattgttcgc | gcttaaacaa | catactcgaa | 9240 |
| gggagcatgt | gttggtcaaa | tgtcccatat | gcgggttcac | ggggaagcat | ttatctcaac | 9300 |
| atttctatag | taggtatgat | attgaccatc | tcatatactg | ctacctattc | tcttctttca | 9360 |
| gattgcctaa | gaatgttagg | ttagcaataa | agagaaaatt | agaggttgag | tgaataatgt | 9420 |
| atcaatgtct | acgttgtggt | ggtatattta | ataaaagaag | agaagtggtt | gagcatttgc | 9480 |
| ttgtagggca | taagcacaag | gatagactaa | cactggactt | ttattatatc | tacttcaggg | 9540 |
| tgagaggaca | atgaacctaa | ttgatatcat | cttattttac | ggctttcaat | tcaacgatta | 9600 |
| ttggacaact | gtcttagggt | tgagagtggg | tgcggaagag | aagaatccca | tagcgggtct | 9660 |
| gttcatttca | tcaccgtatc | gtttagcgtt | gtttaagttt | ggccttatca | ccattggtat | 9720 |
| gtttatatta | atttatgttg | ttagattcaa | gacatggaca | gagatcgtat | tgactgtaac | 9780 |
| agacgttgtc | gaatgccttg | tcacgctgaa | taatacccct | acgattagga | ggtacaaaag | 9840 |
| gagggggcgtt | agaggatgac | ggagtcagac | gttgactcag | gtagtaaaaa | ataccctgagt | 9900 |
| aaccataagg | ggattttat | tcatgtcaca | ctggaagagt | taaagcgtta | ccaccaactt | 9960 |
| acgccggaac | agaagaggtt | gataagggca | atcgtcaaaa | cgcttattca | taacccgcaa | 10020 |
| ctgttggatg | aaagcagtta | tctttacaga | ttgctcgcga | gtaaagcgat | ttcacagttt | 10080 |
| gtctgcccgc | tttgtctaat | gcccttcagc | tcttccgtat | cactaaagca | acacatccgt | 10140 |
| tatactgaac | acacaaaggt | ttgccggtg | tgtaaaaagg | agtttacctc | aaccgattca | 10200 |
| gccctagacc | atgtttgcaa | aaagcataat | atctgcgtta | gttaggctct | ttttaaagtc | 10260 |

```
taccttctttt ttcgcttaca atgaggaagt cccttctagc cctactaacc ctatccctag   10320
cgttactatc gtttttaata acaccatcga tggcattgaa ttctggcggt tcaccgatac   10380
cgatatatta taactattat aactactata gccttaacgc agaagggttt ggattcagtt   10440
tcaataatag caataattgg gttgaaacga actttatctc aataaccata aacttaccta   10500
gttcattacc aaataactat caaatcaata atgcctattc tatcgtagta ggattatcac   10560
catatccggt tagcaatata aacattttta atagcccatt agaagcatat gttgaactat   10620
tctcaaaccc accgaataca tatccaaatg aaataggatt tgtagttagt tacggctcaa   10680
ctgtatttta tagttatacc acactgtata gcagttttgc gggcacacaa ctaacaataa   10740
ctatatcata taccggaaat gggtttggtg tgcaattctc tgacagtaac gggttctctc   10800
actcagtttc ggtaagttcg gtaaactttg taccatatgg tgctctaata ctcggatcac   10860
taatcccgaa cgggaactat tactactacc cagtaggtaa catgttaccg aatgcatcgg   10920
tgaacttctc atatacgatc tcaagtttca caatagaagg aaacccggcc acatccgtcg   10980
atattaccac acttggatta gaaggaaaca ctgcaatata tacttcaagt agcaattggt   11040
tcaaatgggt atccggtagt gtggttatca caaatgccgt tgcctatacc tataccgatt   11100
tggctagaat aggaggaagt gcacaaataa actatactgc atcgcagcta tattaagcaa   11160 aatcttttt tacctctttt taaatctgtc ttatatgaaa aaactgttta cagttgtagg   11220
ttctattttc tctggtttgg ggatttggct taagtcaata gaccagtcat tttatttaac   11280
gaaagtattg tataacggaa aagtaattga aatagttcta acgcccgaga caaatgaagt   11340
cgtgaaatct tccaacggtg ttatgaacgc aagtgtaact tctctaccct ccacaattct   11400
ataccaagca caatccgtgc cttcaataaa tggaggaact cttagtgtaa taataccac   11460 agttcaaccg ccatggtatg ctaacttatg gcctgaagtc ttaacaatag gtatagtgat   11520
gttgggaatt gcaatattca gctggattaa acttaaattt agaagatagc cttttaaa    11580 gccataaatt ttttatcgct taatgaagtg gggactatta ttcttaataa tgtttatatc   11640 catttttttcc ctcaactctt tagccctatt aatcggcgga ggagggccca acaataatgg   11700
tgcgggagtt tacactcaga ctataacagt taacggagga accgtacgaa ctactcttaa   11760
cggttcaacg ctttctaccg caccatggct caacccctct tacgtaagcg tctacaacac   11820
atactacctt caggttttgc cgaaccaaga gtatattgac aacaacgttt cgttatccct   11880
aaatacggct aacattgcgt taaacgtcac ttggttattg gcgtcctcaa gcaatacggg   11940
atcctacggt gcaatcgcca taggctacgg agtgaacttt cccgcggggt tgtcaataa    12000 ctacggtcct tccgcacctt acacgccgga cggaatcgta atatatctca tgaaaggagg   12060
catgccgacc tatcgtttat tcgtatactt caatggagtt gagcagttaa acgtttcagt   12120
cgggtcaatc agtgtgggac aaaaaatagg tttagggttc ttttatctac agaacacact   12180
ttacgtttac tactataacg gtactttaaa gacttggtca ttaacgcccg gtacgctgat   12240
tactataaat agtaattacg ttatagacgc acagaatata gggccgggct acggctacgg   12300
tcaatgggta atagttaatt atcaatatgc gatgccggtt actgcacaac tgacggttag   12360
ttatttcgca ttagggtaca atgtatatca tttcttaatg gctatgcgg gtgctggaaa   12420 cccggtaaac ataactgcga ataacggggc ttcttacagt ataacgggta tagttgcaga   12480
gaagaacttt acgataacgg gaattcagca aggcctagcc tatgctttca gcttgttagg   12540
gaaaccgaat ggcttatact tattatatat ggggccaatt gagggcagcc caccaacgtg   12600
```

```
gtatgtaaac gtaaccgtag ggcttcagat cgttacaccc cagaaaacga taaactacaa  12660
cttaacaata ccagtaatcg ttgagggcta tgcgttatac ccttctgtta acgtaccttc  12720
cggaacttac ctaagcggac agactattag ctttaccctc tcatcgttct tgggataccc  12780
ttcaggctta ggctattaca ccgcagtaaa tctaatcgca aacgtaacaa taaacggtgt  12840
gagtcatgct atcccctata gtttcacccc gatagtgcaa accccgataa cttattacta  12900
cactgttata gtggatgaag gacaatttgc attaatagat tatcaaggga gtttcacagt  12960
cctacccgca cagagtcagc ccgtgatatt cattacttct tatcctagaa ttgggctatt  13020
aggacaaacg ataactgtga cttccagtt cacttataat agtcccgtag cgaatgtaac  13080
tcaatcagcg tttacgcaat catctaatat tctcgctttt gcctatgcga aaatggtaac  13140
aacaaacgct atagttcagt tcaaggcgta ttggctaagt gctaatgacg ggttggtgat  13200
tataactcaa acgaataact atctaattcc gtttaatagc agtataacgg gcttaaactt  13260
cgcaaacaat agtgttaata cgttaacgtt tcagattgta acgggtaact atgtacaaat  13320
aactagctca gcgggaggcg tgcttaccct aagcaatact agtccgatta taggaatagg  13380
gttctattac ggttccggtg tcctacacct gaactggttc ttcgttagcg gtatcatttt  13440
gcagtctgca acggcaaatc aggcttacgt tattttgacg gggactaacc caaatacgct  13500
ttcacagtat acgacgggct atactaacgc ttcggggttc ggtactgtaa cgctgaagtt  13560
gagttacact ccttacgaac ttgtggatgt agactggtac ggcgttacat acgctttgtt  13620
aaacattagc gtttcaaaca ctactacagt aagcagtact acgaccgtga acacaacaac  13680
gcttaactat aactacacta agcctttcag caataacata gcacctaaca gtcagcttta  13740
tgacttctca gcgtatcagc cgtgggcgga aattatcggg attgtggtcg tggtcgtcat  13800
agctctgctg ggctggaagt tcggcgggtc tgcgggagct tcgggtggtg cggttatggg  13860
gttaatcgca gtcagctact taggtttact gccttggtac ctattctaca tcttcgtatt  13920
cggtatcgct ctattacttg ctaaagtatt tgtagaccgt ttcatgggga gggaggaatg  13980
acggacgcaa tcagtttagc cttgcaaacg ggcttagggc cggtggtagg ggtaattatc  14040
atactggcaa tgatggggct aacgtataag atagcgggaa agatcccggc aatcataacg  14100
ggaatagcct cggctttcgt cctaatgttt atggattttt taccgttatt ttgggggtatc  14160 gcaataatct tcgggttaat cgcgggtatg gtggtgacaa gggatgggga ctaagttagt  14220
cgtttacgtc ttattgtttg acgtcttcct atcgttagtg gtaggtgcct actcgggtat  14280
agcaccgcca agtattccac cggtacctac atatgcttca gcccaactca cggcaagtct  14340
aatcacatgg acagtgggat ggcctcctat tacattatgg cctcagataa cgcttattcc  14400
gccgttttcg attttgggtg caaacttccc cggcttaacc attcctagct taacgatacc  14460
cggtgtaacg ctcttctcaa taagcttcag ctggttagcc ccaattattt atattgcaaa  14520
ttggatcatt tgggtctttc agactgttgc tagtgtgcta tcttatttac ttaatatctt  14580
tacgggttcg gtaggtctat tgagtagtgt acccgtctta gggccatttt tgaccgcctt  14640
cgtgttgata gttaacttcg tgttagtgtg ggaattaatc aagttaatta gggggtcgga  14700
atgacggagt ataacgcaaa cagtataagg gctaagatac tgaggcgtaa aatccttcaa  14760
ctgattgcgg aaaactacgt tttgtcagcg tcgttaatct ctcacacact cttactctca  14820
tacgccacag tgcttaggca cttgcgtatc cttaacgatg agggctatat cgaattgtat  14880
aagcaaggta ggacgctata cgcaaaaatc cgcgataatg cgaaacaaat tcagattctg  14940
aattcagaac tggagggggtt taaaaacgta agcgggaagc cgatattgac caaggatgag  15000
```

```
actcctaagg agtttggcaa gaaagatagc ctcactcaaa gaggctaagg ttgcactaaa    15060
agtagcaagc gaccccagaa agtacttcaa cgaagaacag atgactgagg cttacaggat    15120
attctggcag acatgggacg gggacataat tagaagtgct agaaggttcg tggaagtagc    15180
aaaggcaaac cccaagctca caaaaggtga agcaaccaac ataggcgtat tgttgggctt    15240
attcatcttc atactaatag gtatagtact attgcccgta atcgttagcc aagtcaacaa    15300
cctcacaagc ggtacttcac cccaagtaac cggtactaac gccacactcc tgaacttagt    15360
gccgttattc tatatcctag tcctcataat agtccccgca gtcgtggcgt ataagatata    15420
caaagactga ggtgtgaggg atggaaatca gtttaaagcc aatcattttt ttggtcgttt    15480
ttatcatcgt agggatagca ctattcggcc ctataaacag tgttgtaaat aacgttacca    15540
catcgggaac ctacactact atagtttccg gtactgttac tacgtcttca tttgtgtcaa    15600
atccgcaata cgtaggtagc aataacgcta ctatcgtagc cttagtgccg ttattctata    15660
tcctagtcct cataatagtc cccgcagtcg tggcgtataa gttgtataag gaggagtgat    15720
atgaagtggg tgcaaaaggc gataaagaga cccgggaggg tacatcgcta ccttatgagg    15780
ctctacggca aacgggcgtt tacaaaagac ggtgacataa aggcaagtta tctcgataag    15840
gcgataaagc acgttaaaaa agctaagatc ccgaaagaga agaaacgtag tttactgtca    15900
gccctactgt tagcgaaaag gcttaagcgg atgcaccgca agtaggccct ttataaagtc    15960
atattctttt tctttccctg atgagtgcgt taggggatgt aatctacatc ttgggttttc    16020
tctttccggc tttagggcta atcagccgaa actatcttgt taacttaatg gcattcataa    16080
taggaacagt cgccttttttg gtcttcgtcc aaggctatac cgatatagcg ttcagcagtt    16140
cgacgtttta cttaggagta ctgcctctac tacttggtct cgtcaactta ggctatttct    16200
tcaattggtt gagggaggaa aggatatgag gtggggtaga agagatgata gggataccgg    16260
caaaatactt cgaaatagga gtcgtaatag attcaacatt tatcattatg tctctactgt    16320
taagaaagtc aaagagacag agagagaact ccttcgactt acgcaaacat ggaaggctat    16380
taggcttata tcttataata gcgtcggcat cagcattaat cgtctcacat ctcgccttat    16440
acacaaacta catgaactac ttaacgggct tatctcttaa tgcgtttctg ttttatcttg    16500
ggttgaggtg tttgcatgtc tgatgggaaa ctcctttctg ctttcgagga ggaattaaga    16560
aaagcccaaa gcctagagga attaaagcaa aagtatgagg aagcccaaaa acaaatagct    16620
gacggcaaag tactaaagag gctatacaag gtttatgaga aaaggcaaac agaattaatg    16680
cttcagcaat ataggcagat aaaggctgaa ctggaaaaga ggaaaaaggt aaagaaaaag    16740
gataaagccg acataagggt tagagtagta aagaagtgga taaattcacg cttattcagt    16800
gctgagcatt acgtcgcatt actgcaagaa aatcaagacg gcttatcgat actatttcta    16860
agaagagcaa aacttataga aaatcaaggc tatctaatgc tagaagtgaa gaagttaagg    16920
aaggcatggg ttttaacggc tgaacctata ctccttgaaa ggttaaaatt cccattcggc    16980
aaaaagtttg tagccgtgca tttcgttttta cccaattatc cttacacact tcagcttaaa    17040
ccggatgaaa aactgaaaga gttagcagtt aaggcgataa acgggcctca aataatgagc    17100
gcaatgatac gtacaaagtt cttcgaagcg ttagctaggg taggaagcgg gcctgatctg    17160
atgatgctca taatcggcgt tgtcatgggg attggcatag gcgtagcgat aggtttcggt    17220
atagctaacg caaacttaac gcatttgcta tctcaacacg ttacgaacac tacagtgaca    17280
catactacga ccacaacgac ttcaccctca ttcacgattc cctcaaactc ctcaaagggg    17340
```

```
gtgagctaaa atggtctcag taacagaaat aataacatat ggacgagaag caatagaaag   17400
aataatatgc aaatatttta aagattcgaa aatagaaaag atattattct tgccgagtga   17460
ggaagacgta aaggcaaaat atatcattgg acgggtaggg tttataagga ttagtaatac   17520
gtggtctgga attgtcgtag ttgacggggt acaaatacct ttcgttgctg aagtccacct   17580
taatggcaag attgatattt acctttatcc tcaaaaggac ttctacttag cacatttggt   17640
gggtgagctg aatggctaaa aagaacggct taacagaact agagcaatta agaaaagaga   17700
acgaagagtt gagaaagaag ttagaagagt tagaggcgtt gatcaataac gatagcgatg   17760
acgacgaaga gttgcaggaa atcgaaaacc cgtacaccgt tacaaaccgt gcaatagatg   17820
aattagtaag cccaaaggac acaatgttct atttgtcggg aaaccagata tcgttaatct   17880
taagtgcttt tgaattcgcc cgcttaccga cgtacttcgg tgaggaaccg gtaacggagt   17940
tagcggaata cgcccataag ttgaaacatt atctcgtttc gaaaggagga agaggaagga   18000
gggatatact gagagtccta cgcgttagtt caggtcagac aagagagaac gtaaacaaat   18060
caattctgaa acaattattt gaccatggta aggaacatga agatgaagaa gagtaatgaa   18120
tggttatggt tagggactaa aattataaaac gcccataaga ctaacggctt gaaagtgcg    18180 attattttcg ggaacaagg tacgggaaag actacttacg cccttaaggt ggcaaaagaa    18240
gtttaccaga gattaggaca tgaaccggac aaggcatggg aactggccct tgactcttta   18300
ttctttgagc ttaaagatgc attgaggata atgaaaatat tcaggcaaaa tgataggaca   18360
ataccaataa taattttcga cgatgctggg atatggcttc aaaaatattt atggtataag   18420
gaagagatga taaagttta ccgtatatat aacattatta ggaatatagt aagcggggtg    18480
atcttcacta ccccttcccc taacgatata gcgttttatg tgagggaaaa ggggtggaag   18540
ctgataatga taacgagaaa cggaagacaa cctgacggta cgccaaaggc agtagctaaa   18600
atagcggtga ataagataac gattataaaa ggaaaaataa caaataagat gaaatggagg   18660
acagtagacg attatacggt caagcttccg gattgggtat ataaagaata tgtgaaaaga   18720
agaaaggttt atgaggaaaa attgttggag gagttggatg aggttttaga tagtgataac   18780
aaaacggaaa acccgtcaaa cccatcacta ctaacgaaaa ttgacgacgt aacaagatag   18840
tgatacgggt aatgtcagac ccctttagc cattccgcat actttttata ttgctctttc    18900
gctatgccga agagcgatac gtaatgttgc gttaaaacgc gtgtcggttt acgcccttga   18960
ataaaatcga taatatctaa cggtacgctt agctcagcca tcttagacgc tacgaatttg   19020
cggaagtact ttatcgctat agcgtcctta tgacgtcgtt caaagtccgc tattgcccac   19080
ttcgtcacct ctactctctt cagaggcgtt atgtggaata catagaagac gcccttatat   19140
cccctagtcc aactaagcgg ataataacag acgtcgttac cgcaaatgtc cctttcgggt   19200
tccttcagca ctttcagtat ttcgctcagc ctaacgcccg actcgagagc gatacggtag   19260
atgaagtaga cgttttcgct atagtctttt gctaattgta acgtcctttt tatctcttcc   19320
aacgttggaa tgtagatatc agcgttcgcc ttcttcacct ttaccgcttt caatatttta   19380
tccgcaaatt catcatgtat gatattgcgt gacgctaaga aacgtgcaaa gagtcggtaa   19440
gccttctgtg cgtctctcgt ctctttatac ggctttgata tagcattgat gtagtccttt   19500
gcagtttttt cgcttatccc cctttcgttc atgagatagt cgtagaacgc ctttatgttg   19560
ccgtccgtcg cgtattggcg caaattggca accaacgcta ttttacgtcg ttcagttccc   19620
tcttttccgc ctccggagcc ggaggtcccg ggttcaaatc ccggcgggtc cgcttgtagg   19680
ggagtatccc ctacgacccc taatttcatt tttagatatg attcaacgac gtcagctaaa   19740
```

```
ggacccacgt aacgctcttt tacctcaccg ttttcatact ctagcttgta aacataatac  19800
cgcccttccc tctcgcgtaa aatataatcc ccgtatttat aacgcgtctt atctttcgtc  19860
atttcgcctc acagtattat ggttgccaaa acgggcttat aagcattggc aacccgttaa  19920
tttttgccgt taaaacacgt tgaattgaaa gaagacggca aagaatccac acaggtaata  19980
ctaaaaaagt agtattactt acattagaag gactcatttg tccaccttgt attctagcca  20040
tgctatctct gccttcagct catctagctt cccctttatg tctgtcaggt caagggaac   20100 tcctctcatt aacctgagtt cgttttcgat tttttcaagc tccttttcca actcctctag  20160
tttctctaat tcctttagtc gttcttccaa tttcttttcc aatttcccct ttgcgtcatt  20220
tataattatg cttactaccc aaacaattcc taaatcagaa ataattatta actcctctga  20280
gttgaatatc attttccgcc cctcgctaaa tactccttaa agctctgata gaaccccttc  20340
agactaaccc gtaagtctgt taggttcttc cagtattgta atgggattaa gtaatagtag  20400
cttactgcat ctctctcaaa tttgtccttc ttaatctttc cttgcttttc taagttgagt  20460
atttgcagtg ctgagataca ttttaacttg tcctcagcat ctgaatagtg tataaaccaa  20520
accctcccca taacctcatt ctgctttgca acttctactt tagtgcttaa tattgcgtaa  20580
acgctttcgc cgtatctttc tttgctctgt tcttcagtcc atgaacttcc cgtaatatct  20640
atccaaatta aaggataata ttctgtctta gccttaacgt ataaagtcaa atcgtattta  20700
tcttgcagac cgctatagta ttgctcattt attacattag ttaaagtccc cacgccagtt  20760
gggcggatat aaacatcaaa gtctaacaaa cccttagccc gccactttga taaagagatt  20820
aagagctttc caaaaactag gtattctcgc cctaaataag ttgaagggag gatataatcc  20880
tcagcttgat taccccaata ctttagctta aaattagttt cagccatctc actcaccata  20940
ttgaaacgtg ggctagtatg tgaatcagta ctgatgctat tgcaaataac acacttgcag  21000
tagcaattcc tattacaatc catttaccat aatccaccct agtttgttgg tcaatatact  21060
cgttgatgat ctttagtatt tctggcttta gttctgataa tgaaaggaag acagaggcat  21120
aaagtactaa ggaggatgtg aacagattat ccgccttttc tgaaagttta taaagctcat  21180
atcttgctct ctcataatct tcataattaa taatttcatc aaacttttct acttgctctt  21240
catattcttt cttcagagag taaggagttg tcttttcaat tactcctaat tttattaact  21300
tcttaacagc ttccttaaat ccttgtttat tgctagcata cgctaaaggg tcttttcctt  21360
cttgagaagc tctatagata actatagcac cataaacaat atttacaata tcgtatggta  21420
aggaatacga accgatttgg gcaatatctt caactcttct ttgatccatc tagttcacct  21480 cttttgatt tgtttgtagg tttctatcgc agttttcagc gatatcgcaa atagcttccc   21540
cttttccgtt aggtatagcc tcttttcgcc tctttcttga cgctctttca cgaagccctc  21600
ttgtattagg aactttttg catcataaaa ggtggcagtg gacatgggaa attctgcgtt   21660
tactttcttg tataggtcat atgttgctat tccttcatta tcatatagat aagccaaatac 21720 tatggcttcg gggtagaaga atggtgtact tttcatatcc tcctcactcc tcagcctcta  21780
atagcttaac tgcctcctct atcaactgtc ccattgtctt tccagtcttt gccttaagcc  21840
tctgcagtaa atggtaaaaa gatttttactt attccgttct cttctgagaa ccgcttgctt 21900
tttacgatta aattccacat atcatctaag atagagtgtt gtggttctag cttcctcgtg  21960
tagattttcc cctattaatg ttagtttata aagaccggct attttttcac taatt         22015
```

<210> SEQ ID NO 13

```
<211> LENGTH: 61
<212> TYPE: DNA
<213> ORGANISM: Artificial Sequence
<220> FEATURE:
<223> OTHER INFORMATION: synthetic Mini Promoter nucleotide sequence

<400> SEQUENCE: 13
atgttaaaca agttaggtat actatttata aaatagttag gtcataaaag tacccgagaa      60
t                                                                     61

<210> SEQ ID NO 14
<211> LENGTH: 61
<212> TYPE: DNA
<213> ORGANISM: Artificial Sequence
<220> FEATURE:
<223> OTHER INFORMATION: synthetic Mini Promoter nucleotide sequence

<400> SEQUENCE: 14
gctgagagaa aaatttttat ataagcgata ctaatgttct cacggaacgg tgttgtgagg      60
t                                                                     61

<210> SEQ ID NO 15
<211> LENGTH: 119
<212> TYPE: DNA
<213> ORGANISM: Artificial Sequence
<220> FEATURE:
<223> OTHER INFORMATION: synthetic nucleotide sequence

<400> SEQUENCE: 15
atgactctcc aaattcagtt taaaaagtac gagctacctc cattaccta caagatagat       60 gcattagaac cgtatataag taaagatata attgatgtac attataacgg acatcataa     119

<210> SEQ ID NO 16
<211> LENGTH: 75
<212> TYPE: DNA
<213> ORGANISM: Artificial Sequence
<220> FEATURE:
<223> OTHER INFORMATION: synthetic nucleotide sequence

<400> SEQUENCE: 16
atgaataagc tgattcctat atttgtcgtg gtaataattg tactaggcat aattgtgtct      60
atagaatttg gaaag                                                      75

<210> SEQ ID NO 17
<211> LENGTH: 93
<212> TYPE: DNA
<213> ORGANISM: Artificial Sequence
<220> FEATURE:
<223> OTHER INFORMATION: synthetic nucleotide sequence

<400> SEQUENCE: 17
atgaataaat tatatattgt gcttccggta attgtgataa tagccattgg cgttatgggg      60
ggaatcattt acttgcatca acagtctctc agc                                  93

<210> SEQ ID NO 18
<211> LENGTH: 90
<212> TYPE: DNA
<213> ORGANISM: Artificial Sequence
<220> FEATURE:
<223> OTHER INFORMATION: synthetic nucleotide sequence

<400> SEQUENCE: 18
atgaataaaa ccctcggtct aatcctaacc tctgtattcc tactatccac tttaggcata      60
```
ataactggat tgtaataacc aacacaagct                                     90

<210> SEQ ID NO 19
<211> LENGTH: 87
<212> TYPE: DNA
<213> ORGANISM: Artificial Sequence
<220> FEATURE:
<223> OTHER INFORMATION: synthetic nucleotide sequence

<400> SEQUENCE: 19
ttggttgtga aaaaaacatt cgttttatct accttgatat taatttcagt tgtagcgtta    60
gtgagtacag cagtttatac atctggt                                       87

<210> SEQ ID NO 20
<211> LENGTH: 90
<212> TYPE: DNA
<213> ORGANISM: Artificial Sequence
<220> FEATURE:
<223> OTHER INFORMATION: synthetic nucleotide sequence

<400> SEQUENCE: 20
atgaagctaa ttgaaatgct aaaggagata acccaagtcc cagggatttc agggtatgag    60
gaaagagtta gagagaaaat tattgaatgg                                    90

<210> SEQ ID NO 21
<211> LENGTH: 90
<212> TYPE: DNA
<213> ORGANISM: Artificial Sequence
<220> FEATURE:
<223> OTHER INFORMATION: synthetic nucleotide sequence

<400> SEQUENCE: 21
atggtagatt gggaactaat gaaaaaaata atagaatctc caggagtttc tgggtatgaa    60
cacctgggaa ttagagacct tgtggtagat                                    90

<210> SEQ ID NO 22
<211> LENGTH: 30
<212> TYPE: PRT
<213> ORGANISM: Artificial Sequence
<220> FEATURE:
<223> OTHER INFORMATION: synthetic amino acid sequence

<400> SEQUENCE: 22

Met Lys Leu Ile Glu Met Leu Lys Glu Ile Thr Gln Val Pro Gly Ile
1               5                   10                  15

Ser Gly Tyr Glu Glu Arg Val Arg Glu Lys Ile Ile Glu Trp
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: synthetic amino acid sequence

<400> SEQUENCE: 23

Met Val Asp Trp Glu Leu Met Lys Lys Ile Ile Glu Ser Pro Gly Val
1               5                   10                  15

Ser Gly Tyr Glu His Leu Gly Ile Arg Asp Leu Val Val Asp
            20                  25                  30

<210> SEQ ID NO 24

```
<211> LENGTH: 13
<212> TYPE: DNA
<213> ORGANISM: Artificial Sequence
<220> FEATURE:
<223> OTHER INFORMATION: synthetic nucleotide sequence for ribosomal
      binding site

<400> SEQUENCE: 24
gaggtgagtc gga                                                       13

<210> SEQ ID NO 25
<211> LENGTH: 1308
<212> TYPE: PRT
<213> ORGANISM: Sulfolobus solfataricus

<400> SEQUENCE: 25
```

| Met | Glu | Ser | Arg | Ile | Ile | Gln | Val | Val | Ile | Ser | Thr | Phe | Leu | Val |
|---|---|---|---|---|---|---|---|---|---|---|---|---|---|---|
| 1 | | | | 5 | | | | | 10 | | | | | 15 |

Leu Ser Val Leu Phe Pro Leu Leu Ser Leu Ala Tyr Ser Thr Thr Ser
                20                  25                  30

Ile Asn Pro Ser Tyr Pro Gln Ser Asn Val Ile Ser Ala Leu Pro Ser
            35                  40                  45

Asn Thr Asn Ile Ile Leu Tyr Phe Phe Ile Pro Pro Lys Asn Leu Asn
 50                  55                  60

Glu Leu Tyr Leu Ile Ala Gln Glu Val Ala Asn His Gln Ile Lys Pro
 65                  70                  75                  80

Leu Ser Asn Ala Gln Leu Val Ser Met Phe Ser Asn Gln Asp Lys Val
                85                  90                  95

Asn Glu Ser Ile Lys Tyr Leu Glu Ser Lys Gly Phe Thr Ile Ile Tyr
            100                 105                 110

Arg Ser Pro Phe Glu Ile Met Ala Glu Ala Pro Val Ser Leu Val Ser
        115                 120                 125

Ser Val Phe Glu Thr Ser Phe Val Leu Ala Lys Ser Thr Asn Gly Glu
    130                 135                 140

Ile Tyr Tyr Lys Pro Ala Gly Asn Val Lys Ile Pro Ser Thr Leu Asn
145                 150                 155                 160

Asn Leu Leu Ile Gly Gly Leu Thr Asn Phe Thr Asn Val Ser Leu Pro
                165                 170                 175

Leu Ile Gln Leu Gly Lys Leu Glu Asn Gly Asn Leu Ile Pro Asn Lys
            180                 185                 190

Gln Ala Tyr Ser Ser Phe Val Tyr Thr Phe Gln Phe Ser Ala Thr Trp
        195                 200                 205

Tyr Thr Pro Lys Val Ile Glu Gly Ala Tyr Asn Ile Thr Pro Leu Leu
    210                 215                 220

Asn Ser Thr Ala Asp Lys Lys Val Thr Ile Ala Ile Asp Ala Tyr
225                 230                 235                 240

Gly Asp Pro Glu Ile Tyr Gln Asp Val Asn Leu Phe Asp Ala Arg Phe
                245                 250                 255

Gly Leu Pro Pro Ile Asn Leu Thr Val Leu Pro Val Gly Pro Tyr His
            260                 265                 270

Pro Glu Asn Gly Leu Phe Thr Gly Trp Phe Glu Glu Val Ala Leu Asp
        275                 280                 285

Val Glu Ala Ala His Ala Ala Ala Pro Tyr Ser Asn Ile Leu Leu Val
    290                 295                 300

Val Ala Pro Ser Ala Thr Leu Glu Gly Leu Phe Ser Ala Ile Asp Val
305                 310                 315                 320

Val Val Ser Glu Asp Leu Ala Gln Val Val Ser Met Ser Trp Gly Leu
            325                 330                 335

Pro Gly Ile Leu Phe Gly Ala Ser Gly Phe Tyr Ala Val Phe Asn Gly
            340                 345                 350

Ile Ile Phe Pro Asn Tyr Pro Tyr Tyr Asp Tyr Tyr Phe Glu Leu Gly
            355                 360                 365

Ser Ala Glu Gly Ile Thr Phe Leu Ala Ser Ser Gly Asp Leu Gly Ala
            370                 375                 380

Tyr Asn Asp Leu Pro Thr Val Tyr Gly Ser Ala Asn Tyr Pro Ala Ser
385                 390                 395                 400

Ser Pro Phe Val Thr Ala Val Gly Gly Thr Ser Leu Phe Ala Asn Ile
            405                 410                 415

Thr Ser Gly Tyr Ile Ser Thr Tyr Asn Ser Thr Gly Asn Phe Gly Ala
            420                 425                 430

Glu Ile Ala Trp Ser Val Asn Pro Leu Tyr Phe Gly Val Ile Gln Gly
            435                 440                 445

Gly Val Ser Ser Gly Gly Tyr Ser Gln Leu Phe Pro Ala Pro Trp
            450                 455                 460

Tyr Gln Arg Tyr Val Thr His Ser Asn Tyr Arg Ala Ile Pro Asp Val
465                 470                 475                 480

Ala Ala Asp Ala Asn Pro Tyr Thr Gly Phe Thr Ile Tyr Ala Leu Gly
            485                 490                 495

Gln Glu Val Val Ile Gly Gly Thr Ser Leu Ser Ala Pro Leu Trp Ala
            500                 505                 510

Gly Ile Ile Ala Asp Ile Asp Gly Ile Ile Gly His Pro Leu Gly Leu
            515                 520                 525

Val Asn Pro Ile Leu Tyr Glu Ile Tyr Gln Asn Thr Thr Leu Tyr His
            530                 535                 540

Gln Ala Phe His Gln Ile Ser Leu Gly Tyr Asn Gly Tyr Tyr Tyr Ala
545                 550                 555                 560

Asn Ser Ser Tyr Asn Leu Val Thr Gly Leu Gly Ser Pro Asn Ala Gly
            565                 570                 575

Met Leu Gly Val Ile Ile Lys His Ser Leu Ser Lys Ser Leu Ala Ile
            580                 585                 590

Ser Val Ser Thr Phe Glu Thr Gly Val Phe Gln Pro Trp Tyr Phe Tyr
            595                 600                 605

Gly Ser Thr Phe Thr Ile Ala Ala Tyr Ile Thr Tyr Pro Asn Asn Thr
            610                 615                 620

Ile Val Ser Gln Gly Ser Phe Asn Ala Tyr Ile Tyr Thr Ser Glu Gly
625                 630                 635                 640

Tyr Leu Ala Thr Val Pro Leu Ser Phe Asn Gly Ser Tyr Trp Val Gly
            645                 650                 655

Asn Tyr Thr Ile Thr Pro Asn Asn Pro Pro Asn Leu Trp Glu Ile Val
            660                 665                 670

Val Asn Gly Ser Ser Asp Gln Phe Thr Gly Val Gly Thr Val Glu Val
            675                 680                 685

Asp Val Gly Glu Ser Ile Asn Ile Val Ser Pro Ile Pro Tyr Pro Tyr
            690                 695                 700

Ser Phe Pro Ile Pro Tyr Asn Ser Pro Phe Gly Ile Glu Ala Trp Ile
705                 710                 715                 720

Tyr Tyr Pro Asn Gly Thr Pro Val Val Asn Gln Ser Val Thr Ala Tyr
            725                 730                 735

Leu Val Ser Asn Asp Gly Lys Leu Leu Ala Ser Ile Pro Leu Thr Met

```
                    740                745                750
Met Ala Pro Gly Leu Tyr Glu Gly Ser Tyr Ala Leu Leu Pro Pro Leu
            755                760                765

Pro Gln Gly Thr Tyr Leu Leu Ile Val Asn Asp Ser Tyr Gly Ser Ala
            770                775                780

Phe Ser Tyr Val Tyr Phe Gly Glu Tyr Asn Phe Gly Ala Ile Leu Thr
785                790                795                800

Pro Ile Asn Asp Gly Phe Pro Ala Ala Ser Pro Gly Gln Asn Ile Thr
            805                810                815

Ile Ile Asp Glu Val Leu Thr Pro Glu Leu Thr Gly Leu Phe Thr Ser
            820                825                830

Asn Val Thr Ala Tyr Ile Tyr Asn Gln His Gly Asn Leu Ile Asp Gln
            835                840                845

Val Lys Leu Thr Pro Ala Pro Asp Glu Ile Gln Phe Gly Val Tyr Leu
            850                855                860

Leu Phe Phe Leu Tyr Tyr Ala Asn Phe Thr Ile Pro Phe Asp Ala Ser
865                870                875                880

Pro Gly Phe Tyr Asn Val Val Ile Gln Ser Ile Ser Asn Thr Ser Thr
            885                890                895

Gly Leu Val Lys Ala Asp Phe Ile Thr Ser Phe Tyr Val Ser Pro Ala
            900                905                910

Asn Leu Thr Leu Asn Val Lys Val Asn Val Val Tyr Glu Gly Glu
            915                920                925

Leu Leu Lys Ile Phe Ala Asn Ile Thr Tyr Pro Asn Gly Thr Pro Val
            930                935                940

Lys Tyr Gly Met Phe Thr Ala Thr Ile Leu Pro Thr Ser Leu Asn Tyr
945                950                955                960

Glu Gln Leu Ile Ile Gly Phe Glu Ala Gly Ile Pro Leu Gln Tyr Asn
            965                970                975

Ser Thr Leu Gly Glu Trp Val Gly Ile Tyr Ser Ile Pro Ser Ile Phe
            980                985                990

Tyr Gly Ser Ile Phe Gln Gly Ser  Ser Val Tyr Ser Leu Ala Gly Pro
            995                1000                1005

Trp Asn Val Ile Val Ser Gly Val Ser Trp Asn Gly Tyr Asn Leu
            1010                1015                1020

Tyr Ser Thr Pro Ser Ser Phe Asn Phe Val Asn Val Met Pro Tyr
            1025                1030                1035

Thr Phe Ile Asn Asn Ile Val Val Ser Ser Lys Ser Leu Asp Ser
            1040                1045                1050

Pro Leu Leu Ser Lys Ile Asn Ser Thr Thr Tyr Met Leu Ser Asn
            1055                1060                1065

Val Lys Ser Asn Asn Ile Thr Ile Asn Gly Met Asn Val Ile Leu
            1070                1075                1080

Ser Asn Val Ile Ala Asn Thr Val Thr Val Lys Asn Ser Asn Ile
            1085                1090                1095

Met Ile Thr Ser Ser Thr Ile Asn Gln Leu Val Leu Asp Asn Ser
            1100                1105                1110

Ser Val Ser Ile Ile Gly Ser Lys Ile Gly Gly Asp Asn Ile Ala
            1115                1120                1125

Val Val Ala Asn Asp Ser Asn Val Thr Ile Val Ser Ser Val Ile
            1130                1135                1140

Gln Asp Ser Lys Tyr Ala Phe Leu Gln Pro Asn Ser Val Ile Ser
            1145                1150                1155
```

```
Leu Ser Gly Val Asn Met Tyr Asn Val Thr Ser Leu Ser Ser Ile
    1160            1165                1170

Pro Ala Pro Arg Ile Thr Tyr Leu Ser Thr Thr Asn Val Thr Thr
    1175            1180                1185

Ser Lys Glu Ser Ile Ile Val Asn Ile Thr Gly Glu Tyr Leu Arg
    1190            1195                1200

Leu Leu Gly Val Ser Met Asn Asn Lys Pro Val Gly Tyr Ser Val
    1205            1210                1215

Ile Ser Ser Ser Pro Ser Ser Ile Ser Leu Ser Ile Pro Phe Asn
    1220            1225                1230

Ala Ser Gln Leu Ser Asp Gly Gln Tyr Ile Phe Thr Val Ser Ile
    1235            1240                1245

Ser Asp Gly Leu Pro Tyr Asn Leu Thr Phe Asn Leu Leu Asn Asn
    1250            1255                1260

Tyr His Leu Ile Ile Val Gln Asp His Leu Lys Ala Leu Gln Gly
    1265            1270                1275

Ser Val Asn Leu Leu Thr Val Ile Ala Ile Ile Ser Leu Ile Ile
    1280            1285                1290

Ala Ile Ile Ala Val Ala Leu Leu Phe Val Phe Thr Arg Arg Arg
    1295            1300                1305

<210> SEQ ID NO 26
<211> LENGTH: 875
<212> TYPE: PRT
<213> ORGANISM: Sulfolobus solfataricus

<400> SEQUENCE: 26

Met Arg Leu Leu Lys Ile Leu Leu Ala Met Leu Ile Leu Pro Leu
1               5                   10                  15

Phe Ser Phe Phe Thr Leu Ser Ile Ser Leu Tyr Asp Gln Ile Gln Leu
                20                  25                  30

Pro Pro His Tyr Leu Phe Tyr Ile Ser Glu Asn Ala Thr Gln Gly Ser
                35                  40                  45

Gly Ile Asp Val Ile Phe Tyr Thr Ser Ser Pro Ile Thr Phe Met Ile
50                  55                  60

Met Thr Pro Ser Gln Phe Tyr Gln Phe Asn Gln Thr Gly Ser Ser Gln
65                  70                  75                  80

Ser Ile Tyr Ser Ile Thr Thr Asn Ser Leu Ser Lys Phe Phe Pro Leu
                85                  90                  95

Ser Gly Gln Tyr Tyr Ile Val Phe Tyr Asn Asn Ile Ser Asn Asn Pro
                100                 105                 110

Val Thr Leu Asn Tyr Tyr Ile Leu Thr Arg Pro Leu Pro Thr Gly Ile
                115                 120                 125

Ala Asp Tyr Gly Leu Lys Ile Asn Asn Gly Val Ile Ser Pro Tyr Ile
                130             135                 140

Glu Lys Ile Lys Ser Val Ile Gly Ala Val Glu Ile Asn Lys Leu Leu
145                 150                 155                 160

Ala Tyr Asn Ser Thr Pro Pro Ala Gly Val Ser Gln Tyr Ser Ala Ser
                165                 170                 175

Ile Gln Leu Asn Val Val Leu Gln Val Asn Thr Ile Gly Gly Ser Gln
                180                 185                 190

Gln Leu Trp Leu Gln Asn Val Ile Gln Ile Tyr Thr Asn Asn Asp Ser
                195                 200                 205

Tyr Ile Phe Leu Asp Asn Ile Trp Asn Phe Thr Gly Lys Ile Ser Ile
```

```
            210                 215                 220
Leu Ser Asn Ser Thr Val Lys Gly Asn Gly Ile Val Tyr Val Thr Asn
225                 230                 235                 240

Asn Gly Asn Asp Tyr Tyr Ala Tyr Gly Thr Asn Phe Ser Thr Leu Leu
                245                 250                 255

Ile Pro Ser Leu Lys Tyr Leu Leu Ile Asn Thr Ser Tyr Thr Ser Gln
                260                 265                 270

Gly Pro Met Ile Ser Phe Gly Tyr Met Asn Gln Ser Gly Ser Pro Ile
            275                 280                 285

Trp Tyr Asp Asn Val Thr Ile Leu Ile Pro Asn Thr Leu Ser Ala Tyr
        290                 295                 300

Ile Leu Val Asp Gly Tyr Asn Phe Thr Ala Gly Leu Ala Tyr Asp
305                 310                 315                 320

Ala Glu Leu Ile Leu Gly Gly Gly Asn Gly Glu Phe Thr Phe Phe
                325                 330                 335

Asn Glu Ser Asn Val Glu Leu Ala Met Ile Tyr Gln Tyr Leu Asn Gly
                340                 345                 350

Thr Leu Ala Pro Pro Lys Phe Leu Phe Pro Phe Gly Leu Asp Thr Glu
            355                 360                 365

Glu Ser Ala Asp Asn Leu Tyr Ser Ile Ser Tyr Asn Gly Val Tyr Leu
        370                 375                 380

Val Ser Ser Gly Tyr Gln Val Ile Asn Leu Asn Glu Asn Val Ser
385                 390                 395                 400

Gln Leu Arg Phe Asn Val Val Asn Tyr Thr Lys Ala Thr Asp Gln Asn
                405                 410                 415

Phe Pro Tyr Ile Phe Thr Ile Asn Val Ser Gly Gly Val Leu Pro Tyr
            420                 425                 430

Lys Leu Asn Val Thr Ile Ser Asn Ser Gly Asn Glu Leu Ser Gly
        435                 440                 445

Tyr Thr Tyr Val Leu Phe Pro Ser Val Ser Thr Tyr Tyr Leu Phe Leu
    450                 455                 460

Ser Pro Leu Ser Pro Gly Asn Tyr Thr Val Lys Ile Lys Leu Thr Asp
465                 470                 475                 480

Phe Asn Gly Asn Ser Lys Ser Tyr Glu Phe Ser Leu Thr Ile Asn Pro
                485                 490                 495

Pro Leu Lys Val Gln Ile Leu Asn Val Thr Asn Tyr Ile Asp Leu Ala
            500                 505                 510

Leu Pro Tyr Phe Asn Phe Thr Ser Ile Ile Ser Gly Gly Thr Lys Pro
        515                 520                 525

Tyr Asn Ile Ile Ile Thr Ile Ser Asn Asp Ser Gly Ile Leu Ser Glu
    530                 535                 540

Thr Tyr Lys Ile Ile Asn Tyr Thr Ser Ile Thr Tyr Tyr Ala Val Asn
545                 550                 555                 560

Met Lys Gly Tyr Ser Ile Gly Lys Tyr Thr Ile Gln Ile Glu Val Glu
                565                 570                 575

Asp Tyr Ala Gly Ser Ile Asn Ile Ser Lys Tyr Asn Phe Thr Ile Asn
            580                 585                 590

Pro Asn Pro Tyr Ile Ser Thr Leu Ser Tyr Thr Ser Glu Thr Asp Lys
        595                 600                 605

Gly Leu Arg Glu Val Ile Lys Ala Ile Gly Lys Gly Ser Gly Ser
    610                 615                 620

Leu Ile Tyr Tyr Trp Tyr Val Asn Asn Ser Leu Val Ser Gly Ile
625                 630                 635                 640
```

```
Gly Asp Glu Leu Tyr Asn Phe Thr Pro Ser Asn Ile Gly Glu Tyr Asn
                645                 650                 655

Ile Thr Val Met Val Lys Asp Val Leu Gly Val Ser Ser Ala Lys Ser
            660                 665                 670

Val Ile Ile Lys Val Asn Pro Asp Pro Val Val Glu Leu Ser Val Pro
            675                 680                 685

Lys Thr Thr Ile Asp Ser Gly Ala Glu Phe Pro Val Asn Ala Thr Val
            690                 695                 700

Ser Leu Gly Thr Pro Pro Tyr Tyr Ile Ser Trp Tyr Ile Asn Gly Ser
705                 710                 715                 720

Tyr Val Gly Asn Glu Ser Ile Lys Glu Leu Asn Leu Ser Ile Gly
                725                 730                 735

Val Tyr Ile Ile Thr Val Thr Val Arg Asp Ser Ala Gly Tyr Ile Ile
            740                 745                 750

Asn Met Ser Lys Pro Val Leu Ile Val Pro Pro Ser Leu Ser Val
                755                 760                 765

Lys Glu Gln Thr Gln Gly Asn Phe Ile Gln Tyr Asn Thr Ser Ile Ala
            770                 775                 780

Leu Ser Ala Ser Val Asn Gly Gly Thr Asp Pro Tyr Tyr Leu Ile Phe
785                 790                 795                 800

Leu Asn Gly Lys Leu Val Gly Asn Tyr Ser Ser Thr Thr Gln Leu Gln
                805                 810                 815

Phe Lys Leu Gln Asn Gly Glu Asn Asn Ile Thr Leu Ile Ala Lys Asp
                820                 825                 830

Leu Trp Gly Lys Thr Ala Val Lys Thr Leu Ile Val Asn Ser Gly Tyr
            835                 840                 845

Asn Tyr Val Gly Ile Gly Ile Ile Ala Gly Ile Leu Ile Ile Val
            850                 855                 860

Ile Val Val Ile Leu Val Ile Ser Lys Arg Lys
865                 870                 875

<210> SEQ ID NO 27
<211> LENGTH: 606
<212> TYPE: PRT
<213> ORGANISM: Sulfolobus solfataricus

<400> SEQUENCE: 27

Met Glu Ser Lys Asn Val Ile Leu Lys Arg Val Met Leu Leu Leu Val
1               5                   10                  15

Leu Ile Leu Ser Thr Thr Thr Phe Leu Thr Ile Ala Gln Ser Gln
            20                  25                  30

Ala Gln Tyr Tyr Tyr Ile Gln Thr Ser Ser Pro Gln Tyr Thr Ile Ile
            35                  40                  45

Pro Gly Ser Val Phe Val Glu Pro Leu Asn Ser Ser Gln Thr Leu Tyr
50                  55                  60

Ile Ala Val Leu Leu Asn Phe Thr Asn Leu Ala Ser Leu Gln Ser Tyr
65                  70                  75                  80

Leu Asn Glu Ile Tyr Leu Ser Ala Pro Gln Phe His His Trp Leu Thr
                85                  90                  95

Pro Ser Gln Phe Arg Glu Tyr Tyr Pro Ser Arg Ser Tyr Val Asn
            100                 105                 110

Ser Leu Ile Lys Tyr Leu Glu Ser Tyr Asn Leu Gln Phe Leu Gly Asn
            115                 120                 125

Tyr Gly Leu Ile Leu Val Phe Ser Gly Thr Val Gly Asn Ile Glu Lys
```

```
            130                 135                 140
Ala Phe Asn Thr Tyr Ile Asn Val Tyr Tyr Pro Phe Lys Asn Leu
145                 150                 155                 160

Tyr Trp Phe Gly Leu Leu Gly Ile Lys Asn Ile Gly Pro Phe Tyr Tyr
                165                 170                 175

Tyr Ser Asn Asn Val Thr Pro Ser Leu Pro Phe Asn Ile Gly Lys Tyr
            180                 185                 190

Val Leu Gly Val Val Gly Ile Asp Ser Leu Asp Pro Lys Val Val Asn
                195                 200                 205

Val Val Thr Gln Thr Trp His Leu Pro Met Val Lys Ala Gln Ser Gly
            210                 215                 220

Leu Val Ser Lys Ala Ile Ile Ser Pro Ile Thr Ile Glu Gln Tyr Phe
225                 230                 235                 240

Asn Phe Thr Leu Ala Tyr Glu Arg Gly Tyr Thr Gly Gly Gly Ser Asn
                245                 250                 255

Ile Ala Ile Glu Gly Val Pro Glu Ser Phe Val Asn Val Ser Asp Ile
            260                 265                 270

Tyr Ser Phe Trp Gln Leu Tyr Gly Ile Pro Arg Thr Gly His Leu Asn
                275                 280                 285

Val Ile Tyr Phe Gly Asn Val Thr Thr Gly Gly Gln Ser Gly Glu Asn
            290                 295                 300

Glu Leu Asp Ala Glu Trp Ser Gly Ala Phe Ala Pro Ala Ala Asn Val
305                 310                 315                 320

Thr Ile Val Phe Ser Asn Gly Tyr Val Gly Gly Pro Gln Leu Val Gly
                325                 330                 335

Asn Leu Leu Asn Tyr Tyr Glu Tyr Tyr Met Val Asn Tyr Leu
            340                 345                 350

Asn Pro Asn Val Ile Ser Ile Ser Val Thr Val Pro Glu Ser Phe Leu
            355                 360                 365

Ala Ala Tyr Tyr Pro Ala Met Leu Asp Met Ile His Asn Ile Met Leu
            370                 375                 380

Gln Ala Ala Ala Gln Gly Ile Ser Val Leu Ala Ala Ser Gly Asp Trp
385                 390                 395                 400

Gly Tyr Glu Ser Asp His Pro Pro Asn Phe His Ile Gly Thr Tyr
                405                 410                 415

Asn Thr Ile Trp Tyr Pro Glu Ser Asp Pro Tyr Val Thr Ser Val Gly
                420                 425                 430

Gly Ile Phe Leu Asn Ala Ser Ser Asn Gly Ser Ile Val Glu Ile Ser
                435                 440                 445

Gly Trp Asp Tyr Ser Thr Gly Gly Asn Ser Val Val Tyr Pro Ala Gln
            450                 455                 460

Ile Tyr Glu Ile Thr Ser Leu Ile Pro Phe Thr Pro Val Ile Val Arg
465                 470                 475                 480

Thr Tyr Pro Asp Ile Ala Phe Val Ser Ala Gly Gly Tyr Asn Ile Pro
                485                 490                 495

Glu Phe Gly Phe Gly Leu Pro Leu Val Phe Gln Gly Gln Leu Phe Val
                500                 505                 510

Trp Tyr Gly Thr Ser Gly Ala Ala Pro Met Thr Ala Ala Met Val Ala
                515                 520                 525

Leu Ala Gly Thr Arg Leu Gly Ala Leu Asn Phe Ala Leu Tyr His Ile
            530                 535                 540

Ser Tyr Gln Gly Ile Ile Glu Ser Pro Leu Gly Asn Phe Val Gly Lys
545                 550                 555                 560
```

```
Val Ala Trp Ile Pro Ile Thr Ser Gly Asn Asn Pro Leu Pro Ala His
                565                 570                 575

Tyr Gly Trp Asn Tyr Val Thr Gly Pro Gly Thr Tyr Asn Ala Tyr Ala
                580                 585                 590

Met Val Tyr Asp Leu Leu Leu Tyr Ser Gly Leu Ile Glu Ser
            595                 600                 605

<210> SEQ ID NO 28
<211> LENGTH: 570
<212> TYPE: PRT
<213> ORGANISM: Sulfolobus solfataricus

<400> SEQUENCE: 28

Met Gln Phe Arg Lys Thr Phe Leu Phe Leu Asn Ile His Phe Pro Tyr
1               5                   10                  15

Val Leu Arg Asn Thr Leu Leu Ile Leu Leu Leu Leu Pro Thr Pro
            20                  25                  30

Leu Leu Ala Ile Ser Leu Pro Thr Gly Val Val Ala Tyr Asp Gly Pro
        35                  40                  45

Ile Phe Thr Asn Gln Val Leu Gly Tyr Val Asn Ile Thr Ser Leu Gln
50                  55                  60

Ala Tyr Asn Ala Ser Gly Ser Lys Phe Gly Val Pro Pro Tyr Gly Ala
65                  70                  75                  80

Ser Leu Gln Leu Asn Val Met Leu Gln Val Asn Thr Ser Asn Glu Glu
                85                  90                  95

Tyr Tyr Phe Trp Leu Gln Asn Val Ala Asp Phe Ile Thr Asn Glu Ser
            100                 105                 110

Lys Met Phe Phe Ser Glu Asn Ile Trp Asn Ser Thr Thr Pro Leu Ala
        115                 120                 125

Gly Ile Asn Asn Val Ile Gly Lys Gly Glu Ile Tyr Ser Thr Ser Asp
130                 135                 140

Leu Phe Ser His Ser Ser Tyr Tyr Ala Tyr Gly Thr Tyr Tyr Ile Lys
145                 150                 155                 160

Tyr Asp Phe Pro Phe Ser Phe Tyr Leu Ile Val Asn Glu Ser His Asn
                165                 170                 175

Asn Gln Gly Val Tyr Val Ser Phe Gly Tyr Val Ile Leu Gln Asn Gly
            180                 185                 190

Asn Ile Thr Pro Pro Asn Pro Thr Phe Tyr Asp Thr Val Phe Ile Pro
        195                 200                 205

Val Asn Asn Leu Thr Ser Ala Ser Ile Ile Ala Asn Gln Thr Thr
210                 215                 220

Pro Asn Leu Asn Leu Gly Ile Ile Thr Tyr Leu Gly Ser Tyr Leu Asp
225                 230                 235                 240

Ala Glu Leu Val Trp Gly Gly Phe Gly Asn Gly Ala Ser Thr Thr Phe
                245                 250                 255

Leu Asn Met Ser Ser Tyr Leu Ala Leu Leu Tyr Met Lys Asn Gly Lys
            260                 265                 270

Trp Val Pro Phe Ser Gln Val Tyr Asn Tyr Gly Ser Asp Thr Ala Glu
        275                 280                 285

Ser Thr Asn Asn Leu Arg Val Thr Ile Ala Lys Asn Gly Asp Ala Tyr
290                 295                 300

Val Thr Ile Gly Lys Gln Asn Pro Gly Leu Leu Thr Thr Asn Phe Asn
305                 310                 315                 320

Pro Ser Ile Pro Gly Phe Leu Tyr Leu Asn Ile Ser Ser Lys Ile Pro
```

-continued

```
                325                 330                 335
Phe Leu Val Asn Asn Ile Ile Ser Arg Thr Phe Ser Gly Tyr Val Ser
            340                 345                 350
Ala Pro Ile Lys Leu Gly Phe Phe Met Asn Tyr Ser Ile Asn Ser Ser
            355                 360                 365
Ser Phe Ala Val Leu Asn Gly Asn Tyr Pro Ser Leu Ile Glu Pro Asn
            370                 375                 380
Val Ser Trp Phe Lys Ile Leu Asn Ile Ile Pro Asn Tyr Thr Tyr Tyr
385                 390                 395                 400
Tyr Leu Val Arg Val Asn Ser Ser Ile Pro Val Ile Gly Thr Ile Asn
            405                 410                 415
Gly Lys Gln Ile Thr Leu Asn Asp Thr Asn Trp Phe Ala Gln Gly Thr
            420                 425                 430
Gln Ile Lys Ile Val Asn Tyr Thr Tyr Tyr Asn Gly Ser Asp Glu Arg
            435                 440                 445
Tyr Val Ile Ser Ser Ile Leu Pro Ser Leu Ser Phe Asn Ile Ser Ser
            450                 455                 460
Pro Leu Asn Val Thr Ile Asn Thr Ile Lys Gln Tyr Arg Val Ile Ile
465                 470                 475                 480
Asn Ser Asp Leu Pro Thr Tyr Leu Asn Asp Lys Arg Val Asn Gly Ser
            485                 490                 495
Ile Trp Ile Asn Thr Gly Thr Ile Val Lys Leu Ser Ala Ser Ile Pro
            500                 505                 510
Phe Tyr Glu Val Gly Arg Phe Ile Gly Thr Tyr Asn Leu Thr Leu Gly
            515                 520                 525
Gly Thr Ile Val Val Asn Lys Pro Ile Val Glu Lys Leu Gln Leu Ser
            530                 535                 540
Ile Asn Asn Leu Leu Leu Glu Ile Thr Ala Ile Ile Val Ile Val
545                 550                 555                 560
Ile Ile Met Leu Ile Leu Arg Lys Arg Arg
            565                 570

<210> SEQ ID NO 29
<211> LENGTH: 556
<212> TYPE: PRT
<213> ORGANISM: Sulfolobus solfataricus

<400> SEQUENCE: 29

Met Leu Lys His Ile Val Leu Val Leu Leu Leu Leu Leu Thr Pro
1               5                   10                  15
Leu Val Ala Ile Ser Phe Pro Thr Gly Val Val Ala Tyr Asn Gly Pro
            20                  25                  30
Ile Cys Thr Asn Glu Val Leu Gly Tyr Ala Asn Ile Ser Ser Leu Leu
            35                  40                  45
Ala Tyr Asn Thr Ser Ala Ser Gln Leu Gly Val Pro Pro Tyr Gly Ala
            50                  55                  60
Ser Leu Gln Leu Asn Val Met Leu Glu Val Asn Thr Ser Gly Gly Glu
65                  70                  75                  80
Tyr Tyr Phe Trp Leu Gln Asn Val Ala Asp Phe Ile Thr Asn Glu Ser
            85                  90                  95
Lys Val Phe Phe Gly Asp Asn Ile Trp Asn Ser Thr Thr Pro Phe Ala
            100                 105                 110
Gly Ile Asn Asn Ile Val Gly Lys Gly Glu Ile Tyr Ser Thr Ser Asp
            115                 120                 125
```

-continued

```
Phe Phe Ser His Ser Ser Tyr Tyr Ala Tyr Gly Thr Tyr Tyr Ile Lys
    130                 135                 140
Tyr Asn Phe Pro Phe Ser Phe Tyr Leu Ile Ile Asn Glu Ser Tyr Asp
145                 150                 155                 160
Thr Gln Gly Val Tyr Val Ser Phe Gly Tyr Val Ile Leu Gln Asn Gly
                165                 170                 175
Asn Ile Ser Pro Pro Asn Pro Ile Phe Tyr Asp Thr Val Phe Ile Pro
            180                 185                 190
Ile Gln Asn Leu Ser Phe Ala Ser Ile Ile Ala Asn Gln Thr Thr
        195                 200                 205
Pro Ser Ala Asn Phe Gly Ile Val Thr Tyr Leu Gly Asn Tyr Leu Asp
210                 215                 220
Ala Glu Leu Val Trp Gly Gly Phe Gly Asn Gly Ser Thr Thr Phe
225                 230                 235                 240
Leu Asn Met Ser Ser Tyr Leu Ala Leu Leu Tyr Met Lys Ser Gly Glu
                245                 250                 255
Trp Val Pro Phe Ser Gln Val Tyr Asn Tyr Gly Ser Asp Thr Ala Glu
            260                 265                 270
Ser Thr Asn Asn Leu Gln Val Leu Ile Gly Lys Asn Gly Asp Ala Tyr
        275                 280                 285
Val Thr Ile Gly Arg Gln Asn Pro Gly Leu Leu Thr Thr Lys Phe Asn
290                 295                 300
Pro Ser Tyr Pro Ser Phe Leu Tyr Leu Asn Ile Ser Ser Lys Ile Pro
305                 310                 315                 320
Phe Leu Leu Asn Lys Ser Leu Ser His Ala Phe Ser Gly Tyr Val Thr
                325                 330                 335
Thr Gln Ile Lys Leu Gly Phe Phe Lys Asn Tyr Ser Ile Asn Ser Ser
            340                 345                 350
Ser Phe Ala Val Leu Asn Gly Asn Tyr Pro Ser Leu Ile Glu Pro Asn
        355                 360                 365
Val Ser Trp Phe Lys Val Leu Asn Ile Ile Pro Asn Tyr Thr Tyr Tyr
370                 375                 380
Tyr Leu Val Lys Val Asn Ser Gln Ile Pro Val Ile Ala Asn Val Asn
385                 390                 395                 400
Gly Lys Gln Ile Thr Leu Asn Ser Thr Asp Trp Phe Ala Gln Gly Thr
                405                 410                 415
Gln Ile Ser Ile Leu Asn Tyr Thr Tyr Tyr Asn Gly Ser Asn Glu Arg
            420                 425                 430
Tyr Ile Ile Ser Ser Ile Leu Pro Ser Ser Phe Asn Val Ser Leu
        435                 440                 445
Pro Leu Asn Ile Thr Leu Ser Thr Ile Lys Gln Tyr Arg Val Leu Val
450                 455                 460
Asp Ser Asn Leu Pro Val Tyr Leu Asn Gly Glu Arg Val Asn Gly Ser
465                 470                 475                 480
Val Trp Ile Asn Ala Gly Ser Ser Ile Gln Leu Ser Ala Asn Val Pro
                485                 490                 495
Phe Tyr Glu Lys Gly Ile Phe Thr Gly Thr Tyr Asn Val Thr Pro Gly
            500                 505                 510
Ser Ile Ile Thr Val Asn Gly Pro Ile Val Glu Thr Leu Ile Leu Ser
        515                 520                 525
Ile Asn Thr Glu Leu Met Gly Ile Val Ala Val Ile Val Ile Ala Val
530                 535                 540
Val Ala Ile Ala Ile Leu Val Leu Arg Arg Arg Arg
```

<210> SEQ ID NO 30
<211> LENGTH: 443
<212> TYPE: PRT
<213> ORGANISM: Sulfolobus solfataricus

<400> SEQUENCE: 30

```
Met Met Tyr Lys Val Leu Leu Ile Ile Ile Leu Leu Leu Pro Leu Ser
1               5                   10                  15

Met Pro Leu Ser Ile Pro Thr Thr Ser Gln Pro Ser Ala Leu Ala Phe
            20                  25                  30

Pro Ser Gly Val Thr Ser Tyr Pro Leu Asn Thr Ile Tyr Thr Asp
        35                  40                  45

Phe Val Met Gly Arg Ile Asn Ile Ser Tyr Leu Asn Ile Gly Ser Ser
    50                  55                  60

Tyr Leu Pro Gly Gly Glu Tyr Phe Thr Thr Gly Asn Ala Ser Leu Gln
65                  70                  75                  80

Leu Asn Ala Met Val Leu Gly Glu Tyr Trp Ala Gln Asn Val Ile Leu
                85                  90                  95

Phe His Gln Ile Ser Asn Asn Thr Phe Tyr Ala Thr Leu Ile Val Asn
                100                 105                 110

Leu Trp Asn Leu Ser Gly Pro Phe Ser Asn Thr Thr Ser Asn Ser Leu
        115                 120                 125

Val Tyr Gln Gly Leu Gly Val Ile Cys Tyr Gln Gly Pro Thr Phe Lys
    130                 135                 140

Val Thr Leu Pro Leu Ser Ile Ser Leu Phe Met Glu Ile Val Asn Ser
145                 150                 155                 160

Thr Leu Asn Phe Gly Tyr Asn Ile Asn Gly Gln Lys Gly Ile Tyr Phe
                165                 170                 175

Arg Tyr Pro Ile Ile Gly Leu Phe Gln Leu Gly Gly Leu Ser Leu Leu
                180                 185                 190

Gly Leu Pro Asn Asp Leu Glu Leu Val Trp Gly Gly Pro Gly Gly Gly
        195                 200                 205

Ser Val Val Phe Met Asn Val Ser Ser Ile Ala Asn Leu Tyr Tyr Phe
    210                 215                 220

Asn Gly Asn Thr Leu Thr Ile Val Pro Asn Ala Tyr Ser Ile Gly Phe
225                 230                 235                 240

Asp Thr Ala Glu Ser Ala Tyr Gly Val Lys Val Tyr Ser Thr Phe Pro
                245                 250                 255

Ser Val Phe Ser Pro Ile Val Ile Glu Thr Ser Gly Val Asn Val Pro
                260                 265                 270

Ser Val Leu Trp Pro Ile Pro Pro His Val Leu Val Asn Gln Thr Ser
        275                 280                 285

Asn Lys Ile Thr Val Lys Leu Ser Ile Ser Asn Lys Ser Leu Ser Gly
    290                 295                 300

Gln Ala Val Tyr Leu Glu Thr Gly Phe Pro Ser Val Ile Ser Ser
305                 310                 315                 320

Ala Val Thr Asn Ser Ser Gly Ile Ala Val Phe Pro Asn Asn Tyr
                325                 330                 335

Ser Phe Tyr Val Val Tyr Phe Pro Gly Asn Phe Thr Leu Ser Ser Thr
                340                 345                 350

Tyr Tyr Phe Ser Ser Pro Ile Leu Asn Ser Leu Ser Ser Lys Phe Arg
        355                 360                 365
```

-continued

```
Ser Tyr Tyr Gln Asp Leu Leu Asn Phe Leu Asn Ser Ala Gln Asn Ser
    370                 375                 380

Phe Lys Lys Gly Ile Lys Ser Val Leu Ser Lys Gln Glu Thr Ser Ile
385                 390                 395                 400

Thr Thr Thr Thr Leu Thr Ser Thr Thr Ser Ser Ser Gln Phe Gly
                    405                 410                 415

Val Asn Leu Tyr Ile Val Leu Tyr Ile Leu Ala Phe Val Ile Gly Met
                420                 425                 430

Val Ile Ser Ala Ile Leu Ile Arg Phe Lys Leu
                435                 440

<210> SEQ ID NO 31
<211> LENGTH: 1077
<212> TYPE: PRT
<213> ORGANISM: Sulfolobus solfataricus

<400> SEQUENCE: 31

Met Thr Trp Ser Ile Phe Leu Leu Ile Leu Ala Leu Ser Asp Ile Val
1               5                   10                  15

Leu Pro Leu Thr Ile Thr Asn Ile Asn Asn Gln Ser Ile Thr Thr Leu
                20                  25                  30

Ser Pro Asn Tyr Tyr Leu Thr Val Ala Ile Val Phe Pro Pro Ser Asn
                35                  40                  45

Leu Thr Leu Leu Gln Gln Tyr Val Gln Glu His Val Ile Leu Asn Gln
    50                  55                  60

Thr Gln Val Glu Lys Leu Phe Ile Pro Thr Glu Ile Ser Lys Thr
65                  70                  75                  80

Leu Ser Gln Leu Arg Gln Ser Asn Ile Ser Ala Thr Ser Tyr Met Asn
                85                  90                  95

Val Ile Leu Ala Ser Gly Thr Val Ser Gln Leu Glu Lys Ala Leu Asn
                100                 105                 110

Gly Lys Phe Tyr Val Tyr Glu Leu Asn Gly Lys Arg Phe Phe Glu Phe
            115                 120                 125

Phe Gly Ser Pro Val Ile Pro Asn Ala Ile Val Ile Gly Thr Asn Ile
    130                 135                 140

Thr Ser Leu Ile Leu Asn Lys Pro Thr Thr Leu Tyr Asn Val Thr Gln
145                 150                 155                 160

Ala Val Ala Tyr Asn Ala Leu Lys Pro Ser Gln Leu Leu Tyr Ala Tyr
                165                 170                 175

Asn Ile Ser Trp Leu His Ala His Asn Ile Thr Gly Lys Gly Thr Ala
                180                 185                 190

Ile Gly Ile Leu Asp Phe Tyr Gly Asn Pro Tyr Ile Gln Gln Gln Leu
            195                 200                 205

Gln Glu Phe Asp Lys Gln Tyr Asn Ile Pro Asn Pro Phe Lys
    210                 215                 220

Ile Val Pro Ile Gly Ala Tyr Asn Pro Asn Asn Gly Ile Ser Thr Gly
225                 230                 235                 240

Trp Ala Met Glu Ile Ser Leu Asp Val Glu Tyr Ala His Val Ile Ala
                245                 250                 255

Pro Asp Ala Gly Ile Val Leu Tyr Val Ala Asn Pro Asn Ile Pro Leu
                260                 265                 270

Pro Ala Ile Ile Ala Tyr Ile Val Gln Gln Asp Glu Val Asn Val Val
            275                 280                 285

Ser Gln Ser Phe Gly Ile Pro Glu Leu Tyr Val Asp Leu Gly Leu Ile
    290                 295                 300
```

-continued

```
Pro Leu Ser Tyr Val Asn Ser Leu Met Tyr Glu Tyr Trp Leu Gly Glu
305                 310                 315                 320

Val Glu Gly Ile Ser Phe Ala Ala Ser Gly Asp Ala Gly Gly Asn
            325                 330                 335

Gly Tyr Asn Tyr Phe Leu Ala Pro Gln Gly Ser Val Ile Phe Pro Ala
        340                 345                 350

Ser Ile Pro Tyr Val Leu Ala Val Gly Gly Ser Ser Val Tyr Ile Gly
            355                 360                 365

Gly Asn Lys Thr Met Glu Thr Ala Trp Ser Gly Glu Ser Val Leu Gly
        370                 375                 380

Ala Ser Thr Gly Gly Tyr Ser Thr Leu Phe Pro Ala Pro Trp Tyr Gln
385                 390                 395                 400

Asp Ser Asn Gly Phe Arg Val Val Pro Asp Val Val Ala Asp Ala Asn
            405                 410                 415

Pro Tyr Thr Gly Ala Phe Ile Leu Tyr Tyr Asn Gln Thr Tyr Leu
        420                 425                 430

Val Gly Gly Thr Ser Leu Ala Thr Pro Ile Val Ser Gly Ile Ile Asp
        435                 440                 445

Leu Met Thr Gln Ser Tyr Gly Lys Leu Gly Phe Val Asn Pro Phe Leu
    450                 455                 460

Tyr Glu Leu Arg Asn Thr Ser Ala Leu Ser Pro Ile Gly Phe Gly Tyr
465                 470                 475                 480

Asn Thr Pro Tyr Tyr Val Asn Ser Ser Glu Leu Asn Pro Val Thr Gly
            485                 490                 495

Leu Gly Ser Ile Asn Ala Gly Tyr Leu Tyr Gln Leu Leu Pro Lys Val
            500                 505                 510

Ile His Ser Ser Ser Ile Ser Val Gly Val Asn Asn Ile Thr Tyr Leu
        515                 520                 525

Asp Gly Gln Val Val Lys Val Val Ala Asn Ile Thr Gly Ile Arg Pro
    530                 535                 540

Ser Ser Val Ile Gly Ile Val Tyr Asn Gly Ser Ser Val Val Gln Gln
545                 550                 555                 560

Phe Ser Leu Ser Phe Asn Gly Thr Tyr Trp Val Gly Glu Phe Val Ala
            565                 570                 575

Glu Gly Ser Gly Ile Glu Glu Val Ile Val Lys Ala Gly Asn Leu Glu
            580                 585                 590

Gly Ser Thr Tyr Val Thr Ile Gly Tyr Gln Ala Gln Phe Ile Phe Pro
        595                 600                 605

Pro Ile Ala Leu Phe Pro Glu Pro Glu Pro Val Pro Ile Val Val Gln
    610                 615                 620

Leu Ile Tyr Pro Asn Gly Ser Leu Val Arg Asn Pro Ser Asn Leu Thr
625                 630                 635                 640

Ala Leu Ile Tyr Lys Tyr Asp Gln Met Asn Asn Lys Met Ser Ile Ile
            645                 650                 655

Ser Ser Val Gln Leu Gln Arg Thr Ser Leu Ile Asn Leu Ser Ile Leu
        660                 665                 670

Gly Ile Gln Ile Glu Ser Ser Tyr Leu Thr Gly Val Tyr Gln Leu Pro
        675                 680                 685

Ser Asn Ile Ile Ser Gly Val Tyr Phe Ile Lys Ile Pro Asn Val Phe
    690                 695                 700

Gly Phe Asp Glu Phe Val Ser Gly Ile Tyr Ile Leu Asp Ala Val Tyr
705                 710                 715                 720
```

```
Pro Pro Val Phe Thr Asn Pro Val Val Leu Ser Gly Gln Asn Val
            725                 730                 735

Thr Ile Leu Ala Glu Ala Leu Ala Ile Gly Ser Pro Asn Val Thr Val
        740                 745                 750

Thr Phe Tyr Asn Ile Ser Gly Asn Lys Val Tyr Ser Ile Pro Val Asn
        755                 760                 765

Ala Ile Thr Tyr Gln Asn Thr Leu Leu Tyr Ile Thr Gln Ile Thr Leu
        770                 775                 780

Pro Lys Leu Lys Pro Gly Tyr Tyr Tyr Val Val Thr Lys Ala Ile Tyr
785                 790                 795                 800

Asn Ala Ser Asn Phe Thr Ala Glu Gly Val Gly Leu Thr Gln Ile Tyr
            805                 810                 815

Val Ser Pro Tyr Ser Leu Asn Val Lys Val Arg Ile Ile Pro Asn Asn
        820                 825                 830

Ser Ile Val Tyr Gln Asn Gln Gln Ile Tyr Val Ile Ala Asn Ile Thr
        835                 840                 845

Tyr Pro Asn Gly Thr Glu Val Lys Tyr Gly Ser Phe Ser Ala Ile Ile
        850                 855                 860

Val Pro Ser Tyr Leu Ser Ser Gln Phe Asp Asn Leu Gln Leu Gln Tyr
865                 870                 875                 880

Ser Val Pro Leu Thr Tyr Ile Asn Gly Ser Trp Ile Gly Gln Leu Glu
            885                 890                 895

Ile Pro Ser Gly Ser Ser Thr Asn Ser Leu Gly Tyr Ser Thr Tyr Gly
            900                 905                 910

Ile Ser Gly Tyr Trp Asp Val Tyr Val Glu Gly Ile Ser Ala Asp Gly
        915                 920                 925

Ile Pro Thr Asn Phe Pro Ala Thr Leu Asp Val Asn Thr Leu Ser Ile
        930                 935                 940

Asn Pro Ile Ser Pro Ser Ser Gln Phe Val Val Leu Pro Tyr Val Tyr
945                 950                 955                 960

Val Ser Val Phe Asn Gly Thr Ile Ala Phe Asn Glu Phe Ile Asp Lys
            965                 970                 975

Ala Ile Val Val Gly His Asn Ala Thr Phe Ile Asn Ser Ile Ile Arg
            980                 985                 990

Asn Leu Ile Val Glu Asn Gly Thr Val Thr Leu Ile Asn Ser Lys Val
        995                 1000                1005

Gln Asn Val Ser Leu Val Asn Ser Glu Ile Ile Lys Ile Asn Ser
    1010                1015                1020

Thr Val Gly Asn Asn Val Asn Tyr Ile Thr Thr Ile Gly Asn Asn
    1025                1030                1035

His Ala Lys Ser Ser Tyr Pro Ser Leu Asp Ser Gly Ser Ile Leu
    1040                1045                1050

Thr Ile Gly Ile Val Leu Asp Ile Ile Thr Ile Ala Leu Ile
    1055                1060                1065

Leu Ile Lys Arg Arg Lys Lys Phe Ile
    1070                1075

<210> SEQ ID NO 32
<211> LENGTH: 141
<212> TYPE: PRT
<213> ORGANISM: Sulfolobus solfataricus

<400> SEQUENCE: 32

Met Lys Met Lys Lys Ser Asp Ile Ile Ile Ile Leu Phe Ile Ala Leu
1               5                   10                  15
```

```
Ile Tyr Ile Leu Met Phe Ser Asn Ile Val Gln Ser Ala Ser Val Glu
            20                  25                  30

Gly Val Ser Met Tyr Pro Ile Phe Gln Asn Gly Ala Leu Thr Phe Tyr
        35                  40                  45

Val Lys Pro Ile Ser Ile Asn Glu Gly Asn Val Ile Ile Tyr Lys Ser
 50                  55                  60

Pro Tyr Phe Asn Asn Tyr Val Ile His Arg Val Ile Ala Thr Asp Asn
 65                  70                  75                  80

Gly Tyr Tyr Ile Thr Gln Gly Val Asp Lys Ile Thr Asn Pro Ile Pro
                85                  90                  95

Asp Asn Arg Ile Gly Leu Glu Pro Ala Ser Gly Ile Pro Lys Asn Leu
            100                 105                 110

Val Val Gly Lys Ile Val Glu Phe Gly Asn Phe Thr Phe Ser Ile Pro
            115                 120                 125

Tyr Leu Gly Tyr Ile Ser Ile Leu Phe Ser Ser Ile Ile
            130                 135                 140

<210> SEQ ID NO 33
<211> LENGTH: 1269
<212> TYPE: PRT
<213> ORGANISM: Sulfolobus solfataricus

<400> SEQUENCE: 33

Met Tyr Arg Tyr Ile Phe Leu Met Ser Met Leu Leu Ile Ser Ile Ile
 1               5                  10                  15

Pro Leu Val Phe Ala Ser Asn Pro Asn Met Tyr Gln Asn Pro Ile Thr
            20                  25                  30

Leu Lys Glu Phe Arg Glu Ile Gly Thr Leu Asn Ala Asn Glu Glu Val
        35                  40                  45

Ile Val Thr Ile Phe Val Pro Leu Lys Asn Leu Asp Leu Leu Tyr Tyr
 50                  55                  60

Tyr Ala Ser Gly Ala Ser Asn Pro Ala Ser Pro Leu Tyr His Lys Phe
 65                  70                  75                  80

Leu Ser Pro His Glu Val Gln Gln Leu Phe Leu Pro Thr Glu Glu Tyr
                85                  90                  95

Asn Gln Ile Leu Asn Tyr Val Lys Ser Gly Phe Gln Val Ile Phe
            100                 105                 110

Thr Ala Ser Asn Ser Val Ile Val Lys Gly Thr Val Gly Gln Val
            115                 120                 125

Glu Lys Tyr Leu Gly Thr Lys Tyr Ala Val Tyr Ser Asn Gly Ser Val
            130                 135                 140

Thr Tyr Tyr Thr Asn Tyr Gly Tyr Pro Lys Ile Asn Ala Tyr Val Tyr
145                 150                 155                 160

Ser Ser Asn Ile Ser Ala Ile Phe Phe Ala His Pro Ser Thr Leu Ile
            165                 170                 175

Thr Glu Ser Thr Ile Lys Ser Phe Gln Gln Ile Asn Gln Thr Phe
            180                 185                 190

Pro Leu Glu Gly Tyr Trp Pro Thr Val Leu Gln Lys Val Tyr Asn Val
            195                 200                 205

Thr Thr Glu Gly Glu Asn Thr Thr Ile Gly Ile Leu Asp Phe Tyr Gly
            210                 215                 220

Asp Pro Tyr Ile Val Gln Gln Leu Ala Tyr Phe Asp Lys Ile Thr Gly
225                 230                 235                 240

Leu Pro Asn Pro Pro Asn Phe Ser Val Val Pro Ile Gly Pro Tyr Asn
```

```
                245                 250                 255
Pro Asn Leu Gly Ile Val Thr Gly Trp Ala Gly Glu Ile Ser Leu Asp
            260                 265                 270
Val Glu Val Ala His Ala Ile Ala Pro Lys Ala Asn Ile Thr Leu Tyr
            275                 280                 285
Ile Ala Asn Pro Asn Ile Pro Leu Pro Ala Ile Ile Ala Tyr Ile Thr
            290                 295                 300
Ser Gln Asn Lys Val Asp Thr Leu Ser Gln Ser Phe Ser Ile Pro Glu
305                 310                 315                 320
Ser Leu Phe Ser Ser Leu Phe Asn Gly Pro Leu Phe Tyr Ser Cys Ile
                325                 330                 335
Ile Leu Ser Asp Glu Tyr Tyr Ala Leu Gly Ser Ala Glu Gly Ile Thr
                340                 345                 350
Phe Leu Ala Ser Ser Gly Asp Ala Gly Gly Ser Gly Tyr Ser Asn Gly
                355                 360                 365
Pro Ile Gly Thr Val Gly Tyr Pro Ser Thr Ser Pro Phe Val Thr Ser
            370                 375                 380
Val Gly Gly Thr Thr Val Tyr Val Gln Phe Pro Asn Gly Ser Tyr Tyr
385                 390                 395                 400
Gln Thr Ala Trp Ser Asn Tyr Gly Phe Val Pro Asn Asn Val Asn Tyr
                405                 410                 415
Gly Gly Ser Thr Gly Gly Val Ser Ile Ile Glu Pro Lys Pro Trp Tyr
                420                 425                 430
Gln Trp Gly Leu Pro Thr Pro Ser Thr Tyr Pro Asn Gly Lys Leu Ile
                435                 440                 445
Pro Glu Ile Ser Ala Asn Ala Asn Val Tyr Pro Gly Ile Tyr Ile Val
            450                 455                 460
Leu Pro Ser Asn Thr Thr Gly Ile Thr Gly Thr Ser Glu Ala Ser
465                 470                 475                 480
Pro Leu Thr Ala Gly Val Leu Ala Thr Ile Glu Ser Tyr Thr His His
                485                 490                 495
Arg Ile Gly Leu Leu Asn Pro Ile Leu Thr Tyr Met Ala Glu Asn Tyr
                500                 505                 510
Tyr Gly Lys Val Ile Glu Pro Ile Thr Phe Gly Tyr Asn Ile Pro Trp
            515                 520                 525
Val Ala Thr Tyr Gly Tyr Asn Leu Val Thr Gly Tyr Gly Thr Ile Asn
            530                 535                 540
Ala Gly Tyr Phe Glu Lys Ile Leu Pro Thr Leu Asn Leu Ser Lys Glu
545                 550                 555                 560
Leu Asn Val Ile Val Ser Val Tyr Asn Thr Ser Ile Pro Thr Val Ser
                565                 570                 575
Pro Gln Gln Phe Tyr Pro Gly Gln Arg Ile Leu Val Thr Ala Asn Ile
            580                 585                 590
Thr Tyr Pro Asn Gly Ser Pro Val Gln Thr Gly Glu Phe Lys Ala Leu
            595                 600                 605
Ile Glu Asn Tyr Leu Gly Asn Leu Thr Thr Phe Asn Leu Thr Tyr Asn
            610                 615                 620
Ser Leu Thr Lys Leu Trp Thr Gly Ser Gly Val Leu Ser Asn Lys Ala
625                 630                 635                 640
Ser Gly Ile Leu Phe Val Tyr Val Tyr Gly Ser Ser Asp Gly Leu Arg
                645                 650                 655
Gly Ile Gly Tyr Tyr Glu Thr Phe Ser Gly Tyr Tyr Ile Thr Phe Asn
                660                 665                 670
```

```
Tyr Thr Thr Thr Phe Thr Pro Val Tyr Val Glu Leu Gly Asn Ala Glu
        675                 680                 685

Leu Gly Ile Thr Leu Ser Asn Ser Tyr Phe Gln Ala Pro Ile Gly Val
        690                 695                 700

Met Asn Ile Thr Leu Asn Ile Tyr Ser Tyr Asn Ile Thr Thr Asn Ala
705                 710                 715                 720

Tyr Thr Phe Val Thr Thr Leu Ser Val Pro Ile Lys Asn Gly Val Gly
                725                 730                 735

Val Ile Asp Leu Pro Pro Asp Leu Ser Ile Gly Asp Leu Leu Ile Ile
            740                 745                 750

Ala Glu Gly Asn Ala Tyr Gly Phe Asp Ala Phe Thr Asn Gly Val Tyr
                755                 760                 765

Met Gln Thr Leu Phe Ile Leu Pro Gln Val Val Glu Pro Gly Ser
        770                 775                 780

Val Ser Pro Gly Gln His Ile Thr Ile Glu Gly Ser Ile Pro Pro
785                 790                 795                 800

Val Asn Leu Pro Ser Thr Thr Phe Gln Asp Ala Leu Gln Gly Thr Asn
                805                 810                 815

Ile Thr Ala Lys Leu Val Ser Ser Asn Gly Val Val Ile Asn Glu Ala
            820                 825                 830

Asn Ile Pro Leu Ser Pro Asn Gly Ile Tyr Phe Gly Tyr Leu Tyr Ile
        835                 840                 845

Pro Lys Asn Thr Pro Ser Gly Leu Tyr Asn Val Leu Leu Phe Ala Thr
    850                 855                 860

Tyr Tyr Ser Tyr Thr Leu Asn Thr Thr Ile Arg Gly Phe Tyr Tyr Gly
865                 870                 875                 880

Gln Ile Tyr Val Ser Asn Gln Ala Thr Ile Ser Val Lys Ser Val Asn
                885                 890                 895

Tyr Ala Phe Glu Gly Gln Thr Val Phe Ile Tyr Ala Asn Ile Thr Asn
            900                 905                 910

Gly Thr Asn Glu Ile Lys Phe Gly Met Phe Ser Ala Thr Val Tyr Pro
        915                 920                 925

Ser Ser Leu Ser Phe Asn Tyr Thr Thr Ile Ser Ile Ile Glu Ile
    930                 935                 940

Pro Leu Trp Tyr Asn Pro Lys Ile Gly Glu Trp Glu Gly Asn Phe Thr
945                 950                 955                 960

Leu Pro Ser Ala Ile Ser Ala Gly Asn Leu Thr Tyr Leu Ala Gly Gln
                965                 970                 975

Gly Tyr Phe Gly Val Pro Phe Lys Val Leu Ile Thr Gly Ile Ser Ala
            980                 985                 990

Leu Gly Asn Pro Thr Thr Thr Asn  Ser Gly Asn Ala Tyr  Thr Ile Asn
        995                 1000                1005

Val Leu  Pro Tyr Thr Leu Phe  Thr Asn Gln Thr Leu  Asp Lys Thr
    1010                1015                 1020

Leu Pro  Ser Tyr Ala Ser Leu  Val Asn Val Lys Ile  Leu Asn Val
    1025                1030                 1035

Ser Gly  Asn Leu Leu Asn Asp  Phe Leu Thr Asn Val  Ile Ile Val
    1040                1045                 1050

Asn Ser  Asn Val Lys Ile Leu  Asn Gly Asn Ile Ser  Asn Ile Val
    1055                1060                 1065

Ile Arg  Asn Ser Thr Val Leu  Ile Met Gln Ser Asn  Ala Asn Asn
    1070                1075                 1080
```

-continued

```
Ile Thr Leu Tyr Asn Ser Thr Leu Tyr Ala Ile Gly Gly Ser Ile
    1085                1090                1095

Asn Gly Leu Asn Val Val Asn Ser Lys Val Val Pro Ile Asn Ile
    1100                1105                1110

His Ile Gln Gly Leu Tyr Pro Glu Leu Pro Ser Ile Ser Ile Asn
    1115                1120                1125

Leu Pro Ser Lys Asn Val Thr Gly Thr Val Asn Val Thr Val Asn
    1130                1135                1140

Val Ile Gly Glu Asp Val Ser Arg Ile Asn Val Tyr Leu Asn Gly
    1145                1150                1155

Asn Leu Ile Asn Ser Phe Thr Thr Asn Gly Thr His Ile Val Thr
    1160                1165                1170

Ile Asn Thr Gln Asn Tyr Pro Asp Gly Gly Tyr Asn Leu Thr Val
    1175                1180                1185

Thr Ala Ile Gln Ser Asp Gly Leu Ser Ser Asn Ser Ser Tyr
    1190                1195                1200

Leu Tyr Phe Glu Asn Gly Leu Thr Asn Leu Asn Thr Lys Val Asn
    1205                1210                1215

Val Ile Ser Asn Gln Leu Thr Asn Val Ser Asn Ser Leu Ser Ser
    1220                1225                1230

Ser Ile Ser Ser Leu Arg Thr Ala Ser Leu Glu Tyr Gln Ser Ile
    1235                1240                1245

Ser Leu Ala Ile Gly Ile Ile Ala Ile Val Leu Ala Ile Leu Ala
    1250                1255                1260

Leu Val Arg Arg Arg Arg
    1265

<210> SEQ ID NO 34
<211> LENGTH: 601
<212> TYPE: PRT
<213> ORGANISM: Sulfolobus solfataricus

<400> SEQUENCE: 34

Met Tyr Met Lys Ala Lys His Leu Ile Ser Leu Ile Val Ile Leu Thr
1               5                   10                  15

Pro Leu Val Thr Leu Leu Thr Ser Ala Val Tyr Thr Ser Gly Gly Ile
                20                  25                  30

Thr Phe Tyr Ser Pro Ala Tyr Asn Gly Glu Ser Tyr Tyr Thr Gly Gln
            35                  40                  45

Ser Ile Thr Ile Asp Ala Leu Leu Pro Gln Gln Phe Ala Thr Asp Ala
    50                  55                  60

Ala Thr Ile Asn Phe Phe Pro Asn Ser Ser Leu Ala Val Thr Ile
65              70                  75                  80

Pro Val Gln Ile Asn Gly Ser Gly Gly Ile Tyr Val Pro Asn Ala Tyr
                85                  90                  95

Ala Phe Pro Asn Val Pro Gly Thr Trp Gln Ile Thr Ile Glu Val Ala
            100                 105                 110

Gly Gly Val Ala Val Gly Thr Ile Asn Val Asn Val Ile Gln Arg Thr
        115                 120                 125

Pro Leu Val Thr Val His Leu Gly Tyr Gly Val Val Gly Gln Ala Leu
    130                 135                 140

Pro Gln Thr Pro Thr Ile Thr Leu Thr Phe Pro Asn Gly Thr Thr Ile
145                 150                 155                 160

Thr Val Pro Leu Gln Gly Thr Val Asn Val Pro Ser Gly Thr Ser Tyr
                165                 170                 175
```

-continued

```
Gln Val Glu Gln Ala Ile Thr Glu Asn Asn Ile Arg Trp Ala Thr Asn
            180                 185                 190
Tyr Thr Ser Gly Thr Ile Thr Pro Ala Thr Thr Ser Ile Thr Pro Thr
            195                 200                 205
Tyr Tyr Gln Gln Tyr Leu Val Thr Phe Asn Tyr Thr Val Gln Gly Gly
            210                 215                 220
Thr Gly Tyr Ser Pro Pro Thr Val Tyr Arg Ser Leu Gly Met Asn
225                 230                 235                 240
Glu Thr Ala Lys Ala Pro Ala Ser Val Trp Val Asp Ala Asn Ser Ala
            245                 250                 255
Tyr Ile Tyr Ser Pro Glu Leu Gln Ser Asn Val Gln Gly Glu Arg Trp
            260                 265                 270
Ile Ala Val Asn Phe Thr Gly Ile Ile Lys Ala Pro Gly Glu Ile Asn
            275                 280                 285
Glu Tyr Tyr Ile Asn Gln Tyr Leu Val Thr Val Gln Ser Gln Ile Pro
            290                 295                 300
Val Tyr Ala Ile Val Asn Gly Ala Asn Glu Thr Leu Asn Ser Thr Asn
305                 310                 315                 320
Trp Phe Thr Gln Gly Thr Thr Ile Lys Leu Glu Asn Ile Thr Lys Tyr
            325                 330                 335
Val Ser Ser Val Glu Arg Tyr Val Ile Ala Asn Phe Ser Pro Ser Glu
            340                 345                 350
Val Ile Thr Val Asn Gln Pro Thr Thr Ile Lys Val Asn Thr Val Thr
            355                 360                 365
Gln Tyr Phe Ile Asn Val Asn Ser Pro Val Gln Leu Lys Ala Leu Ile
            370                 375                 380
Asn Gly Ala Asn Glu Ser Leu Thr Ala Gly Trp Tyr Asn Gln Gly Thr
385                 390                 395                 400
Ser Ile Lys Ile Glu Asn Leu Thr Tyr Tyr Val Gly Asn Gly Glu Arg
            405                 410                 415
Leu Ile Leu Gly Lys Val Leu Pro Ser Leu Glu Ile Ile Val Asn Gly
            420                 425                 430
Ser Tyr Thr Ile Ser Thr Thr Thr Ile Thr Gln Tyr Phe Val Asn Val
            435                 440                 445
Ser Ser Pro Ile Pro Val Gln Val Leu Ile Asn Gly Ser Lys Thr Ile
            450                 455                 460
Leu Asn Ser Ser Trp Ile Asn Ala Gly Thr Ser Ile Leu Val Leu Asn
465                 470                 475                 480
Tyr Thr Tyr Asn Ile Ser Pro Gln Glu Arg Val Ile Val Gly Ile
            485                 490                 495
Ser Pro Ser Gln Ser Phe Thr Val Asn Ser Pro Glu Thr Leu Lys Leu
            500                 505                 510
Leu Thr Val Thr Gln Tyr Leu Val Thr Ile Asn Gly Val Ser Lys Phe
            515                 520                 525
Tyr Asn Ser Gly Ser Lys Ile Val Leu Asn Ala Ser Val Pro Phe Tyr
            530                 535                 540
Glu Thr Ala Thr Phe Lys Gly Thr Tyr Asn Val Ser Pro Gly Ala Thr
545                 550                 555                 560
Ile Thr Val Asn Gln Pro Ile Thr Glu Thr Leu Val Glu Ser Pro Asn
            565                 570                 575
Tyr Leu Ile Leu Gly Ala Ile Ala Ala Val Ile Ile Val Val Ala
            580                 585                 590
```

```
Val Val Val Ile Ile Leu Leu Arg Arg
            595                 600
```

<210> SEQ ID NO 35
<211> LENGTH: 340
<212> TYPE: PRT
<213> ORGANISM: Sulfolobus acidocaldarius

<400> SEQUENCE: 35

```
Met Asn Phe Lys Ser Ile Cys Leu Ile Ile Leu Leu Ser Ala Leu Ile
1               5                   10                  15

Ile Pro Tyr Ile Pro Gln Asn Ile Tyr Phe Pro His Arg Asn Thr
                20                  25                  30

Thr Gly Ala Thr Ile Ser Ser Gly Leu Tyr Val Asn Pro Tyr Leu Tyr
            35                  40                  45

Tyr Thr Ser Pro Pro Ala Pro Ala Gly Ile Ala Ser Phe Gly Leu Tyr
    50                  55                  60

Asn Tyr Ser Gly Asn Val Thr Pro Tyr Val Ile Thr Thr Asn Glu Met
65                  70                  75                  80

Leu Gly Tyr Val Asn Ile Thr Ser Leu Leu Ala Tyr Asn Arg Glu Ala
                85                  90                  95

Leu Arg Tyr Gly Val Asp Pro Tyr Ser Ala Thr Leu Gln Phe Asn Ile
            100                 105                 110

Val Leu Ser Val Asn Thr Ser Asn Gly Val Tyr Ala Tyr Trp Leu Gln
        115                 120                 125

Asp Val Gly Gln Phe Gln Thr Asn Lys Asn Ser Leu Thr Phe Ile Asp
    130                 135                 140

Asn Val Trp Asn Leu Thr Gly Ser Leu Ser Thr Leu Ser Ser Ser Ala
145                 150                 155                 160

Ile Thr Gly Asn Gly Gln Val Ala Ser Ala Gly Gly Gln Thr Phe
                165                 170                 175

Tyr Tyr Asp Val Gly Pro Ser Tyr Thr Tyr Ser Phe Pro Leu Ser Tyr
            180                 185                 190

Ile Tyr Ile Ile Asn Met Ser Tyr Thr Ser Asn Ala Val Tyr Val Trp
        195                 200                 205

Ile Gly Tyr Glu Ile Ile Gln Ile Gly Gln Thr Glu Tyr Gly Thr Val
    210                 215                 220

Asn Tyr Tyr Asp Lys Ile Thr Ile Tyr Gln Pro Asn Ile Ile Ser Ala
225                 230                 235                 240

Ser Leu Met Ile Asn Gly Asn Asn Tyr Thr Pro Asn Gly Leu Tyr Tyr
                245                 250                 255

Asp Ala Glu Leu Val Trp Gly Gly Gly Asn Gly Ala Pro Thr Ser
            260                 265                 270

Phe Asn Ser Leu Asn Cys Thr Leu Gly Leu Tyr Tyr Ile Ser Asn Gly
        275                 280                 285

Ser Ile Thr Pro Val Pro Ser Leu Tyr Thr Phe Gly Ala Asp Thr Ala
    290                 295                 300

Glu Ala Ala Tyr Asn Val Tyr Thr Thr Met Asn Asn Gly Val Pro Ile
305                 310                 315                 320

Ala Tyr Asn Gly Ile Glu Asn Leu Thr Ile Leu Thr Asn Asn Phe Ser
                325                 330                 335

Val Ile Leu Ile
            340
```